United States Patent
Kieber-Emmons et al.

(10) Patent No.: US 10,272,144 B2
(45) Date of Patent: Apr. 30, 2019

(54) COMPOSITIONS FOR AND METHODS OF TREATING AND PREVENTING TARGETING TUMOR ASSOCIATED CARBOHYDRATE ANTIGENS

(71) Applicant: Board of Trustees of the University of Arkansas, Little Rock, AR (US)

(72) Inventors: Thomas Kieber-Emmons, Little Rock, AR (US); Anastas Pashov, Little Rock, AR (US); Behjatolah Karbassi, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 137 days.

(21) Appl. No.: 14/908,503

(22) PCT Filed: Jul. 31, 2014

(86) PCT No.: PCT/US2014/049309
§ 371 (c)(1),
(2) Date: Jan. 28, 2016

(87) PCT Pub. No.: WO2015/017734
PCT Pub. Date: Feb. 5, 2015

(65) Prior Publication Data
US 2016/0184415 A1    Jun. 30, 2016

Related U.S. Application Data

(60) Provisional application No. 61/860,827, filed on Jul. 31, 2013.

(51) Int. Cl.
| | |
|---|---|
| *A61K 39/00* | (2006.01) |
| *C07K 16/32* | (2006.01) |
| *A61K 45/06* | (2006.01) |
| *A61K 31/138* | (2006.01) |
| *A61K 31/337* | (2006.01) |
| *A61K 31/475* | (2006.01) |
| *A61K 31/675* | (2006.01) |
| *A61K 31/704* | (2006.01) |
| *A61K 35/15* | (2015.01) |
| *A61K 35/17* | (2015.01) |
| *A61K 31/7024* | (2006.01) |
| *A61K 39/39* | (2006.01) |
| *C07K 7/08* | (2006.01) |
| *C07K 16/18* | (2006.01) |
| *C12N 5/0783* | (2010.01) |

(Continued)

(52) U.S. Cl.
CPC ........ *A61K 39/0005* (2013.01); *A61K 31/138* (2013.01); *A61K 31/337* (2013.01); *A61K 31/475* (2013.01); *A61K 31/675* (2013.01); *A61K 31/704* (2013.01); *A61K 31/7024* (2013.01); *A61K 35/15* (2013.01); *A61K 35/17* (2013.01); *A61K 39/0011* (2013.01); *A61K 39/39* (2013.01); *A61K 45/06* (2013.01); *C07K 7/08* (2013.01); *C07K 14/4748* (2013.01); *C07K 16/18* (2013.01); *C07K 16/32* (2013.01); *C12N 5/0646* (2013.01); *C12N 5/0694* (2013.01); *A61K 2039/507* (2013.01); *A61K 2039/5154* (2013.01); *A61K 2039/5158* (2013.01); *A61K 2039/55* (2013.01); *A61K 2039/55566* (2013.01); *A61K 2039/572* (2013.01); *A61K 2039/575* (2013.01); *A61K 2039/585* (2013.01); *A61K 2039/605* (2013.01); *C07K 2317/73* (2013.01); *C07K 2319/00* (2013.01); *C07K 2319/33* (2013.01)

(58) Field of Classification Search
CPC ........ A61K 2300/00; A61K 2039/5158; A61K 2039/55566; A61K 2039/572; A61K 2039/575; A61K 2039/585; A61K 2039/605; A61K 39/00; A61K 39/0005; A61K 39/0011; A61K 39/39; C07K 14/4748; C07K 2317/73; C07K 2319/00; C07K 2319/33; C07K 7/08
See application file for complete search history.

(56) References Cited

U.S. PATENT DOCUMENTS

| 4,945,050 A | 7/1990 | Sanford et al. |
| 5,036,006 A | 7/1991 | Sanford et al. |
| 5,225,539 A | 7/1993 | Winter |

(Continued)

FOREIGN PATENT DOCUMENTS

| WO | 1997026784 A1 | 7/1997 |
| WO | 1999065522 A1 | 12/1999 |

(Continued)

OTHER PUBLICATIONS

Anahit Ghochikyan, Rationale for Peptide and DNA Based Epitope Vaccines for Alzheimer's Disease Immunotherapy, CNS Neurol Disord Drug Targets. Apr. 2009 ; 8(2): 128.*

(Continued)

*Primary Examiner* — Rachael E Bredefeld
*Assistant Examiner* — Erinne R Dabkowski

(57) ABSTRACT

Compositions useful to induce anti-TACA immune response and kits comprising the same and methods of using the compositions to treat and prevent cancer are disclosed. Isolated human antibodies which bind to a carbohydrate mimetic peptide and methods of making the same and using the same to treat and prevent cancer are disclosed. Isolated human NK cells useful to kill tumor cells, and isolated human dendritic cells, and methods of making the same and using the same to treat and prevent cancer are disclosed.

43 Claims, 18 Drawing Sheets
Specification includes a Sequence Listing.

(51) Int. Cl.
*C12N 5/09* (2010.01)
*C07K 14/47* (2006.01)

(56) References Cited

U.S. PATENT DOCUMENTS

| | | | |
|---|---|---|---|
| 5,273,525 | A | 12/1993 | Hofmann |
| 5,439,440 | A | 8/1995 | Hofmann |
| 5,530,101 | A | 6/1996 | Queen et al. |
| 5,580,859 | A | 12/1996 | Felgner et al. |
| 5,585,089 | A | 12/1996 | Queen et al. |
| 5,593,972 | A | 1/1997 | Weiner et al. |
| 5,676,594 | A | 10/1997 | Joosten |
| 5,702,359 | A | 12/1997 | Hofmann et al. |
| 5,703,055 | A | 12/1997 | Felgner et al. |
| 5,736,142 | A | 4/1998 | Sette et al. |
| 5,739,118 | A | 4/1998 | Carrano et al. |
| 5,810,762 | A | 9/1998 | Hofmann |
| 5,817,637 | A | 10/1998 | Weiner et al. |
| 5,830,876 | A | 11/1998 | Weiner et al. |
| 5,962,428 | A | 10/1999 | Carrano |
| 5,981,505 | A | 11/1999 | Weiner et al. |
| 5,993,434 | A | 11/1999 | Dev et al. |
| 6,014,584 | A | 1/2000 | Hofmann et al. |
| 3,055,453 | A | 4/2000 | Hofmann et al. |
| 3,068,650 | A | 5/2000 | Hofmann et al. |
| 6,110,161 | A | 8/2000 | Mathiesen et al. |
| 6,120,493 | A | 9/2000 | Hofmann |
| 6,135,990 | A | 10/2000 | Heller et al. |
| 6,181,964 | B1 | 1/2001 | Hofmann et al. |
| 6,216,034 | B1 | 4/2001 | Hofmann et al. |
| 6,233,482 | B1 | 5/2001 | Hofmann et al. |
| 6,241,701 | B1 | 6/2001 | Hofmann |
| 6,347,247 | B1 | 2/2002 | Dev et al. |
| 6,413,517 | B1 | 7/2002 | Sette et al. |
| 6,413,935 | B1 | 7/2002 | Alexander et al. |
| 6,418,341 | B1 | 7/2002 | Hofmann et al. |
| 6,451,002 | B1 | 9/2002 | Dev et al. |
| 6,516,223 | B2 | 2/2003 | Hofmann |
| 6,567,694 | B2 | 5/2003 | Hayakawa |
| 6,569,149 | B2 | 5/2003 | Dev et al. |
| 6,602,510 | B1 | 8/2003 | Fikes et al. |
| 6,610,044 | B2 | 8/2003 | Mathiesen |
| 6,654,636 | B1 | 11/2003 | Dev et al. |
| 6,678,556 | B1 | 1/2004 | Nolan et al. |
| 6,697,669 | B2 | 2/2004 | Dev et al. |
| 6,763,264 | B2 | 7/2004 | Hofmann |
| 6,778,853 | B1 | 8/2004 | Heller et al. |
| 6,865,416 | B2 | 3/2005 | Dev et al. |
| 6,939,862 | B2 | 9/2005 | Bureau et al. |
| 6,958,060 | B2 | 10/2005 | Mathiesen et al. |
| 6,960,566 | B1 | 11/2005 | Blaszczyk-Thurin |
| 7,202,351 | B1 | 4/2007 | Sette et al. |
| 7,245,963 | B2 | 7/2007 | Draghia-Akli et al. |
| 7,462,354 | B2 | 12/2008 | Sette et al. |
| 9,249,187 | B2 | 2/2016 | Degan et al. |
| 2003/0017497 | A1* | 1/2003 | Kieber-Emmons .... G01N 33/66 435/7.1 |
| 2003/0224036 | A1 | 12/2003 | Fikes et al. |
| 2005/0049197 | A1 | 3/2005 | Sette et al. |
| 2005/0181987 | A1 | 8/2005 | Blaszczyk-Thurin et al. |
| 2007/0098776 | A1 | 5/2007 | Fikes et al. |
| 2008/0279924 | A1 | 11/2008 | Fikes et al. |
| 2010/0150953 | A1 | 6/2010 | Humphreys et al. |
| 2010/0183708 | A1 | 7/2010 | Bonnet et al. |

FOREIGN PATENT DOCUMENTS

| | | | |
|---|---|---|---|
| WO | 2001041741 | A1 | 6/2001 |
| WO | 2003040165 | A | 5/2003 |
| WO | 2010086294 | A2 | 8/2010 |
| WO | 2011156751 | A2 | 12/2011 |
| WO | 2015143126 | A1 | 9/2015 |

OTHER PUBLICATIONS

UCSF Medical CEnter, Breast Cancer Treatment, published online Nov. 10, 2016.*
L A Emens, Breast cancer vaccines: maximizing cancer treatment by tapping into host immunity, Endocrine-Related Cancer (2005) 12 1-17.*
Bonhoure, Fabien,Montanide ISA 51 VG as Adjuvant for Human Vaccines , Journal of Immunotherapy Issue: vol. 29(6), Nov./Dec. 2006, pp. 647-648.*
Cecile Artaud, A GD2 peptide mimic stimulates NK anti-tumor activity in breast cancer models through a thymus independent immune response, AACR Annual Meeting—Apr 12-16, 2008; San Diego, CA.*
NIH, Clinical Trials.gov, Jul. 8, 2011, Vaccination of high Risk breast cancer patients.*
Mechanisms of Carcinogenesis, section, 2008, International Agency for research on Cancer.*
Kieber-Emmons, Thomas, Annual Report; Award No. W81XWH-06-1-0542; Title: Vaccination of High-Risk Breast Cancer Patients with Carbohydrate Mimicking Peptides; Report Date: May 2007; Prepared For: U.S. Army Medical Research and Material Command Fort Detrick, Maryland 21702-5012; pp. 1-85.
Kieber-Emmons, Thomas, Annual Report; Award No. W81XWH-06-1-0542; Title: Vaccination of High-Risk Breast Cancer Patients with Carbohydrate Mimicking Peptides; Report Date: May 2008; Prepared For: U.S. Army Medical Research and Material Command Fort Detrick, Maryland 21702-5012; pp. 1-111.
Vaccination of High Risk Breast Cancer; ClinicalTrials.gov identifier NCT01390064; ClinicalTrials.gov; pp. 1-21.
Kieber-Emmons, Thomas, Annual Report; Award No. W81XWH-06-1-0542; Title: Vaccination of High-Risk Breast Cancer Patients with Carbohydrate Mimicking Peptides; Report Date: May 2009; Prepared For: U.S. Army Medical Research and Material Command Fort Detrick, Maryland 21702-5012; pp. 1-495.
Craig L. Slingluff Jr, et al.; "Randomized MulticenterTrial of the effectsof Melanoma-Associated Helper Peptides and Cyclophosphamide on the Immunogenicity of a Multipeptide Melanoma Vaccine"; J Clin Oncol (2011); 29 (21):2924-2932.
Craig L. Slingluff Jr, et al.; "Immunogenicity for CD8+ and CD4+ T Cells in 2 Formulations of an Incomplete Freund's Adjuvant for Multipeptide Melanoma Vaccines"; J Immunother (2010); 33(6):630-638.
Neil L. Berinstein, et al. "First-in-man application of a novel therapeutic cancer vaccine formulation with the capacity to induce multi-functional T cell responses in ovarian, breast and prostate cancer patients"; Journal of Translational Medicine (2012); 10:156 pp. 1-12.
B. Monzavi-Karbassi et al., "Preclinical studies of carbohydrate mimetic peptide vaccines for breast cancer and melanoma"; Vaccine 25 (2007) 3022-3031.
A. Pashov et al.; "Immune surveillance and immunotherapy: Lessons from carbohydrate mimotopes"; Vaccine 27 (2009) 3405-3415.
A. Pashov, et al.; "Peptide Mimotopes as Prototypic Templates of Broad-Spectrum Surrogates of Carbohydrate Antigens for Cancer Vaccination"; Critical Reviews™ in Immunology, 27(3)247-270 (2007).
A. Pashov, et al.; "Carbohydrate Mimotopes in the Rational Design of Cancer Vaccines"; Current Topics in Medicinal Themistry, 2005, vol. 5, No. 12.
Jeff Alexander, et al. "Linear PADRE T Helper EPitope and Carbohydrate B Cell Epitope Conjugates Induce Specific High Titer IgG Antibody Responses" The Journal of Immunology, 2000, 1625-1633.
Agadjanyan M.G., Prototype Alzheimer's Disease Vaccine Using the Immunodominant B Cell Epitope from Beta-amyloid and Promiscuous T Cell Epitope Pan HLA DR-binding peptide, J Immunol, 2005, 1580-1586, 174(3).
Alexander J., Linear PADRE T Helper Epitope and Carbohydrate B Cell Epitope Conjugates Induce Specific High Titer IgG Antibody Responses, J Immunol, 2000, 1625-1633, 164(3).
Bargieri D.Y., Adjuvant Requirement for Successful Immunization with Recombinant Derivatives of Plasmodium Vivax Merozoite

(56) References Cited

OTHER PUBLICATIONS

Surface Protein-1 Delivered via the Intranasal Route, Mem Inst Oswaldo Cruz, 2007, 313-317, 102(3).
Calvo-Calle J.M., Human CD4+ T Cell Epitopes from Vaccinia Virus Induced by Vaccination or Infection, PLoS Pathogens, 2007, e144, 3(10).
Heller K.N., Distinct Memory CD4+ T-cell Subsets Mediate Immune Recognition of Epstein Barr Virus Nuclear Antigen 1 in Healthy Virus Carriers, Blood, 2007, 1138-1146, 109.
Hennings L., Carbohydrate Mimetic Peptides Augment Carbohydrate-reactive Immune Responses in the Absence of immune Pathology, Cancers, 2011, 4151-4169, 3(4).
James E.A., Tetramer-guided Epitope Mapping Reveals Broad, Individualized Repertoires of Tetanus Toxin-specific CD4+ T Cells and Suggests HLA-based Differences in Epitope Recognition, Int Immunol, 2007, 1291-1301, 19(11).
Kieber-Emmons T., The Promise of the Anti-idiotype Concept, Front Oncol, 2012, 196, 2.
Kieber-Emmons T., Cutting Edge: DNA Immunization with Minigenes of Carbohydrate Mimotopes Induce Functional Anti-carbohydrate Antibody Response, J Immunol, 2000, 623-627, 165(2).
Kobayashi H., Induction of EBV-latent Membrane Protein 1-Specific MHC Class II-Restricted T-cell Responses Against Natural Killer Lymphoma Cells, Cancer Res, 2008, 901-908, 68(3).
Korourian S., Expression Analysis of Carbohydrate Antigens in Ductal Carcinoma in Situ of the Breast by Lectin Histochemistry, BMC Cancer, 2008, 8(136).
Leen A.M., Identification of Hexon-specific CD4 and CD8 T-cell Epitopes for Vaccine and Immunotherapy, J Viral 2008, 546-554, 82(1).
Liu D.W., Recombinant Adeno-associated Virus Expressing Human Papillomavirus Type 16 E7 Peptide DNA Fused with Heat Shock Protein DNA as a Potential Vaccine for Cervical Cancer, J Virol, 2000, 2888-2894, 74(6).
MacMillan H., Physical Linkage of Naturally Complexed Bacterial Outer Membrane Proteins Enhances Immunogenicity, Infect Immun, 2008, 1223-1229, 76(3).
Monzavi-Karbassi B., Reduction of Spontaneous Metastases Through Induction of Carbohydrate Cross-reactive Apoptotic Antibodies, J Immunol, 2005, 7057-7065, 174(11).
Monzavi-Karbassi B., Immunization with a Carbohydrate Mimicking Peptide Augments Tumor-specific Cellular Responses, Int Immunol, 2001, 1361-1371, 13(11).
Monzavi-Karbassi B., A Mimic of Tumor Rejection Antigen-associated Carbohydrates Mediates an Antitumor Cellular Response, Cancer Res, 2004, 2162-2166, 64(6).
Monzavi-Karbassi B., Evaluating Strategies to Enhance the Antitumor Immune Response to a Carbohydrate Mimetic Peptide Vaccine, Int J Mol Med, 2006, 1045-1052, 17(6).
Monzavi-Karbassi B., Tumor-Associated Glycans and Immune Surveillance, Vaccines, 2013, 174-203, 1(2).
Moro M., Generation of Functional HLA-DR*1101 Tetramers Receptive for Loading with Pathogen or Tumour Derived Synthetic Peptides, BMC Immunol, 2005, 6:24.
Pajot A., The Th1 Immune Response Against HIV-1 Gag p24-derived Peptides in Mice Expressing HLA-A02.01 and HLA-DRI, Eur J Immunol, 2007, 2635-2644, 37.
Pashov A., Immune Surveillance as a Rationale for Immunotherapy?, Hum Vaccin, 2007, 224-228, 3(5).
Pashov A., Glycan Mediated Immune Responses to Tumor Cells, Hum Vaccin, 2011, Suppl:156-65.
Pashov A., Bridging Innate and Adaptive Antitumor Immunity Targeting Glycans, J Biomed Biotechnol, 2010, 354068.
Piriou E.R., Novel Method for Detection of Virus-specific CD4+ T Cells Indicates a Decreased EBV-specific CD4+ T cell Response in Untreated HIV-infected Subjects, Eur J Immunol, 2005, 796-805, 35(3).
Renard V., HER-2 DNA and Protein Vaccines Containing Potent Th cell Epitopes Induce Distinct Protective and Therapeutic Antitumor Responses in HER-2 Transgenic Mice, J Immunol, 2003, 1588-1595, 171(3).
Schilienger K., Efficient Priming of Protein Antigen-specific Human CD4(+) T Cells by Monocyte-derived Dendritic Cells, Blood, 2000, 3490-3498, 96(10).
Su Z., Enhanced Induction of Telomerase-specific CD4(+) T Cells Using Dendritic Cells Transfected with RNA Encoding a Chimeric Gene Product, Cancer Res, 2002, 5041-5048, 62(17).
Wondimu A., Peptides Mimicking GD2 Ganglioside Elicit Cellular, Humoral and Tumor-protective Immune Responses in Mice, Cancer Immunol Immunother, 2008, 1079-1089, 57(7).
You Z., Induction of Vigorous Helper and Cytotoxic T Cell as well as B Cell Responses by Dendritic Cells Expressing a Modified Antigen Targeting Receptor-mediated Internalization Pathway, J Immunol, 2000, 4581-4591, 165(8).
Zhang X., Th-cytotoxic T-lymphocyte Chimeric Epitopes Extended by Nepsilon-palmitoyl Lysines Induce Herpes Simplex Virus Type 1-specific Effector CD8+ Tel Responses and Protect Against Ocular Infection, J Virol, 2005, 15289-15301, 79(24).
Merrifield R.B., Solid Phase Peptide Synthesis. I. The Synthesis of a Tetrapeptide, J Am Chem Soc, 1963, 2149-2154, 85(14).
Larrick J.W., Recombinant Antibodies, Hum Antibodies Hybridomas, 1991, 172-189, 2(4).
Winter G., Man-made Antibodies, Nature, 1991, 293-299, 349(6307).
Magerstadt M., Antibody Conjugates and Malignant Disease, 1991, CRC Press, Boca Raton, USA, pp. 110-152.
Borgelt B., The Palliation of Brain Metastases: Final Results of the First Two Studies of the Radiation Therapy Oncology Group, Int J Radiat Oncol Biol Phys, 1980, 1-9, 6(1).

* cited by examiner

COMPOSITIONS FOR AND METHODS OF TREATING AND PREVENTING TARGETING TUMOR ASSOCIATED CARBOHYDRATE ANTIGENS

This application claims priority to U.S. Provisional Application No. 61/860,827 filed Jul. 31, 2013, which is incorporated herein by reference.

STATEMENT OF GOVERNMENT RIGHTS

This invention was made under support from the United States federal government including a Clinical Translation Research Award by the US Army Breast Cancer Program (W81XWH-06-1-0542). The U.S. Government may have certain rights in this invention.

FIELD OF THE INVENTION

The invention relates to vaccines, isolated antibodies, isolated immune cells and methods of making and using the same to treat and prevent breast cancer.

BACKGROUND OF THE INVENTION

Anti-tumor immune responses are a facet of the tissue-specific autoimmune phenomenon. The generation of immune responses to tissue rejection antigens, therefore, represents an important conceptual approach in cancer immunotherapy. Tumor-associated carbohydrate antigens (TACAs) are potential tissue rejection antigen targets that display tissue-specific variation, with both T cells and antibodies recognizing mono- and disaccharide constituents of TACA.

Glycosylation regulates NK cell-mediated effector function through the PI3K pathway. Interference with N-glycosylation has been shown both to reduce the membrane expression of MHC class I and to increase the in vitro sensitivity of tumor cells to NK cell killing. Early on it was recognized that compounds that inhibit glycosylation pathways could affect the growth of tumor cells in tumor bearing animals. Castanospermine, swainsonine and tunicamycin block different steps in the pathway of glycoprotein processing yet each are potent inhibitors of tumor cell dissemination and tumor colonization. This suggested blocking at one of at least two steps could have beneficial effects on tumor cell growth. The antimetastatic effect of tunicamycin may be related to interference in tumor cell-extracellular matrix interactions, whereas treatment with castanospermine or swainsonine appears to block at a stage distal to initial tumor cell arrest. Swainsonine in particular is interesting as it inhibits the formation of N-linked complex oligosaccharides with this inhibition correlative with enhancement with NK cell function. Consequently inhibitors of N- as well as O-linked glycosylation should be useful for the treatment of cancer by affectively resetting NK functional activity by disruption of negative signals; given that inhibitors can be specifically targeted to tumor tissue. More recently Bortezomib (Velcade) as a proteasome inhibitor is purported to increase the sensitivity of tumor cells to NK activity by down modulating MHC Class I expression. N-linked glycosylation does not impair proteasomal degradation but affects Class I MHC presentation. Conversion of the glycosylated Asn (N) into Asp (D) in proteasomal breakdown products is mediated by PNGase. PNGase can act following proteasomal degradation. As a result, class I MHC antigen presentation is markedly reduced.

The orchestration of glycan remodeling and galectin-1 up-regulation by the tumor suppressor $p16^{INK4a}$ pancreatic carcinoma cells to reconstitute susceptibility to anoikis underscores the potential and tight control of this lectin. Anti-glycan antibodies can function like lectins, mediating cell death signals and cell growth signals. Other Galectins can promote NK cell-mediated anti-tumor activity by expanding unique phenotypes. Co-culture of naïve NK cells with macrophages from Gal-9-treated mice resulted in enhanced NK activity, although Gal-9 itself did not enhance the NK activity. Antibodies can do the same. Expansion of natural killer cells in mice transgenic for IgM antibody to ganglioside GD2 was demonstrated to prolong survival after challenge with syngeneic tumor cells. Depletion of NK cells with anti-asialo GM1 rabbit serum reduced or abrogated the observed anti-tumor effects, suggesting that NK cells play a major role in tumor eradication or suppression. These results suggest that NK cell responses may be specifically enhanced, after vaccination, from CMP-specific B cells in a manner that confers a NK phenotype for local expansion of NK activity for the tumor.

United States Patent Publication Nos. 20030017497 and 20050181987 each disclose peptide mimotopes of carbohydrate antigens and methods of using such peptides in the treatment of cancer. Carbohydrate mimetic peptides (CMPs) stimulate immune responses targeting TACAs that effectively promote tumor growth inhibition in mouse models of cancer. CMPs are broad-spectrum immunogens, inducing responses to multiple TACAs and therefore obviating the need for multivalent carbohydrate-based vaccines. Among CMPs are those that use aromatic-aromatic and hydrophobic interactions as critical chemical forces that modulate binding of the CMPs to anti-carbohydrate antibodies. The tumor growth inhibition upon immunization with CMPs having a central motif of Tyr-Arg-Tyr or Trp-Arg-Tyr has been observed.

Preclinical studies of carbohydrate mimetic peptide vaccines for breast cancer and melanoma are disclosed in Monzavi-Karbassi, B. et al. (2007) Vaccine 27:3022-3031. The immunogen is includes a P10s multiple antigen peptide (MAP) form as well as three other peptides P10, CMP 106 and CMP 107, each also provided as a MAP form. A MAP form of a peptide is a polypeptide having multiple repeating sequences of the peptide. MAP forms of a peptide typically have 2-10 copies of the peptide.

Hennings, L. et al. (2011) Cancers 3:4151-4169 disclose that carbohydrate mimetic peptides augment carbohydrate-reactive immune responses in the absence of immune pathology. Peptides P10, CMP 106 and CMP 107 are referred to and data show immune responses against CMPs do not have harmful effects on normal cells that contain carbohydrates.

SUMMARY OF THE INVENTION

Composition comprising P10s (SEQ ID NO:1) or a variant thereof linked to a CD4+ helper T cell epitope are provided. In some embodiments, the composition comprises P10s-PADRE wherein "P10s-PADRE" refers to: H-Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH2 in which Ala13 and Ala25 are each D amino acids shown as dAla, and Ala at position 15 is a modified L configuration Alanine, cyclohexylalanine shown as CHAla. In some embodiments, the composition comprises P10s linked to a PADRE peptide, said P10s linked to a PADRE peptide comprises the amino acid sequence Trp-Arg-Tyr-Thr-Ala- Pro-Val-His-Leu-Gly-Asp-Gly-dAla-Lys-CHAla-Val-Ala-Ala-Trp-Thr-Leu-Lys-Ala-Ala-dAla in which Ala13 and Ala25 are each D amino acids shown as dAla, and Ala at position 15 is a modified L configuration Alanine, cyclohexylalanine shown as CHAla. In some embodiments, the composition comprises P10s or a variant thereof linked to a PADRE peptide (e.g. dAla-Lys-CHAla-Val-Ala-Ala-Trp-Thr-Leu-Lys-Ala-Ala-dAla, SEQ ID NO:3, SEQ ID NO:4 or SEQ ID NO:5 or another PADRE peptide). In some embodiments, the composition comprises P10s or a variant thereof linked to a CD4+ helper T cell epitope other than PADRE. In some embodiments the C terminus of the peptide is amidated. In some embodiments, the composition comprises P10s linked to a CD4+ helper T cell epitope PADRE having the sequence dAla-Lys-CHAla-Val-Ala-Ala-Trp-Thr-Leu-Lys-Ala-Ala-dAla. In some embodiments, the composition comprises P10s linked to a CD4+ helper T cell epitope PADRE having the sequence dAla-Lys-CHAla-Val-Ala-Ala-Trp-Thr-Leu-Lys-Ala-Ala-dAla and having an amidated "C terminus". In some embodiments, the composition comprises P10s linked to a generic PADRE having SEQ ID NO:3, SEQ ID NO:4, SEQ ID NO:5 or another PADRE peptide. In some embodiments, the composition comprises P10s linked to a CD4+ helper T cell epitope other than PADRE.

In some embodiments, composition described herein further comprising adjuvant. In some embodiments, the compositions further comprising an adjuvant selected from the group consisting of MONTANIDE™ ISA 51 VG adjuvant and QS21 adjuvant. In some embodiments, the compositions further comprising an adjuvant selected from the group consisting of adjuvants other than MONTANIDE™ ISA 51 VG adjuvant and QS21 adjuvant.

In some embodiments, the composition comprises P10s-PADRE and MONTANIDE™ ISA 51 VG adjuvant and QS21 adjuvant. In some embodiments, the composition comprises P10s-PADRE and an adjuvant selected from the group consisting of adjuvants other than MONTANIDE™ ISA 51 VG adjuvant and QS21 adjuvant. Such compositions may comprises at least 300 µg P10s-PADRE; and in some embodiment at least 500 µg P10s-PADRE and in some embodiments at least 1000 µg P10s-PADRE.

Compositions are provided which comprise a plurality of isolated human antibodies, wherein said isolated human antibodies bind to P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs. Said plurality of isolated human antibodies that bind to P10s-PADRE and are cytotoxic to cultured cancer cells represented by human breast cell line MDA-231 and HCC1954 cells may be isolated from an individual vaccinated with P10s or a variant thereof, or P10s or a variant thereof linked to a CD4+ helper T cell epitope such as for example PADRE.

Compositions are provided which comprise a plurality of isolated monoclonal antibodies, wherein said isolated human antibodies bind to P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs. Said plurality of isolated monoclonal antibodies that bind to P10s-PADRE and are cytotoxic to cultured cancer cells represented by human breast cell line MDA-231 and HCC1954 cells may be derived from one or more B cells isolated from an individual vaccinated with P10s or a variant thereof, or P10s or a variant thereof linked to a CD4+ helper T cell epitope such as for example PADRE.

Compositions are provided which comprise a plurality of isolated humanized antibodies, wherein said isolated human antibodies bind to P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs. Said plurality of isolated humanized antibodies that bind to P10s-PADRE and are cytotoxic to cultured cancer cells represented by human breast cell line MDA-231 and HCC1954 cells may be derived from one or more B cells isolated from an individual vaccinated with P10s or a variant thereof, or P10s or a variant thereof linked to a CD4+ helper T cell epitope such as for example PADRE.

Composition are provided which comprise compositions described herein and further comprise an anti-cancer chemotherapeutic or anti-cancer radioactive agent.

Kits are provided which comprise a first container comprising a composition described herein and a second container comprising an anti-cancer chemotherapeutic or anti-cancer radioactive agent.

Pluralities of isolated cells that produce human antibodies that bind to P10s and/or P10s-PADRE and are cytotoxic to cultured cancer cells are provided. Cultured cancer cells may be represented by human breast cell line MDA-231, which is a so called basel-like or triple negative tumor cell line, and HCC1954 cells, which are Her2+ cells and considered de novo resistant to select cancer fighting drugs. Said plurality of isolated cells may be derived from an individual vaccinated with P10s or a variant thereof, or P10s or a variant thereof linked to a CD4+ helper T cell epitope such as for example PADRE, or from genetic material derived from such an individual.

Pluralities of isolated cells that produce monoclonal antibodies that bind to P10s and/or P10s-PADRE and are cytotoxic to cultured cancer cells are provided. Cultured cancer cells may be represented by human breast cell line MDA-231, which is a so called basel-like or triple negative tumor cell line, and HCC1954 cells, which are Her2+ cells and considered de novo resistant to select cancer fighting drugs. Said plurality of isolated cells may be derived from an individual vaccinated with P10s or a variant thereof, or P10s or a variant thereof linked to a CD4+ helper T cell epitope such as for example PADRE, or from genetic material derived from such an individual.

Pluralities of isolated cells that produce humanized antibodies that bind to P10s and/or P10s-PADRE and are cytotoxic to cultured cancer cells are provided. Cultured cancer cells may be represented by human breast cell line MDA-231, which is a so called basel-like or triple negative tumor cell line, and HCC1954 cells, which are Her2+ cells and considered de novo resistant to select cancer fighting drugs. Said plurality of isolated cells may be derived from an individual vaccinated with P10s or a variant thereof, or P10s or a variant thereof linked to a CD4+ helper T cell epitope such as for example PADRE.

An isolated B cell or progeny thereof is provided. The isolated B cells produce human antibodies that bind to P10s and/or P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs, are provided. Said isolated B cell may be obtained from a human immunized with P10s, a variant thereof, or a composition of described herein. B cells are isolated from the immunized human and an isolated B cell that produces human antibodies that bind to P10s and/or P10s-PADRE and are cytotoxic to cultured cancer cells represented by MDA-231 and HCC1954 cells is identified. The B cell may be cultured to produce progeny and/or its genetic material processed to isolate nucleic acid sequences that encode the antibody. The nucleic acid sequences that encode the antibody may then be inserted into an expression vector and introduced into a cell which can produce the antibodies. An isolated B cell that produces human antibodies that bind to P10s and/or P10s-PADRE and are cytotoxic to MDA-231 cells and HCC1954 cells may be obtained by i) isolating B cells from a naive human, ii) exposing the isolated B cells to P10s or a variant thereof and/or P10s-PADRE or another immunizing composition of described herein, iii) identifying an isolated B cell that produces human antibodies that bind to P10s and/or P10s-PADRE and are MDA-231 cells and HCC1954 cells, and iv) expanding the population of the isolated B cell that produced anti-P10s/P10s-PADRE antibodies. The B cell may be cultured to produce progeny and/or its genetic material processed to isolate nucleic acid sequences that encode the antibody. The nucleic acid sequences that encode the antibody may then be inserted into an expression vector and introduced into a cell which can produce the antibodies. B cell that produce anti-P10s/P10s-PADRE antibodies can be administered to a patient diagnosed with cancer or identified as being at a high risk for cancer.

Pluralities human antibodies that bind to P10s and/or P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs may be produced by exposing an animal to P10s-PADRE, preparing hybridomas from cells of the animal, and identifying the hybridoma that produces antibodies, that bind to P10s and/or P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs is identified. The hybridoma may be cultured to produce progeny that produce the antibody and/or its genetic material processed to isolate nucleic acid sequences that encode the antibody. The nucleic acid sequences that encode the antibody may then be inserted into an expression vector and introduced into a cell which can produce the antibodies. The nucleic acid sequences that encode the antibody may be used to produce nucleotide sequences that encode humanized antibodies, such nucleotide sequences are then inserted into an expression vector and introduced into a cell that can produce the humanized antibodies Isolated human NK cells are provided. In some embodiments, the isolated human NK cells are selected from the group consisting of isolated human NK cells obtained from a human immunized with a composition described herein, and progeny of isolated human NK cells obtained from a human immunized with a composition of described herein. In some embodiments, the isolated human NK cells obtained from a naïve human, activated ex vivo with a composition described herein, and progeny of isolated human NK cells obtained from a nave human and activated ex vivo with a composition described herein.

Isolated human dendritic cells are provided. In some embodiments, the isolated human dendritic cells are selected from the group consisting of isolated human dendritic cells obtained from a human immunized with a composition described herein, and progeny of isolated human dendritic cells obtained from a human immunized with a composition described herein. In some embodiments, the isolated human dendritic cells obtained from a naïve human, activated ex vivo with a composition described herein, and progeny of isolated human dendritic cells obtained from a naïve human and activated ex vivo with a composition described herein.

Methods of treating a human who has been diagnosed having cancer are provided. The methods comprise administering to said human a composition described herein.

Methods of treating a human who has been diagnosed as having cancer are provided. The methods comprise administering to said human a composition described herein to chemosensitize tumor cells and administering to said human a chemotherapeutic.

Methods of treating a human who has been diagnosed as having cancer are provided. The methods comprise administering to said human a composition described herein to radiosensitize tumor cells and exposing said human to therapeutic radiation.

Methods of treating a human who has been diagnosed as having cancer are provided in which human isolated NK cells described herein are administered to the human treated with a composition described herein.

Methods of treating a human who has been diagnosed as having cancer are provided in which human isolated dendritic cells described herein are administered to the human.

Methods of preventing cancer in a human who is at high risk for cancer are provided. The methods comprise administering to said human a composition of described herein.

Methods of preventing cancer in a human who is at high risk for cancer are provided. The methods comprise administering to said human a composition described herein to chemosensitize tumor cells and administering to said human a chemotherapeutic.

Methods of preventing cancer in a human who is at high risk for cancer are provided. The methods comprise administering to said human a composition described herein to radiosensitize tumor cells and exposing said human to therapeutic radiation.

Methods of preventing cancer in a human who is at high risk for cancer are provided in which human isolated NK cells described herein are administered to the human treated with a composition described herein.

Methods of preventing cancer in a human who is at high risk for cancer are provided in which human isolated dendritic cells described herein are administered to the human.

Methods of making human antibodies bind to P10s and/or P10s-PADRE and are cytotoxic to cultured cancer cells are provided.

Methods of making population of isolated anti-tumor human NK cells that can kill tumor cells in an individual immunized with a composition of described herein are provided.

Methods of making population of isolated anti-tumor human dendritic cells are provided.

BRIEF DESCRIPTION OF FIGURES

FIG. 4 is a bar graph with eight time points in which each time point shows 8 bars corresponding to different dilutions. As shown in the x-axis, data is provided for eight time points: pre-immune, week 1, week 2, week 3, week 4, week 5, week 6 and week 7. For each time point data is shown for eight dilutions. The bar at the left end at each time point corresponds to 1:100. Immediately to the right of 1:100 bar is the 1:200 bar. Immediately to the right of 1:200 bar is the 1:400 bar. Immediately to the right of 1:400 bar is the 1:800 bar. Immediately to the right of 1:800 bar is the 1:1600 bar. Immediately to the right of 1:1600 bar is the 1:3200 bar. Immediately to the right of 1:3200 bar is the 1:6400 bar. Immediately to the right of 1:6400 bar is the 1:12800 bar. FIG. 4 shows 64 data points.

FIG. 4 is a bar graph with eight time points in which each time point shows 8 bars corresponding to different dilutions. As shown in the x-axis, data is provided for eight time points: pre-immune, week 1, week 2, week 3, week 4, week 5, week 6 and week 7. For each time point data is shown for eight dilutions. The bar at the left end at each time point corresponds to 1:100. Immediately to the right of 1:100 bar is the 1:200 bar. Immediately to the right of 1:200 bar is the 1:400 bar. Immediately to the right of 1:400 bar is the 1:800 bar. Immediately to the right of 1:800 bar is the 1:1600 bar. Immediately to the right of 1:1600 bar is the 1:3200 bar. Immediately to the right of 1:3200 bar is the 1:6400 bar. Immediately to the right of 1:6400 bar is the 1:12800 bar. FIG. 4 shows 64 data points.

FIG. 8A shows the effect of pre-immunization and post-immunization plasma samples from four patients on HCC1954 and MDA-MB-231 cells. The data show that the post-immunization plasma has a cytotoxic effect on both the HCC1954 cells and the MDA-MB-231 cells. FIG. 8B shows a bar graph of the quantified cytotoxicity data of the cytotoxicity of post-immunization plasma compared to that of pre-immunization plasma from the four patients. Cytotoxicity in each cell line was quantified by counting live cells in triplicate wells. The data is presented in a bar graph. Cells were seeded and after 24 hours media were refreshed with the media containing 10% of either pre-immune or post-immune plasma samples. Medium containing 10% serum was used as control. 24 hours post treatment, the supernatant was removed, wells washed and live cells were fixed and stained. For each well 3 microscopic fields were counted and averaged. Variation among these fields were used to calculate Error bars. Percent toxicity was calculated based on cell number in control wells.

FIG. 11A shows the cytotoxic effect on HCC1954 cells and MDA-MB-231 cells that pre-immunization plasma and post-immunization plasma collected from one patient (subject 6) which is an extension of data shown in FIG. 8A. In each instance, plasma was collected from trial subjects pre-immunization and post-immunization. The data in FIGS. 8A, 8B, 11A and 11B show antibodies induced in trial subjects by vaccination with P10s-PADRE vaccine were cytotoxic antibodies. FIG. 11A shows the effect of pre-immunization and post-immunization plasma samples on HCC1954 and MDA-MB-231 cells on a single patient (subject 6). In FIG. 11A, live cells were fixed and stained before taking pictures. As in FIG. 8A, the data show that the post-immunization plasma has a cytotoxic effect on both the HCC1954 cells and the MDA-MB-231 cells. FIG. 11B contains data showing that shows the cytotoxicity of post-immunization plasma compared to that of pre-immunization plasma using data from six patients (Subjects 1-6). Cytotoxicity was quantified by counting alive cells remained in triplicate wells. Line plots show cytotoxicity of pre- and post-immune plasma for the six subjects. Paired differences between pre- and post-immune for each subject were calculated and the mean±SD are shown. One-sample t-tests were run on the paired differences for each cell line, and P values are shown.

In FIG. 14A, the filled histogram, shows exposure of cells to FITC-conjugated mouse anti-human IgG antibody only. The dashed line histogram show binding of IgG from pre-immune serum to HCC1954 cells. The solid line histogram show binding of IgG from post-immune serum collected at week 7 to HCC1954 cells. 1:100 dilution of the serum was used for reactivity. FIG. 14B is a bar graph showing that serum from the patient collected 7 weeks post-immunization kills HCC1954 breast cancer cells in vitro. $1 \times 10^4$ cells were seeded in wells of 96-well plate in medium containing 10% FBS. After 24 hours the medium was refreshed with media containing 10% pre-immune or post-immune sera. Medium in control wells contained 10% FBS. Media were refreshed after 24 hours. 48 hours after addition of sera, supernatants were removed, cells fixed and stained with Crystal violet. Percentage of cytotoxicity was calculated based on cell number in control wells. Error bars represent SD based on three replications. The experiment was repeated three times. Two tail Student's t-test was used for comparison of means.

DETAILED DESCRIPTION OF EMBODIMENTS

Figure 1:
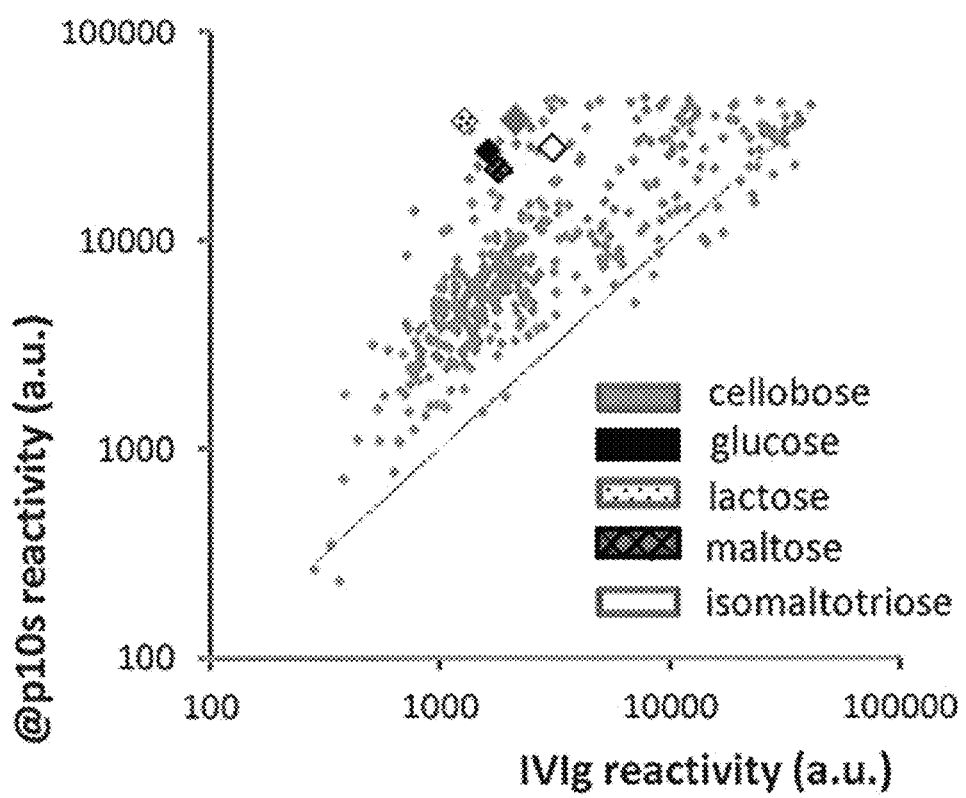
FIG. 1 shows data from a glycan array analysis of the polyreactivity of IgG fraction from intravenous immunoglobulin (IVIg) affinity purified on P10s-PADRE as described in Example 1.

A new vaccine and immunomodulatory procedure is provided herein. A vaccine composition is produced that includes a peptide that includes the sequence from the carbohydrate mimetic peptide (CMP, also called a mimotope) P10s (SEQ ID NO:1) linked to a version of Universal epitope sequence PADRE (dAla-Lys-CHAla-Val-Ala-Ala-Trp-Thr-Leu-Lys-Ala-Ala-dAla). The peptide having these sequences and is amidated at the "C terminus" is referred to as P10s-PADRE and have the formula H-Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH2 in which Ala13 and Ala25 are each D amino acids shown as dALa, and Ala at position 15 is a modified L configuration Alanine, cyclohexylalanine shown as CHAla. The peptide is combined with adjuvant such as MONTANIDE™ ISA 51 VG adjuvant or QS21 adjuvant to produce a vaccine composition that induced immune responses which target TACAs. The vaccine composition when administered to humans can induce broad anti-tumor immune responses including carbohydrate reactive antibodies and other immune responses.

The immune response may have different functionalities such as, for example, cytotoxic effects on tumor cells, or effects that mediate NK cells anti-tumor cell activity, or effects that that produce remodeling glycan surfaces on tumor cells. The new immunomodulatory procedures using the vaccine composition can be used to treat cancer in patients diagnosed with cancer or to prevent occurrence/recurrence of cancer in high-risk populations. The new immunomodulatory procedures using the vaccine composition can be used in combination with other therapeutic modalities in the treatment of cancer or prevention of occurrence/recurrence of cancer. Vaccine compositions may increase chemosensitivity and/or radiosensitivity of tumors. In this regard, chemotherapeutic or radiotherapeutic treatments that may have been previously ineffective or suboptimal may become more viable by rendering tumors more chemosensitive or radiosensitive, lowering the therapeutic dose of chemotherapeutic or radiation to safer levels with fewer side effects or making chemoresistant tumors chemosensitive or radioresistant tumors radiosensitive. Vaccine compositions may lower the incidence of cancer or recurrence in high risk individuals.

The vaccine compositions and methods of using them can induce immune responses in humans in which the antibodies are cytotoxic to tumor cells. The vaccine compositions induces humoral immune responses in cancer patients including anti-tumor responses. The induced antibodies are cytotoxic. These direct cytotoxic effects of the induced antibodies make the vaccine compositions and methods of using them particularly effective advances in treating and preventing cancer. Antibodies from immunized humans were observed to be cytotoxic in the absence of ADCC, CDC and NK mechanisms.

The vaccine compositions and methods of using them can activate p46 expressing Natural Killer (NK) cells. The phenotype of the NK cells become reset in cancer patients that the NK cells become functional, making them active in vivo against tumors. Analysis of immune responses of human patients administered the vaccine, specifically P10s-PADRE, showed that NK cells were activated. These data were unexpected as data in mice showed no NK activation.

The P10s-PADRE vaccine induces cytotoxic immune responses despite providing much higher and persistent IgG responses compared to other vaccine forms which generate more persistent, higher IgM responses.

Human antibodies produced by the methods of using the vaccine compositions are reactive with the carbohydrate mimetic peptide and can block migration of tumor cells. Human antibodies reactive with the carbohydrate mimetic peptide display a degree of catalytic activities with amylase-like activity.

Human antibodies produced by the methods of using the vaccine compositions remodel the carbohydrate antigen patterns on target cells. The potential Abzyme mediated glycan remodeling mechanism may be the basis of immunotherapeutic anti-tumoral activity in broadly reactive carbohydrate mimicking peptides. Similar mechanism may add also a new therapeutic modality in immunotherapy of infectious diseases. Fast enrichment in various glycosidase-like catalytic antibodies and isolation of B cell clones which produce such antibodies using the P10s target will speed up the development of this field and expand the possibilities for other practical application in the biotechnical and pharmaceutical industry as well as in basic research.

P10s

The carbohydrate mimetic peptides (CMPs) P10s (SEQ ID NO:1) is a truncated version of CMP P10 (SEQ ID NO:2). P10 was identified as a peptide that binds to the anti-ganglioside antibody ME361. P10s is a shortened version of P10, it differs from the sequence of P10 in that the first three N terminal residues of P10 are deleted to form P10s.

PADRE Having DAla1, CHAla3 and DAla13

PADRE which has DAla1, CHAla3 and DAla13 (also referred to as "PADRE$_{DAla1,CHAla3,DAla13}$") is a preferred from of the Pan T cell peptide PADRE peptide. PADRE$_{DAla13,CHAla,DAla25}$ is a 13 amino acid peptide which contains 11 L amino acids including a modified L amino acid and 2 D amino acids. The sequence of PADRE$_{DAla13,CHAla,DAla25}$ is dAla-Lys-CHAla-Val-Ala-Ala-Trp-Thr-Leu-Lys-Ala-Ala-dAla in which Ala1 and Ala13 are each D amino acids shown as dALa, and Ala at position 3 is a modified L configuration Alanine, cyclohexylalanine shown as CHAla.

Adjuvants

Compositions are provided which comprise an adjuvant in an injectable formulation. In some embodiments, the adjuvant is MONTANIDE™ ISA 51 VG adjuvant (Seppic SA, Paris, France). In some embodiments, the adjuvant is QS21 adjuvant (Agenus, Lexington Mass.), a saponin plant extract adjuvant purified from the Soap bark tree (*Quillaja saponaria*). In some embodiments, the adjuvant is formulated with another adjuvant of the group of Montanide ISA Adjuvants (Seppic SA, Paris, France). Montanide ISA Adjuvants are a group of oil/surfactant based adjuvants in which different surfactants are combined with either a non-metabolizable mineral oil, a metabolizable oil, or a mixture of the two. They are prepared for use as an emulsion with aqueous antigen solution. The surfactant for MONTANIDE™ ISA 51 VG adjuvant (ISA=Incomplete Seppic Adjuvant) is mannide oleate, a major component of the surfactant in Freund's adjuvants. The various Montanide ISA group of adjuvants are used as water-in-oil emulsions, oil-in-water emulsions, or water-in-oil-in-water emulsions. MONTANIDE™ ISA 51 VG adjuvant is referred to herein is a specific product. Other Montanide ISA adjuvants include MONTANIDE™ ISA 730 VG Adjuvant™. Seppic SA also provides an extensive line of veterinary vaccine adjuvant. As used herein, reference to "an adjuvant other than MONTANIDE™ ISA 51 VG™ adjuvant or QS21 adjuvant" and references to other adjuvants is intended to refer to other Montanide adjuvants, including but not limited other Montanide ISA adjuvants. In some embodiments, the adjuvant is Freund's Complete Adjuvant (FCA), which is a mixture of a non-metabolizable oil (mineral oil), a surfactant (Arlacel A), and mycobacteria (*M. tuberculosis* or *M. butyricum*). In some embodiments, the adjuvant is Freund's Incomplete Adjuvant (FIA), which has the same oil/surfactant mixture as FCA but does not contain any mycobacteria. In some embodiments, the adjuvant is Ribi's Adjuvants (Ribi ImmunoChem Research, Inc., Hamilton, Mont.), which are a mixture of oil, detergent, and immunostimulator(s) including metabolizable oil (squalene) and modified, detoxified bacterial products. Trehalose dimycolate (TDM) is a mycobacterial component that serves as a surfactant, immunostimulator as and adherence factor in binding protein antigen to the oil droplets. In some embodiments, the adjuvant is Hunter's TiterMax (CytRx Corp., Norcross, Ga.) is an oil/surfactant-based adjuvant that uses a metabolizable oil (squalene) and a nonionic surfactant. The surfactant used a synthetic nonionic block copolymers of polyoxyethylene and polyoxypropylene. In some embodiments, Aluminum Salt Adjuvants are used in alum-precipitated vaccines and in alum-adsorbed vaccines. In some embodiments, the adjuvant is Nitrocellulose-Adsorbed Protein. In some embodiments, the adjuvant is Liposome-entrapped antigen such as for example nondegradable ethylene-vinyl acetate copolymer-entrapped antigen, and degradable polymer-entrapped antigen. Biodegradable, biocompatible such as poly(DL-lactide-co-glycolide) polymers are used for encapsulation. In some embodiments, the adjuvant is Gerbu Adjuvant (Gerbu Biotechnik GmbH, Gaiberg, Germany/C-C Biotech, Poway, Calif.) utilizes immunostimulators in combination with zinc proline. In some embodiments, the adjuvant is one from the group of adjuvants marketed by Invivogen (San Diego, Calif.). These adjuvants including AddaVax™ adjuvant, Alhydrogel 2%, IFA, c-di-AMP VacciGrade™ adjuvant, c-di-GMP VacciGrade™ adjuvant, Flagellin FliC VacciGrade™ adjuvant, Gardiquimod VacciGrade™ adjuvant, Imiquimod VacciGrade™ adjuvant, MPLA-SM VacciGrade™ adjuvant, MPLA Synthetic VacciGrade™ adjuvant, N-Glycolyl-MDP VacciGrade™ adjuvant, ODN 1585 VacciGrade™ adjuvant, ODN 1826 VacciGrade™ adjuvant, ODN 2006 Vaccigrade™ adjuvant, ODN 2395 VacciGrade™ adjuvant, Pam3CSK4 VacciGrade™ adjuvant, Poly (I:C) (HMW) VacciGrade™ adjuvant, R848 VacciGrade™ adjuvant, and TDB VacciGrade™ adjuvant.

In some embodiments, adjuvants that have a natural depot effect may be selected and used. In some embodiments, adjuvants that do not have a natural depot effect may be selected and used. In some embodiments, adjuvants may be formulated to create or increase a depot effect.

P10s-PADRE

"P10s-PADRE" is a peptide in which the P10s peptide is covalently linked to PADRE which has DAla1, CHAla3 and DAla13 forming a 25 amino acid peptide which contains 23 L amino acids including a modified L amino acid and 2 D amino acids. The sequence of P10s-PADRE (which can also be referred to as "PADRE$_{DAla13,CHAla15,DAla25}$") is Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla in which Ala13 and Ala25 are each D amino acids shown as dALa, and Ala at position 15 is a modified L configuration Alanine, cyclohexylalanine shown as CHAla. The peptide has a hydrogen at the N terminus and NH$_2$ at the C terminus. The formula representing the structure of P10s-PADRE is H-Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH$_2$ in which Ala13 and Ala25 are each D amino acids shown as dALa, and Ala at position 15 is a modified L configuration Alanine, cyclohexylalanine shown as CHAla.

P10s-PADRE Plus Adjuvant

Compositions are provided in which P10s-PADRE is combined with an adjuvant in an injectable formulation. In some embodiments, the adjuvant is MONTANIDE™ ISA 51 VG adjuvant. MONTANIDE™ ISA 51 VG adjuvant displays a depot effect when used in humans. In some embodiments, other adjuvants which provide a depot effect are used. In some embodiments, other adjuvants which do not provide a depot effect are used. In some embodiments, the adjuvant is QS21 adjuvant (Agenus, Lexington Mass.). In some embodiments, the adjuvant is selected from the group of Montanide ISA Adjuvants (Seppic SA, Paris, France). In some embodiments, the adjuvant is selected from the group consisting of: Freund's Complete Adjuvant (FCA), Freund's Incomplete Adjuvant (FIA), one or more of Ribi's Adjuvants, Hunter's TiterMax, Aluminum Salt Adjuvants, Nitrocellulose-Adsorbed Protein, Liposome-entrapped antigen such as nondegradable ethylene-vinyl acetate copolymer-entrapped antigen, and degradable polymer-entrapped antigen including those using biodegradable, biocompatible such as poly(DL-lactide-co-glycolide) polymers and Gerbu Adjuvant. In some embodiments, the adjuvant is selected from the group consisting of: AddaVax™ adjuvant, Alhydrogel 2%, IFA, c-di-AMP VacciGrade™ adjuvant, c-di-GMP VacciGrade™ adjuvant, Flagellin FliC VacciGrade™ adjuvant, Gardiquimod VacciGrade™ adjuvant, Imiquimod VacciGrade™ adjuvant, MPLA-SM VacciGrade™ adjuvant, MPLA Synthetic VacciGrade™ adjuvant, N-Glycolyl-MDP VacciGrade™ adjuvant, ODN 1585 VacciGrade™ adjuvant, ODN 1826 VacciGrade™ adjuvant, ODN 2006 Vaccigrade™ adjuvant, ODN 2395 VacciGrade™ adjuvant, Pam3CSK4 VacciGrade™ adjuvant, Poly(I:C) (HMW) VacciGrade™ adjuvant, R848 VacciGrade™ adjuvant, and TDB VacciGrade™ adjuvant.

In some embodiments, adjuvants that have a natural depot effect may be selected and used. In some embodiments, adjuvants that do not have a natural depot effect may be selected and used. In some embodiments, adjuvants may be formulated to create or increase a depot effect.

P10s Variants

Multiple antigen peptide (MAP) forms of P10s may have repeating P10s units, for example, 4, 5, 6, 7, 8, 9, 10 or more P10s peptide repeats. Such MAP forms of CMPs are particularly useful to induce IgM immune responses.

P10s may be provided as a variant. The 12 amino acid sequence of P10s may be modified to form a fragment of P10s by deletion of up one to four of the last four residues ($P10s_{1-11}$, $P10s_{1-10}$, $P10s_{1-9}$, $P10s_{1-8}$). The 12 amino acid sequence of P10s may be modified by the addition of 1-3 N-terminal residues to form N-terminally extended P10s variants: $P10s_{1+1-12}$, $P10s_{2+1-12}$, and $P10s_{3+1-12}$. The N-terminally extended P10s variants ($P10s_{1+1-12}$, $P10s_{2+1-12}$, and $P10s_{3+1-12}$) may be truncated, e.g. $P10s_{1+1-12}$ may be truncated to produce $P10s_{1+1-11}$, $P10s_{1+1-10}$, $P10s_{1+1-9}$, $P10s_{1+1-8}$; $P10s_{2+1-12}$ may be truncated to produce $P10s_{2+1-11}$, $P10s_{2+1-10}$, $P10s_{2+1-9}$, $P10s_{2+1-8}$; $P10s_{3+1-12}$ may be truncated to produce $P10s_{3+1-11}$, $P10s_{3+1-10}$, $P10s_{3+1-9}$, and $P10s_{3+1-8}$. The N-terminally extended P10s variants having a single added residue at the N terminal preferably has a Valine residue at their N terminus. The N-terminally extended P10s variants having two added residues at the N terminal preferably have Valine-Valine residues at their N terminus. The N-terminally extended P10s variants having three added residues at the N terminal preferably have Glycine-Valine-Valine residues at their N terminus. P10s and each of these variants may be modified at $P10s_{1-3}$. $P10s$ has at positions 1-3, i.e. $P10s_{1-3}$, the WRY motif. In some variants $P10s_{1-3}$ of P10s ($P10s_{1-12}$) may be substituted with an YRY, YPY or WPY motif forming $P10s_{1-12Y1}$, $P10s_{1-12Y1P2}$, $P10s_{1-12P2}$. Other variants may have similar modifications at $P10s_{1-3}$. For example, like $P10s_{1-12}$ fragments ($P10s_{1-11}$, $P10s_{1-10}$, $P10s_{1-9}$, $P10s_{1-8}$), fragments may comprise a YRY, YPY or WPY motif at positions 1-3. $P10s_{1-12Y1}$, $P10s_{1-12Y1P2}$, $P10s_{1-12P2}$ may also be provided as truncated forms, i.e. $P10s_{1-11Y1}$, $P10s_{1-11Y1P2}$, $P10s_{1-11P2}$, $P10s_{1-10Y1}$, $P10s_{1-10Y1P2}$, $P10s_{1-10P2}$, $P10s_{1-9Y1}$, $P10s_{1-9Y1P2}$, $P10s_{1-9P2}$, $P10s_{1-8Y1}$, $P10s_{1-8Y1P2}$, $P10s_{1-8P2}$, and $P10s_{1-8P2}$. $P10s_{1-12Y1}$, $P10s_{1-12Y1P2}$, $P10s_{1-12P2}$, $P10s_{1-11Y1}$, $P10s_{1-11Y1P2}$, $P10s_{1-11P2}$, $P10s_{1-10Y1}$, $P10s_{1-10Y1P2}$, $P10s_{1-10P2}$, $P10s_{1-9Y1}$, $P10s_{1-9Y1P1}$, $P10s_{1-9P2}$, $P10s_{1-8Y1}$, $P10s_{1-8Y1P2}$, and $P10s_{1-8P2}$ may be modified at the N terminus with 1, 2 or 3 added N terminal residues. $P10s_{1-12}$, $P10s_{1-11}$, $P10s_{1-10}$, $P10s_{1-9}$, $P10s_{1-8}$, $P10s_{1-12Y1}$, $P10s_{1-12Y1P2}$, $P10s_{1-9P2}$, $P10s_{1-8Y1}$, $P10s_{1-8Y1P2}$, $P10s_{1-11P2}$, $P10s_{1-10Y1}$, $P10s_{1-10Y1P2}$, $P10s_{1-10P2}$, $P10s_{1-9Y1}$, $P10s_{1-9Y1P2}$, $P10s_{1-9P2}$, $P10s_{1-8Y1}$, $P10s_{1-8Y1P2}$, and $P10s_{1-8P2}$. $P10s_{1-12Y1}$, $P10s_{1-12Y1P2}$, $P10s_{1-12P2}$, $P10s_{1-11Y1}$, $P10s_{1-11Y1P2}$, $P10s_{1-11P2}$, $P10s_{1-10Y1}$, $P10s_{1-10Y1P2}$, $P10s_{1-10P2}$, $P10s_{1-9Y1}$, $P10s_{1-9Y1P2}$, $P10s_{1-9P2}$, $P10s_{1-8Y1}$, $P10s_{1-8Y1P2}$, and $P10s_{1-8P2}$, can be modified to produce $P10s_{1+1-12}$, $P10s_{1+1-11}$, $P10s_{1+1-10}$, $P10s_{1+1-9}$, $P10s_{1+1-8}$, $P10s_{1+1-12Y1}$, $P10s_{1+1-12Y1P2}$, $P10s_{1+1-12P2}$, $P10s_{1+1-11Y1}$, $P10s_{1+1-11Y1P2}$, $P10s_{1+1-11P2}$, $P10s_{1+1-10Y1}$, $P10s_{1+1-10Y1P2}$, $P10s_{1+1-10P2}$, $P10s_{1+1-9Y1}$, $P10s_{1+1-9Y1P2}$, $P10s_{1+1-9P2}$, $P10s_{1+1-8Y1}$, $P10s_{1+1-8Y1P2}$, and $P10s_{1+1-8P2}$ by addition of 1 amino acid residue at the N terminus. In some embodiments, the one residue is a Valine. The addition of 2 amino acid residues at the N terminus produces $P10s_{2+1-12}$, $P10s_{2+1-11}$, $P10s_{2+1-10}$, $P10s_{2+1-9}$, $P10s_{2+1-8}$, $P10s_{2+1-12Y1}$, $P10s_{2+1-12Y1P2}$, $P10s_{2+1-12P2}$, $P10s_{2+1-11Y1}$, $P10s_{2+1-11Y1P2}$, $P10s_{2+1-11P2}$, $P10s_{2+1-10Y1}$, $P10s_{2+1-10Y1P2}$, $P10s_{2+1-10P2}$, $P10s_{2+1-9Y1}$, $P10s_{2+1-9Y1P2}$, $P10s_{2+1-9P2}$, $P10s_{2+1-8Y1}$, $P10s_{2+1-8Y1P2}$, and $P10s_{2+1-8P2}$. In some embodiments, the two residues are Valine-Valine. The addition of 3 amino acid residues at the N terminus produces $P10s_{3+1-12}$, $P10s_{3+1-11}$, $P10s_{3+1-10}$, $P10s_{3+1-9}$, $P10s_{3+1-8}$, $P10s_{3+1-12Y1}$, $P10s_{3+1-12Y1P2}$, $P10s_{3+1-12P2}$, $P10s_{3+1-11Y1}$, $P10s_{3+1-11Y1P2}$, $P10s_{3+1-11P2}$, $P10s_{3+1-10\ Y1}$, $P10s_{3+1-10Y1P2}$, $P10s_{3+1-10P2}$, $P10s_{3+1-9Y1}$, $P10s_{3+1-9Y1P2}$, $P10s_{+1-9P2}$, $P10s_{3+1-8Y1}$, $P10s_{3+1-8Y1P2}$, and $P10s_{3+1-8P2}$. In some embodiments, the three residues are Glycine-Valine-Valine. Glycine-Valine-Valine linked to the N terminal of P10s yields P10 (SEQ IN:2). In addition, each P10s variant may be further modified for produce additional P10s variants. P10s variants may include any of the variants having residues 4-12 set forth above having one to four deletions at residues 4-12. Further modifications may include any of the variants having residues 4-11 set forth above having one to four deletions at residues 4-11. Further modifications may include any of the variants having residues 4-10 set forth above having one to four deletions at residues 4-10. Further modifications may include any of the variants having residues 4-9 set forth above having one to four deletions at residues 4-9. Further modifications may include any of the variants having residues 4-8 set forth above having one to four deletions at residues 4-8. Further modifications may include any of the variants having residues 4-12 set forth above having one to four insertions at residues 4-12. Further modifications may include any of the variants having residues 4-11 set forth above having one to four insertions at residues 4-11. Further modifications may include any of the variants having residues 4-10 set forth above having four insertions at residues 4-10. Further modifications may include any of the variants having residues 4-9 set forth above having one to four insertions at residues 4-9. Further modifications may include any of the variants having residues 4-8 set forth above having one to four insertions at residues 4-8. Further modifications may include any of the variants having residues 4-12 set forth above having one to four substitutions at residues 4-12. Further modifications may include any of the variants having residues 4-11 set forth above having one to four substitutions at residues 4-11. Further modifications may include any of the variants having residues 4-10 set forth above having one to four substitutions at residues 4-10. Further modifications may include any of the variants having residues 4-9 set forth above having one to four substitutions at residues 4-9. Further modifications may include any of the variants having residues 4-8 set forth above having one to four substitutions at residues 4-8. Further modifications may include any of the variants having residues 4-12 set forth above having a combination of one to four deletions, insertions and substitutions at residues 4-12. Further modifications may include any of the variants having residues 4-11 set forth above having a combination of one to four deletions, insertions and substitutions at residues 4-11. Further modifications may include any of the variants having residues 4-10 set forth above having a combination of one to four deletions, insertions and substitutions at residues 4-10. Further modifications may include any of the variants having residues 4-9 set forth above having a combination of one to four deletions, insertions and substitutions at residues 4-9. Further modifications may include any of the variants having residues 4-8 set forth above having a combination of one to four deletions, insertions and substitutions at residues 4-8. In addition to these structural features, variants induce antibodies that bind to P10s. Multiple antigen peptide (MAP) forms of P10s variants may have repeating P10s variant units, for example, 4, 5, 6, 7, 8, 9, 10 or more P10s variant peptide repeats. Such MAP forms of CMPs are particularly useful to induce IgM immune responses.

P10s or P10s Variant Linked to CD4+ Helper Epitope

A peptide forms a complex with an MHC and this complex may be recognized by a particular T cell receptor. The interaction between the MHC/peptide and the T cell receptor results in signals between the cell expressing the MHC and the T cell expressing the T cell receptor. In the case of the MHC class II, the complex formed by the peptide and MHC class II complex interacts with T cell receptors of CD4+ helper T cells. Thus, a peptide which can form a complex with an MHC class II molecule that can be recognized as a complex by a T cell receptor of a CD4+ helper T cell is a CD4+ helper epitope.

Compositions are provided in which P10s and P10s variants are linked to a CD4+ helper epitope.

In some embodiments, the CD4+ T cell epitopes are derived from the universal HLA-DR epitope PADRE. PADRE peptide forms complexes with at least 15 of the 16 most common types of HLA-DR. PADRE peptide dAla-Lys-CHAla-Val-Ala-Ala-Trp-Thr-Leu-Lys-Ala-Ala-dAla, discussed above, is an example of a universal CD4+ helper epitope. Since humans have at least one DR and PADRE binds to many of its types, PADRE has a high likelihood of being effective in most humans. Another example of a PADRE peptide is KXVAAWTLKA in which X is cyclohexylalanine (SEQ ID NO:3). Another example of a PADRE peptide is AKXVAAWTLKAA in which X is cyclohexylalanine (SEQ ID NO:4). Another example of a PADRE peptide is AKXVAAWTLKAAA in which X is cyclohexylalanine (SEQ ID NO:5).

PADRE peptides and other universal CD4+ helper epitopes are widely referred to by those skilled in the art (Alexander, J, delGuercio, M F, Maewal, A, Qiao L, Fikes Chestnut R W, Paulson J, Bundle D R, DeFrees S, and Sette A, Linear PADRE T Helper Epitope and Carbohydrate B Cell Epitope Conjugates Induce Specific High Titer IgG Antibody Responses, J. Immunol, 2000 Feb. 1, 164(3):1625-33; Wei J, Gao W, Wu J, Meng K, Zhang J, Chen J, Miao Y. Dendritic Cells Expressing a Combined PADRE/MUC4-Derived Polyepitope DNA Vaccine Induce Multiple Cytotoxic T-Cell Responses. Cancer Biother Radiopharm 2008, 23:121-8; Bargieri D Y, Rosa D S, Lasaro M A, Ferreira L C, Soares I S, Rodrigues M M. Adjuvant requirement for successful immunization with recombinant derivatives of *Plasmodium vivax* merozoite surface protein-1 delivered via the intranasal route. Mem Inst Oswaldo Cruz 2007, 102: 313-7; Rosa D S, Iwai L K, Tzelepis F, Bargieri D Y, Medeiros M A, Soares I S, Sidney J, Sette A, Kalil J, Mello L E, Cunha-Neto E, Rodrigues M M. Immunogenicity of a recombinant protein containing the *Plasmodium vivax* vaccine candidate MSP1(19) and two human CD4+ T-cell epitopes administered to non-human primates (*Callithrix jacchus jacchus*). Microbes Infect 2006, 8:2130-7; Zhang X, Issagholian A, Berg E A, Fishman J B, Nesburn A B, BenMohamed L. Th-cytotoxic T-lymphocyte chimeric epitopes extended by Nepsilon-palmitoyl lysines induce herpes simplex virus type 1-specific effector CD8+ Tel responses and protect against ocular infection. J Virol 2005; 79:15289-301 and Agadjanyan M G, Ghochikyan A, Petrushina I, Vasilevko V, Movsesyan N, Mkrtichyan M, Saing T, Cribbs D H. Prototype Alzheimer's disease vaccine using the immunodominant B cell epitope from beta-amyloid and promiscuous T cell epitope pan HLA DR-binding peptide. J Immunol 2005; 174:1580-6). Universal CD4+ helper epitopes, such as PADRE and others are disclosed in U.S. Pat. No. 5,736,142 issued Apr. 7, 1998 to Sette, et al.; U.S. Pat. No. 6,413,935 issued Jul. 2, 2002 to Sette, et al.; and U.S. Pat. No. 7,202,351 issued Apr. 10, 2007 to Sette, et al. Other peptides reported to bind to several DR types include those described in Busch et al., Int. Immunol. 2, 443-451 (1990); Panina-Bordignon et al., Eur. J. Immunol. 19, 2237-2242 (1989); Sinigaglia et al., Nature 336, 778-780 (1988); O'Sullivan et al., J. Immunol. 147, 2663-2669 (1991) Roache et al., J. Immunol. 144, 1849-1856 (1991); and Hill et al., J. Immunol. 147, 189-197 (1991). Additionally, U.S. Pat. No. 6,413,517 issued Jul. 2, 2002 to Sette, et al. refers to the identification of broadly reactive DR restricted epitopes.

In some embodiments P10s or a P10s variant is linked to the CD4+ T cell epitope keyhole limpet hemocyananin.

In some embodiments, P10s or a P10s variant is linked a CD4+ T cell epitope derived from tetanus toxin (Renard V, Sonderbye L, Ebbehoj K, Rasmussen P B, Gregorius K, Gottschalk T, Mouritsen S, Gautam A, Leach DR. HER-2 DNA and protein vaccines containing potent Th cell epitopes induce distinct protective and therapeutic antitumor responses in HER-2 transgenic mice. J Immunol 2003; 171:1588-95; Moro M, Cecconi V, Martinoli C, Dallegno E, Giabbai B, Degano M, Glaichenhaus N, Protti M P, Dellabona P, Casorati G. Generation of functional HLA-DR*1101 tetramers receptive for loading with pathogen- or tumour-derived synthetic peptides. BMC Immunol 2005; 6:24; BenMohamed L, Krishnan R, Longmate J, Auge C, Low L, Primus J, Diamond D J. Induction of CTL response by a minimal epitope vaccine in HLA A*0201/DR1 transgenic mice: dependence on HLA class II restricted T(H) response. Hum Immunol 2000; 61:764-79; and James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). HLA-DRB1*0401—15 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). HLA-DRB1*0701—9 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). HLA-DRB1*1501—7 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). HLA-DRB5*0101—8 different Tetanus Toxoid peptides (James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301).

In some embodiments, the CD4+ T cell epitope linked to P10s or a P10s variant may be derived from Influenza hemagluttinin (Mom M, Cecconi V, Martinoli C, Dallegno E, Giabbai B, Degano M, Glaichenhaus N, Protti M P, Dellabona P, Casorati G. Generation of functional HLA-DR*1101 tetramers receptive for loading with pathogen- or tumour-derived synthetic peptides. BMC Immunol 2005; 6:24).

In some embodiments, the CD4+ T cell epitope linked to P10s or a P10s variant may be derived from Hepatitis B surface antigen (HBsAg) (Litjens N H, Huisman M, Baan C C, van Druningen C J, Betjes M G. Hepatitis B vaccine-specific CD4(+) T cells can be detected and characterized at the single cell level: limited usefulness of dendritic cells as signal enhancers. J Immunol Methods 2008; 330:1-11).

In some embodiments, the CD4+ T cell epitope linked to P10s or a P10s variant may be derived from outer membrane proteins (OMPs) of bacterial pathogens (such as *Anaplasma marginals*) (Macmillan H, Norimine J, Brayton K A, Palmer G H, Brown W C. Physical linkage of naturally complexed bacterial outer membrane proteins enhances immunogenicity. Infect Immun 2008; 76:1223-9). In some embodiments SEQ ID NO:2 is linked to an epitope derived from outer membrane proteins (OMPs) of bacterial pathogens.

In some embodiments, the CD4+ T cell epitope linked to P10s or a P10s variant may be derived from the VP1 capsid protein from enterovirus 71 (EV71) strain 41 (Wei Foo D G, Macary P A, Alonso S, Poh C L. Identification of Human CD4(+) T-Cell Epitopes on the VP1 Capsid Protein of Enterovirus 71. Viral Immunol 2008).

In some embodiments, the CD4+ T cell epitope linked to P10s or a P10s variant may be derived from EBV BMLF1 (Schlienger K, Craighead N, Lee K P, Levine B L, June C H. Efficient priming of protein antigen-specific human CD4 (+) T cells by monocyte-derived dendritic cells. Blood 2000; 96:3490-8; Neidhart J, Allen K O, Barlow D L, Carpenter M, Shaw D R, Triozzi P L, Conry R M. Immunization of colorectal cancer patients with recombinant baculovirus-derived KSA (Ep-CAM) formulated with monophosphoryl lipid A in liposomal emulsion, with and without granulocyte-macrophage colony-stimulating factor. Vaccine 2004; 22:773-80; Piriou E R, van Dort K, Nanlohy N M, van Oers M H, Miedema F, van Baarle D. Novel method for detection of virus-specific CD4+ T cells indicates a decreased EBV-specific CD4+ T cell response in untreated HIV-infected subjects. Eur J Immunol 2005; 35:796-805; Heller K N, Upshaw J, Seyoum B, Zebroski H, Munz C. Distinct memory CD4+ T-cell subsets mediate immune recognition of Epstein Barr virus nuclear antigen 1 in healthy virus carriers. Blood 2007; 109:1138-46).

In some embodiments, the CD4+ T cell epitope linked to P10s or a P10s variant may be derived from EBV LMPI (Kobayashi H, Nagato T, Takahara M, Sato K, Kimura S, Aoki N, Azumi M, Tateno M, Harabuchi Y, Celis E. Induction of EBV-latent membrane protein 1-specific MHC class restricted T-cell responses against natural killer lymphoma cells. Cancer Res 2008; 68:901-8).

In some embodiments, the CD4+ T cell epitope linked to P10s or a P10s variant may be derived from HIV p2437, (Pajot A, Schnuriger A, Moris A, Rodallec A, Ojcius D M, Autran B, Lemonnier F A, Lone Y C. The Th1 immune response against HIV-1 Gag p24-derived peptides in mice expressing HLA-A02.01 and HLA-DRI. Eur J Immunol 2007; 37:2635-44).

In some embodiments, the CD4+ T cell epitope linked to P10s or a P10s variant may be derived from Adenovirus hexon protein (Leen A M, Christin A, Khalil M, Weiss H, Gee A P, Brenner M K, Heslop H E, Rooney C M, Bollard C M. Identification of hexon-specific CD4 and CD8 T-cell epitopes for vaccine and immunotherapy. J Viral 2008; 82:546-54).

In some embodiments P10s or P10s variant is linked to an epitope derived from a vaccinia protein. There are >30 identified CD4+ T cell epitopes for multiple MHC-II haplotypes, Vaccinia virus proteins (Calvo-Calle J M, Strug I, Nastke M D, Baker S P, Stem L J. Human CD4+ T cell epitopes from vaccinia virus induced by vaccination or infection. PLoS Pathog 2007; 3:1511-29) and >25 identified CD4+ T cell epitopes for multiple MHC-II haplotypes from 24 different vaccinia proteins.

In some embodiments P10s or P10s variant is linked to an epitope derived from heat shock protein. The CD4+ T cell epitopes derived from heat shock protein (Liu D W, Tsao Y P, Kung J T, Ding Y A, Sytwu H K, Xiao X, Chen S L. Recombinant adeno-associated virus expressing human papillomavirus type 16 E7 peptide DNA fused with heat shock protein DNA as a potential vaccine for cervical cancer. J Virol 2000; 74:2888-94.)

In some embodiments P10s or P10s variant is linked to is linked to an epitope derived from the Fc portion of IgG. In some embodiments, the CD4+ T cell epitopes are derived from the Fc portion of IgG (You Z, Huang X F, Hester J, Rollins L, Rooney C, Chen S Y. Induction of vigorous helper and cytotoxic T cell as well as B cell responses by dendritic cells expressing a modified antigen targeting receptor-mediated internalization pathway. J Immunol 2000; 165:4581-91).

In some embodiments P10s or P10s variant is linked to an epitope derived from lysosome-associated membrane protein. In some embodiments, the CD4+ T cell epitopes are derived from lysosome-associated membrane protein (Su Z, Vieweg J, Weizer A Z, Dahm P, Yancey D, Turaga V, Higgins J, Boczkowski D, Gilboa E, Dannull J. Enhanced induction of telomerase-specific CD4(+) T cells using dendritic cells transfected with RNA encoding a chimeric gene product. Cancer Res 2002; 62:5041-8).

A sample of HLA haplotypes as well as representative CD4+ T cell epitopes for the indicated HLA molecule include, but are not limited to, the following:

HLA-DR*1101—Tetanus Toxoid peptide residues 829-844, Hemagglutinin peptide residues 306-318 (Moro M, Cecconi V, Martinoli C, Dallegno E, Giabbai B, Degano M, Glaichenhaus N, Protti M P, Dellabona P, Casorati G. Generation of functional HLA-DR*1101 tetramers receptive for loading with pathogen- or tumour-derived synthetic peptides. BMC Immunol 2005; 6:24.) In some embodiments P10s or P10s variant is linked to tetanus toxin peptide residues 829-844 or Hemagglutinin peptide residues 306-318.

HLA-DRB1*0101 (DR1)—Tetanus Toxoid peptide residues 639-652, 830-843 or 947-967 and 14 other tetanus toxoid peptides (BenMohamed L, Krishnan R, Longmate J, Auge C, Low L, Primus J, Diamond D J. Induction of CTL response by a minimal epitope vaccine in HLA A*0201/DR1 transgenic mice: dependence on HLA class II restricted T(H) response. Hum Immunol 2000; 61:764-79; and James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). In some embodiments P10s or P10s variant is linked to tetanus toxin peptide residues 639-652, 830-843 or 947-967.

In some embodiments P10s or P10s variant is linked to EV71 VP1 residues 145-159 or 247-261. HLA-DRB1*0301—EV71 VP1 residues 145-159 or 247-261 and 5 different tetanus toxoid peptides (Wei Foo D G, Macary P A, Alonso S, Poh C L. Identification of Human CD4(+) T-Cell Epitopes on the VP1 Capsid Protein of Enterovirus 71. Viral Immunol 2008; and James E A, Bui J, Berger D, Huston L, Roti M, Kwok W W. Tetramer-guided epitope mapping reveals broad, individualized repertoires of tetanus toxin-specific CD4+ T cells and suggests HLA-based differences in epitope recognition. Int Immunol 2007; 19:1291-301). HLA-DRB1*0405—EV71 VP1 residues 145-159 or 247-261 (Wei Foo D G, Macary P A, Alonso S, Poh C L. Identification of Human CD4(+) T-Cell Epitopes on the VP1 Capsid Protein of Enterovirus 71. Viral Immunol 2008). HLA-DRB1*1301—EV71 VPI residues 145-159 or 247-261 (Wei Foo D G, Macary P A, Alonso S, Poh C L. Identification of Human CD4(+) T-Cell Epitopes on the VP 1 Capsid Protein of Enterovirus 71. Viral Immunol 2008).

In some embodiments P10s or P10s variant is linked to Epstein Barr virus (EBV) latent membrane protein 1 (LMP1) residues 159-175.HLA-DR9—Epstein Barr virus (EBV) latent membrane protein 1 (LMP1) residues 159-175 (Kobayashi H, Nagato T, Takahara M, Sato K, Kimura S, Aoki N, Azumi M, Tateno M, Harabuchi Y, Celis E. Induction of EBV-latent membrane protein 1-specific MHC class II-restricted T-cell responses against natural killer lymphoma cells. Cancer Res 2008; 68:901-8). HLA-DR53 EBV LMP1 residues 159-175 (Kobayashi H, Nagato T, Takahara M, Sato K, Kimura S, Aoki N, Azumi M, Tateno M, Harabuchi Y, Celis E. Induction of EBV-latent membrane protein 1-specific MHC class II-restricted T-cell responses against natural killer lymphoma cells. Cancer Res 2008; 68:901-8). HLA-DR15 EBV LMP1 residues 159-175 (Kobayashi H, Nagato T, Takahara M, Sato K, Kimura S, Aoki N, Azumi M, Tateno M, Harabuchi Y, Celis E. Induction of EBV-latent membrane protein 1-specific MHC class II-restricted T-cell responses against natural killer lymphoma cells. Cancer Res 2008; 68:901-8).

The P10s or P10s variant may be linked to the CD4+ T cell epitope by a peptide bond. In some embodiments, P10s or P10s variant is covalently linked to the CD4+ T cell epitope by a non-peptide bond.

In some embodiments, compositions are provided in which P10s is linked to a CD4+ helper epitope selected from the group: dAla-Lys-ChAla-Val-Ala-Ala-Trp-Thr-Leu-Lys-Ala-Ala-dAla-$NH_2$; dAla-Lys-ChAla-Val-Ala-Ala-Trp-Thr-Leu-Lys-Ala-Ala-dAla; dAla-Lys-ChAla-Val-Ala-Ala-Trp-Thr-Leu-Lys-Ala-Ala-dAla wherein the N terminus is not modified and the C terminus is modified; dAla-Lys-ChAla-Val-Ala-Ala-Trp-Thr-Leu-Lys-Ala-Ala-dAla wherein the N terminus is not modified and the C terminus is not modified, dAla-Lys-ChAla-Val-Ala-Ala-Trp-Thr-Leu-Lys-Ala-Ala-dAla wherein the N terminus is not modified and the C terminus is not modified, dAla-Lys-ChAla-Val-Ala-Ala-Trp-Thr-Leu-Lys-Ala-Ala-dAla wherein the N terminus is acetylated and the C terminus is amidated; dAla-Lys-ChAla-Val-Ala-Ala-Trp-Thr-Leu-Lys-Ala-Ala-dAla wherein the N terminus is not acetylated and the C terminus is amidated; dAla-Lys-ChAla-Val-Ala-Ala-Trp-Thr-Leu-Lys-Ala-Ala-dAla wherein the N terminus is not acetylated and the C terminus is not amidated; and dAla-Lys-ChAla-Val-Ala-Ala-Trp-Thr-Leu-Lys-Ala-Ala-dAla, wherein the N terminus is acetylated and the C terminus is not amidated; SEQ ID NO:3; SEQ ID NO:4; SEQ ID NO:5. In some embodiments, compositions are provided in which P10s is linked to a CD4+ helper epitope selected from the group: keyhole limpet hemocyananin; a CD4+ T cell epitope derived from tetanus toxin; a CD4+ T cell epitope derived from Influenza hemagluttinin; a CD4+ T cell epitope derived from Hepatitis B surface antigen (HBsAg); a CD4+ T cell epitope derived from outer membrane proteins (OMPs) of bacterial pathogens (such as *Anaplasma marginals*); a CD4+ T cell epitope derived from the VP1 capsid protein from enterovirus 71 (EV71) strain 41; a CD4+ T cell epitope derived from EBV BMLF1; a CD4+ T cell epitope derived from EBV LMPI; a CD4+ T cell epitope derived from HIV p2437; a CD4+ T cell epitope derived from Adenovirus hexon protein; a CD4+ T cell epitope derived from a vaccinia protein; a CD4+ T cell epitope derived from heat shock protein; a CD4+ T cell epitope derived from the Fc portion of IgG; a CD4+ T cell epitope derived from lysosome-associated membrane protein; In a CD4+ T cell epitope derived from lysosome-associated membrane protein. In some embodiments, the CD4+ helper epitope is selected from the group: tetanus toxin peptide residues 829-844; Hemagglutinin peptide residues 306-318; tetanus toxin peptide residues 639-652 or 830-843 or 947-967; EV71 VP1 residues 145-159 or 247-261; and Epstein Barr virus (EBV) latent membrane protein 1 (LMP1) residues 159-175. In some embodiments, such compositions in which P10s is linked to such CD4+ helper epitope, the attached P10s and CD4+ helper epitope compound is combined with an adjuvant in an injectable formulation, wherein the adjuvant is selected from MONTANIDE™ ISA 51 VG adjuvant, QS21 adjuvant, a different Montanide ISA adjuvant; Freund's Complete Adjuvant (FCA), Freund's Incomplete Adjuvant (FIA), one or more of Ribi's Adjuvants, Hunter's TiterMax, Aluminum Salt Adjuvants, Nitrocellulose-Adsorbed Protein, Liposome-entrapped antigen such as nondegradable ethylene-vinyl acetate copolymer-entrapped antigen, and degradable polymer-entrapped antigen including those using biodegradable, biocompatible such as poly(DL-lactide-co-glycolide) polymers; Gerbu Adjuvant; AddaVax™ adjuvant, Alhydrogel 2%, IFA, c-di-AMP VacciGrade™ adjuvant, c-di-GMP VacciGrade™ adjuvant, Flagellin FliC VacciGrade™ adjuvant, Gardiquimod VacciGrade™ adjuvant, Imiquimod VacciGrade™ adjuvant, MPLA-SM VacciGrade™ adjuvant, MPLA Synthetic VacciGrade™ adjuvant, N-Glycolyl-MDP VacciGrade™ adjuvant, ODN 1585 VacciGrade™ adjuvant, ODN 1826 VacciGrade™ adjuvant, ODN 2006 Vaccigrade™ adjuvant, ODN 2395 VacciGrade™ adjuvant, Pam3CSK4 VacciGrade™ adjuvant, Poly(I:C) (HMW) VacciGrade™ adjuvant, R848 VacciGrade™ adjuvant, and TDB VacciGrade™ adjuvant.

In some embodiments, compositions are provided in which a P10s variant is linked to a CD4+ helper epitope selected from the group: dAla-Lys-ChAla-Val-Ala-Ala-Trp-Thr-Leu-Lys-Ala-Ala-dAla-$NH_2$; dAla-Lys-ChAla-Val-Ala-Ala-Trp-Thr-Leu-Lys-Ala-Ala-dAla; dAla-Lys-ChAla-Val-Ala-Ala-Trp-Thr-Leu-Lys-Ala-Ala-dAla wherein the N terminus is not modified and the C terminus is modified; dAla-Lys-ChAla-Val-Ala-Ala-Trp-Thr-Leu-Lys-Ala-Ala-dAla wherein the N terminus is not modified and the C terminus is not modified, dAla-Lys-ChAla-Val-Ala-Ala-Trp-Thr-Leu-Lys-Ala-Ala-dAla wherein the N terminus is not modified and the C terminus is not modified, dAla-Lys-ChAla-Val-Ala-Ala-Trp-Thr-Leu-Lys-Ala-Ala-dAla wherein the N terminus is acetylated and the C terminus is amidated; dAla-Lys-ChAla-Val-Ala-Ala-Trp-Thr-Leu-Lys-Ala-Ala-dAla wherein the N terminus is not acetylated and the C terminus is amidated; dAla-Lys-ChAla-Val-Ala-Ala-Trp-Thr-Leu-Lys-Ala-Ala-dAla wherein the N terminus is not acetylated and the C terminus is not amidated; dAla-Lys-ChAla-Val-Ala-Ala-Trp-Thr-Leu-Lys-Ala-Ala-dAla wherein the N terminus is acetylated and the C terminus is not amidated; SEQ ID NO:3; SEQ ID NO:4; and SEQ ID NO:5. In some embodiments, compositions are provided in which P10s is linked to a CD4+ helper epitope selected from the group: keyhole limpet hemocyananin; a CD4+ T cell epitope derived from tetanus toxin; a CD4+ T cell epitope derived from Influenza hemagluttinin; a CD4+ T cell epitope derived from Hepatitis B surface antigen (HBsAg); a CD4+ T cell epitope derived from outer membrane proteins (OMPs) of bacterial pathogens (such as *Anaplasma marginals*); a CD4+ T cell epitope derived from the VP1 capsid protein from enterovirus 71 (EV71) strain 41; a CD4+ T cell epitope derived from EBV BMLF1; a CD4+ T cell epitope derived from EBV LMPI; a CD4+ T cell epitope derived from HIV p2437; a CD4+ T cell epitope derived from Adenovirus hexon protein; a CD4+ T cell epitope derived from a vaccinia protein; a CD4+ T cell epitope derived from heat shock protein; a CD4+ T cell epitope derived from the Fc portion of IgG; a CD4+ T cell epitope derived from lysosome-associated membrane protein; In a CD4+ T cell epitope derived from lysosome-associated membrane protein. In some embodiments, the CD4+ helper epitope is selected from the group: tetanus toxin peptide residues 829-844; Hemagglutinin peptide residues 306-318; tetanus toxin peptide residues 639-652 or 830-843 or 947-967; EV71 VP1 residues 145-159 or 247-261; and Epstein Barr virus (EBV) latent membrane protein 1 (LMP1) residues 159-175. In some embodiments, such compositions in which a P10s variant is linked to such CD4+ helper epitope, the attached P10s and CD4+ helper epitope compound is combined with an adjuvant in an injectable formulation, wherein the adjuvant is selected from MONTANIDE™ ISA 51 VG adjuvant, QS21 adjuvant, a different Montanide ISA adjuvant; Freund's Complete Adjuvant (FCA), Freund's Incomplete Adjuvant (FIA), one or more of Ribi's Adjuvants, Hunter's TiterMax, Aluminum Salt Adjuvants, Nitrocellulose-Adsorbed Protein, Liposome-entrapped antigen such as nondegradable ethylene-vinyl acetate copolymer-entrapped antigen, and degradable polymer-entrapped antigen including those using biodegradable, biocompatible such as poly (DL-lactide-co-glycolide) polymers; Gerbu Adjuvant; AddaVax™ adjuvant, Alhydrogel 2%, IFA, c-di-AMP VacciGrade™ adjuvant, c-di-GMP VacciGrade™ adjuvant, Flagellin FliC VacciGrade™ adjuvant, Gardiquimod VacciGrade™ adjuvant, Imiquimod VacciGrade™ adjuvant, MPLA-SM VacciGrade™ adjuvant, MPLA Synthetic VacciGrade™ adjuvant, N-Glycolyl-MDP VacciGrade™ adjuvant, ODN 1585 VacciGrade™ adjuvant, ODN 1826 VacciGrade™ adjuvant, ODN 2006 Vaccigrade™ adjuvant, ODN 2395 VacciGrade™ adjuvant, Pam3CSK4 VacciGrade™ adjuvant, Poly(I:C) (HMW) VacciGrade™ adjuvant, R848 VacciGrade™ adjuvant, and TDB VacciGrade™ adjuvant.

Antibodies

Some embodiments of the invention relate to isolated antibodies which bind to P10s and/or P10s-PADRE. Such antibodies may be human antibodies. Such antibodies may be cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs.

Isolated antibodies may be produced by i) immunizing an human with P10s, P10s variant, P10s-PADRE, P10s+other CD4+ helper T cell epitope, P10s+other CD4+ helper T cell epitope, combinations thereof or such immunizing peptides in a composition further comprising an adjuvant, ii) isolating human B cells from the immunized individual, iii) identifying the B cell that produces antibodies that have a cytotoxic effect on tumor cells, iv) isolating/cloning the antibody encoding genes from the B cell and v) introducing the genes into cells that will produce the antibodies that have a cytotoxic effect on tumor cells. The antibody producing cells may be cultured under conditions to produce antibodies which can be isolated from the cell culture. Alternatively, ii) human B cells from the immunized individual isolated in step ii) and identified as human B cells that produces antibodies that have a cytotoxic effect on tumor cells as in step iii) may be cultured to expand populations of the B cell that will produce cultured B cells that produce antibodies that have a cytotoxic effect on tumor cells, or such B cells may be modified to form stable cells that can be cultured and that that will produce the antibodies that have a cytotoxic effect on tumor cells. The antibody producing cells may be cultured under conditions to produce antibodies which can be isolated from the cell culture.

Pluralities human antibodies that bind to P10s and/or P10s-PADRE and are cytotoxic to cultured cancer cells represented by human breast cell line MDA-231, which is a so called basel-like or triple negative tumor cell line, and HCC1954 cells, which are Her2+ cells and considered de novo resistant to select cancer fighting drugs may be produced by i) exposing an animal to with P10s, P10s variant, P10s-PADRE, P10s+other CD4+ helper T cell epitope, P10s+other CD4+ helper T cell epitope, combinations thereof or such immunizing in a composition further comprising an adjuvant, ii) preparing hybridomas from cells of the animal, and iii) identifying the hybridoma that produces antibodies, that bind to P10s and/or P10s-PADRE and are cytotoxic to cultured cancer cells represented by human breast cell lines line MDA-231, which is a so called basel-like or triple negative tumor cell line, and HCC1954 cells, which are Her2+ cells and considered de novo resistant to select cancer fighting drugs is identified. The selected hybridoma may be cultured to produce progeny that produce the antibody and/or its genetic material processed to isolate nucleic acid sequences that encode the antibody. The nucleic acid sequences that encode the antibody may then be inserted into an expression vector and introduced into a cell which can produce the antibodies. The nucleic acid sequences that encode the antibody may be used to produce nucleotide sequences that encode humanized antibodies, such nucleotide sequences are then inserted into an expression vector and introduced into a cell which can produce the humanized antibodies Antibodies refer to fragments of antibody, including but not limited to for example single chain antibodies, FAb fragments, and FAb$_2$ fragments, that specifically bind to P10s/P10s-PADRE. Antibodies include polyclonal and monoclonal antibodies as well as Fab fragments, F(ab)$_2$ fragments and other modifications and products of antibody engineering. Humanized, primatized and modified forms of antibodies to render them less immunogenic are antibodies according to the invention and may be used in the methods of the invention. Those having ordinary skill in the art can produce monoclonal antibodies which specifically bind to P10s using standard techniques and readily available starting materials. Such antibodies can be screened to determine if they possess the particularly useful functionality of the antibodies provided herein. The techniques for producing monoclonal antibodies are outlined in Harlow, E. and D. Lane, (1988) ANTIBODIES: A Laboratory Manual, Cold Spring Harbor Laboratory, Cold Spring Harbor N.Y., which is incorporated herein by reference, provide detailed guidance for the production of hybridomas and monoclonal antibodies which specifically bind to target proteins. Briefly, the immunogen is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the protein of interest, the hybridoma which produces them is cultured to produce a continuous supply of antigen specific antibodies. Techniques for engineering antibodies are described in U.S. Pat. No. 5,530,101, U.S. Pat. No. 5,585,089, U.S. Pat. No. 5,225,539, Winter and Millstein (1991) Nature 349:293, and Larrich and Fry (1991) Hum. Antibod. and Hybridomas 2:17, which are each incorporated herein by reference.

Antibodies may be formulated as unconjugated antibodies or may be conjugated to a drug, toxin or radioactive compound. Chemotherapeutics which may be conjugated to antibodies include cytotoxic and cytostatic drugs. Examples of chemotherapeutics include common cytotoxic or cytostatic drugs such as for example: methotrexate (amethopterin), doxorubicin (adrimycin), daunorubicin, cytosinarabinoside, etoposide, 5-4 fluorouracil, melphalan, chlorambucil, and other nitrogen mustards (e.g. cyclophosphamide), cis-platinum, vindesine (and other vinca alkaloids), mitomycin and bleomycin. Other chemotherapeutics include: purothionin (barley flour oligopeptide), macromomycin. 1,4-benzoquinone derivatives and trenimon as well as nitroimidazoles, metronidazole and misonidazole. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin. Examples of radionuclides useful as toxins in radiation therapy include: $^{47}$Sc, $^{67}$Cu, $^{90}$Y, $^{109}$Pd, $^{123}$I, $^{125}$I, $^{131}$I, $^{186}$Re, $^{188}$Re, $^{90}$Y, $^{199}$Au, $^{211}$At, $^{212}$Pb and $^{212}$Bi. Other radionuclides which have been used by those having ordinary skill in the art include: $^{32}$P, $^{33}$P, $^{71}$Ge, $^{109}$Pd, $^{77}$As, $^{103}$Pb, $^{105}$Rh, $^{111}$Ag, $^{119}$Sb, $^{121}$Sn, $^{131}$Cs, $^{143}$Pr, $^{161}$Tb, $^{177}$Ln, $^{191}$O, $^{193}$Mpt, $^{197}$Hg, all beta negative and/or auger emitters. Some preferred radionuclides include: $^{90}$Y, $^{131}$I, $^{211}$At, and $^{212}$Pb/$^{212}$B.

One having ordinary skill in the art may conjugate an antibody to a chemotherapeutic drug, toxin or radionuclide using well-known techniques. For example, Magerstadt, M. Antibody Conjugates and Malignant Disease. (1991) CRC Press, Boca Raton, USA, pp. 110-152) which is incorporated herein by reference, teaches the conjugation of various cytostatic drugs to amino acids of antibodies. Most of the chemotherapeutic agents currently in use in treating cancer possess functional groups that are amenable to chemical crosslinking directly with proteins. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to the single free amino group of an antibody. Homobifunctional succinimidyl esters, preferably with carbon chain spacers such as disuccinimidyl suberate (Pierce Co, Rockford, Ill.) may be used. In the event that a cleavable conjugated compound is required, the same protocol would be employed utilizing 3,3'-dithiobis (sulfosuccinimidylpropionate; Pierce Co.).

Combination Products and Kits

Compositions comprising components selected from the group consisting of: i) P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s, P10s variants, "P10s linked to other CD4⁺ helper T cell epitopes peptides", P10s variants linked to PADRE, "P10s variants linked to other CD4⁺ helper T cell epitopes peptides other than PADRE", P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4⁺ helper T cell epitopes peptides" plus MONTANIDE™ ISA 51 VG adjuvant, "P10s linked to other CD4⁺ helper T cell epitopes peptides" plus QS21 adjuvant, "P10s linked to other CD4⁺ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4⁺ helper T cell epitopes peptides other than PADRE" plus MONTANIDE™ ISA 51 VG adjuvant, "P10s variants linked to other CD4⁺ helper T cell epitopes peptides other than PADRE" plus QS21 adjuvant, "P10s variants linked to other CD4⁺ helper T cell epitopes peptides other than PADRE" plus an adjuvant other than MONTANIDE™ ISA 51 VG adjuvant or QS21 adjuvant, an unconjugated cytotoxic anti-P10s/P10s-PADRE antibody, an anti-P10s/P10s-PADRE antibody conjugated to a chemotherapeutic and an anti-P10s/P10s-PADRE antibody conjugated a radioactive compound may further comprise ii) a chemotherapeutic or radiotherapeutic. Kits may be provided that comprises i) a first container comprising a compositions having components selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s, P10s variants, P10s-PADRE, P10s linked to other CD4⁺ helper T cell epitopes peptides other than PADRE, P10s variants linked to PADRE, P10s variants linked to other CD4⁺ helper T cell epitopes peptides other than PADRE, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4⁺ helper T cell epitopes peptides" plus MONTANIDE™ ISA 51 VG adjuvant, "P10s linked to other CD4⁺ helper T cell epitopes peptides" plus QS21 adjuvant, "P10s linked to other CD4⁺ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4⁺ helper T cell epitopes peptides other than PADRE" plus MONTANIDE™ ISA 51 VG adjuvant, "P10s variants linked to other CD4⁺ helper T cell epitopes peptides other than PADRE" plus QS21 adjuvant, "P10s variants linked to other CD4⁺ helper T cell epitopes peptides other than PADRE" plus an adjuvant other than MONTANIDE™ ISA 51 VG adjuvant or QS21 adjuvant, an unconjugated cytotoxic anti-P10s/P10s-PADRE antibody, an anti-P10s/P10s-PADRE antibody conjugated to a chemotherapeutic and an anti-P10s/P10s-PADRE antibody conjugated to a radioactive compound and a second container that comprises a chemotherapeutic or radiotherapeutic.

Isolated NK Cells

Isolated NK cells activated by a compositions selected from the group consisting of: P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4⁺ helper T cell epitopes peptides" plus MONTANIDE™ ISA 51 VG adjuvant, "P10s linked to other CD4⁺ helper T cell epitopes peptides" plus QS21 adjuvant, "P10s linked to other CD4⁺ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4⁺ helper T cell epitopes peptides other than PADRE" plus MONTANIDE™ ISA 51 VG adjuvant, "P10s variants linked to other CD4⁺ helper T cell epitopes peptides other than PADRE" plus QS21 adjuvant, "P10s variants linked to other CD4⁺ helper T cell epitopes peptides other than PADRE" plus an adjuvant other than MONTANIDE™ ISA 51 VG adjuvant or QS21 adjuvant, may be used to treat immunized individuals.

The isolated NK cells may be prepared by i) isolating NK cells from a human who has been immunized with a compositions selected from the group consisting of: P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4⁺ helper T cell epitopes peptides" plus MONTANIDE™ ISA 51 VG adjuvant, "P10s linked to other CD4⁺ helper T cell epitopes peptides" plus QS21 adjuvant, "P10s linked to other CD4⁺ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4⁺ helper T cell epitopes peptides other than PADRE" plus MONTANIDE™ ISA 51 VG adjuvant, "P10s variants linked to other CD4⁺ helper T cell epitopes peptides other than PADRE" plus QS21 adjuvant, "P10s variants linked to other CD4⁺ helper T cell epitopes peptides other than PADRE" plus an adjuvant other than MONTANIDE™ ISA 51 VG adjuvant or QS21 adjuvant; ii) identifying the NK cell activated by a compositions selected from the group consisting of: P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, "P10s linked to other CD4$^+$ helper T cell epitopes peptides" plus MONTANIDE™ ISA 51 VG adjuvant, "P10s linked to other CD4$^+$ helper T cell epitopes peptides" plus QS21 adjuvant, "P10s linked to other CD4$^+$ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4$^+$ helper T cell epitopes peptides other than PADRE" plus MONTANIDE™ ISA 51 VG adjuvant, "P10s variants linked to other CD4$^+$ helper T cell epitopes peptides other than PADRE" plus QS21 adjuvant, "P10s variants linked to other CD4$^+$ helper T cell epitopes peptides other than PADRE" plus an adjuvant other than MONTANIDE™ ISA 51 VG adjuvant or QS21 adjuvant; and iii) expanding the population of identified NK cells.

The isolated NK cells may be prepared by isolating NK cells from a naïve or immunized human by i) exposing the NK cells to a compositions selected from the group consisting of: P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, P10s-PADRE plus MONTANIDE™ ISA 51 VG adjuvant, "P10s linked to other CD4$^+$ helper T cell epitopes peptides" plus MONTANIDE™ ISA 51 VG adjuvant, "P10s linked to other CD4$^+$ helper T cell epitopes peptides" plus QS21 adjuvant, "P10s linked to other CD4$^+$ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4$^+$ helper T cell epitopes peptides other than PADRE" plus MONTANIDE™ ISA 51 VG adjuvant, "P10s variants linked to other CD4$^+$ helper T cell epitopes peptides other than PADRE" plus QS21 adjuvant, "P10s variants linked to other CD4$^+$ helper T cell epitopes peptides other than PADRE" plus an adjuvant other than MONTANIDE™ ISA 51 VG adjuvant or QS21 adjuvant; ii) identifying the NK cell activated by a compositions selected from the group consisting of: P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, "P10s linked to other CD4$^+$ helper T cell epitopes peptides" plus MONTANIDE™ ISA 51 VG adjuvant, "P10s linked to other CD4$^+$ helper T cell epitopes peptides" plus QS21 adjuvant, "P10s linked to other CD4$^+$ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4$^+$ helper T cell epitopes peptides other than PADRE" plus MONTANIDE™ ISA 51 VG adjuvant, "P10s variants linked to other CD4$^+$ helper T cell epitopes peptides other than PADRE" plus QS21 adjuvant, "P10s variants linked to other CD4$^+$ helper T cell epitopes peptides other than PADRE" plus an adjuvant other than MONTANIDE™ ISA 51 VG adjuvant or QS21 adjuvant; and iii) expanding the population of identified NK cells.

The expanded population of NK cells may be administered to the patient to treat cancer or prevent occurrence recurrence in an individual identified as being at high risk.

Isolated Dendritic Cells

Isolated dendritic cells activated by a compositions selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4$^+$ helper T cell epitopes peptides" plus MONTANIDE™ ISA 51 VG adjuvant, "P10s linked to other CD4$^+$ helper T cell epitopes peptides" plus QS21 adjuvant, "P10s linked to other CD4$^+$ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4$^+$ helper T cell epitopes peptides other than PADRE" plus MONTANIDE™ ISA 51 VG adjuvant, "P10s variants linked to other CD4$^+$ helper T cell epitopes peptides other than PADRE" plus QS21 adjuvant, "P10s variants linked to other CD4$^+$ helper T cell epitopes peptides other than PADRE" plus an adjuvant other than MONTANIDE™ ISA 51 VG adjuvant or QS21 adjuvant are provided which may be useful to treat and prevent cancer.

The isolated dendritic cells may be prepared by i) isolating dendritic cells from a human who has been immunized with a compositions selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4+ helper T cell epitopes peptides" plus MONTANIDE™ ISA 51 VG adjuvant, "P10s linked to other CD4+ helper T cell epitopes peptides" plus QS21 adjuvant, "P10s linked to other CD4+ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4+ helper T cell epitopes peptides other than PADRE" plus MONTANIDE™ ISA 51 VG adjuvant, "P10s variants linked to other CD4+ helper T cell epitopes peptides other than PADRE" plus QS21 adjuvant, "P10s variants linked to other CD4+ helper T cell epitopes peptides other than PADRE" plus an adjuvant other than MONTANIDE™ ISA 51 VG adjuvant or QS21 adjuvant; ii) identifying a dendritic cell activated by a compositions selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4+ helper T cell epitopes peptides" plus MONTANIDE™ ISA 51 VG adjuvant, "P10s linked to other CD4+ helper T cell epitopes peptides" plus QS21 adjuvant, "P10s linked to other CD4+ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4+ helper T cell epitopes peptides other than PADRE" plus MONTANIDE™ ISA 51 VG adjuvant, "P10s variants linked to other CD4+ helper T cell epitopes peptides other than PADRE" plus QS21 adjuvant, "P10s variants linked to other CD4+ helper T cell epitopes peptides other than PADRE" plus an adjuvant other than MONTANIDE™ ISA 51 VG adjuvant or QS21 adjuvant; and iii) expanding the population of identified dendritic cells.

The isolated dendritic cells may be prepared by i) isolating dendritic cells from a naive human, ii) exposing the dendritic cells to a compositions selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4+ helper T cell epitopes peptides" plus MONTANIDE™ ISA 51 VG adjuvant, "P10s linked to other CD4+ helper T cell epitopes peptides" plus QS21 adjuvant, "P10s linked to other CD4+ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4+ helper T cell epitopes peptides other than PADRE" plus MONTANIDE™ ISA 51 VG adjuvant, "P10s variants linked to other CD4+ helper T cell epitopes peptides other than PADRE" plus QS21 adjuvant, "P10s variants linked to other CD4+ helper T cell epitopes peptides other than PADRE" plus an adjuvant other than MONTANIDE™ ISA 51 VG adjuvant or QS21 adjuvant; ii) identifying a dendritic cell activated by a compositions selected from the group consisting of: P10s-PADRE, P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, "P10s linked to other CD4+ helper T cell epitopes peptides" plus MONTANIDE™ ISA 51 VG adjuvant, "P10s linked to other CD4+ helper T cell epitopes peptides" plus QS21 adjuvant, "P10s linked to other CD4+ helper T cell epitopes peptides" plus an adjuvant other than MONTANIDE™ ISA 51 VG adjuvant or QS21 adjuvant, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4+ helper T cell epitopes peptides other than PADRE" plus MONTANIDE™ ISA 51 VG adjuvant, "P10s variants linked to other CD4+ helper T cell epitopes peptides other than PADRE" plus QS21 adjuvant, "P10s variants linked to other CD4+ helper T cell epitopes peptides other than PADRE" plus an adjuvant other than MONTANIDE™ ISA 51 VG adjuvant or QS21 adjuvant; and iii) expanding the population of identified dendritic cells.

Expanded population of dendritic cells may be administered to the patient to treat cancer or prevent occurrence/recurrence in an individual identified as being at high risk.

Cancers

An alphabetical list of cancer includes: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extra hepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary;

Cerebellar Astrocytoma, Childhood; Cerebral Astrocytoma/ Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macroglobulinemia; and Wilms' Tumor. Compositions and methods set forth herein may be useful to treat such types of cancer in an individual diagnosed with cancer or to prevent occurrence/recurrence of cancer in an individual identified as being as a high risk of cancer.

Among the cancers listed herein of cancers for which the invention may be used in treatment and prevention protocols, breast cancers, melanomas, ovarian cancers, prostate cancers, pancreatic cancers, lung cancers, colon cancers, head and neck cancers including mouth and esophageal, liver cancers, brain cancers and bone cancers are examples cancers that have solid tumors which are responsible for a majority of cancer deaths in the U.S. Breast cancers may be analyzed to determine whether they are Her$^+$, EGFRvIII$^+$ or Her$^+$ and EGFRvIII$^+$. In some embodiments, breast cancers are identified as Her$^+$, EGFRvIII$^+$ or Her$^+$ and EGFRvIII$^+$ prior to treatment.

Palliative treatment of metastatic disease, particularly those which causes pain and/or reduction in quality of life, is including among conditions for which the methods described herein are particularly useful.

Patients

Humans who have been diagnosed with cancer may be treated using methods and compositions described herein. Humans who have been identified as being at a high risk for cancer may be treated to prevent occurrence or recurrence of cancer using methods and compositions described herein.

Individual may be diagnosed as having cancer by standard techniques and methodologies. Such individuals may be treated using methods and compositions described herein. Individual diagnosed as having cancer include those who are first diagnosed with cancer and those who have been treated with surgery and/or chemotherapy and either have intractable disease, incomplete responses to treatment or who have been deemed cancer free and diagnosed as having a recurrence of cancer.

Individuals who are in high-risk groups for cancer include those who have been diagnosed with cancer that has been surgically removed or is currently in remission and/or those who are genetically linked to the disease, i.e. individuals who have been identified as genetically predisposed such as by genetic screening and/or family histories. Advancements in the understanding of genetics and developments in technology as well as epidemiology allow for the determination of probability and risk assessment an individual has for developing stomach or esophageal cancer. Using family health histories and/or genetic screening, it is possible to estimate the probability that a particular individual has for developing certain types of cancer. Those individuals that have been identified as being predisposed to developing a particular form of cancer can be immunized.

Individuals may be treated who have Stage I, II or III cancer. Individual with Stage 0, i.e. no detectable lymph node metastasis, may also be treated to prevent recurrence. In some embodiments, individuals who have Stage IV cancer may be treated.

Methods of Treating Cancer by Immunization

In some embodiments, individuals who have been diagnosed as having cancer are immunized with a composition comprising components selected from the group consisting of: P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, and P10s-PADRE. Typically, multiple doses are administered, for example an initial dose and 1, 2, 3, 4, 5, 6, 7 8, 9, or 10 boosts within year one. In some embodiments, following initial dose, boosts are given weeks 2, 3, and 7, weeks 2, 3, 7, and 19, or weeks 2 and 3 and then monthly for one, two three, four, five or six months.

In some embodiments, instead of using a composition comprising components selected from the group consisting of: P10s-PADRE plus MONTANIDE™ ISA 51 VG adjuvant, P10s-PADRE plus QS21 adjuvant, P10s-PADRE plus an adjuvant other than MONTANIDE™ ISA 51 VG adjuvant or QS21 adjuvant, and P10s-PADRE, individuals who have been diagnosed as having cancer are immunized with a composition comprising components selected from the group consisting of: P10s, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, P10s linked to a PADRE, P10s linked to a PADRE plus MONTANIDE™ ISA 51 VG adjuvant, P10s linked to a PADRE plus QS21 adjuvant, P10s linked to a PADRE plus an adjuvant other than MONTANIDE™ ISA 51 VG adjuvant or QS21 adjuvant, "P10s linked to other $CD4^+$ helper T cell epitopes peptides", "P10s linked to other $CD4^+$ helper T cell epitopes peptides" plus MONTANIDE™ ISA 51 VG adjuvant, "P10s linked to other $CD4^+$ helper T cell epitopes peptides" plus QS21 adjuvant, "P10s linked to other $CD4^+$ helper T cell epitopes peptides" plus an adjuvant other than MONTANIDE™ ISA 51 VG adjuvant or QS21 adjuvant, P10s variants linked to PADRE, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other $CD4^+$ helper T cell epitopes peptides other than PADRE", "P10s variants linked to other $CD4^+$ helper T cell epitopes peptides other than PADRE" plus MONTANIDE™ ISA 51 VG adjuvant, "P10s variants linked to other $CD4^+$ helper T cell epitopes peptides other than PADRE" plus QS21 adjuvant, "P10s variants linked to other $CD4^+$ helper T cell epitopes peptides other than PADRE" plus an adjuvant other than MONTANIDE™ ISA 51 VG adjuvant or QS21 adjuvant.

In some embodiments, individuals who have been diagnosed as having cancer are immunized as described herein are administered chemotherapy and/or radiation therapy in combination with the immunization described herein. In some embodiments, the chemotherapy and/or radiation therapy is administered concurrently with the immunization described herein. In some embodiments, the chemotherapy and/or radiation therapy is administered after initial immunization as described herein. In some embodiments, the chemotherapy and/or radiation therapy is administered after 1 or less, 2, 3, 4, 5, 6, 7, 8 or more weeks after initial immunization as described herein. Immunization may be useful to render the chemotherapy and/or radiation therapy more effective by lowering doses of chemotherapy and/or radiation needed for effective treatment, thereby reducing harmful side effects caused by chemotherapy and/or radiation. Immunization may be useful to render the chemotherapy and/or radiation therapy more effective by rendering cancer cells chemosensitive and/or radiosensitive thereby making chemotherapy and/or radiation therapy more effective.

In some embodiments, individuals who have radioresistant tumors may be treated by immunization to render the cancer radiosensitive. This is particularly useful in eliminating cancer stem cells and other radioresistant cancer cells. In some embodiments, radioresistant tumors may be the cause of pain to the afflicted individual and immunization in combination with radiation therapy may provide an effective means top shrink or eliminate tumors and reduce or eliminate pain caused by such tumors or reduce or eliminate other circumstances caused by such tumors which negatively impact quality of life. While such treatment may be palliative, the effect on quality of life can be profound. The immunization protocols in combination with radiation therapy may be useful to treat individual suffering from tumors in instances in which surgery is not indicated. Following immunization protocols in combination with radiation therapy tumor size and numbers may be reduced making surgery is a viable treatment option.

In some embodiments, individuals who have chemoresistant tumors may be treated by immunization to render the cancer chemosensitive. This is particularly useful in eliminating cancer stem cells and other chemoresistant cancer cells. In some embodiments, chemoresistant tumors may be the cause of pain to the afflicted individual and immunization in combination with chemotherapy may provide an effective means top shrink or eliminate tumors and reduce or eliminate pain caused by such tumors or reduce or eliminate other circumstances caused by such tumors which negatively impact quality of life. While such treatment may be palliative, the effect on quality of life can be profound. The immunization protocols in combination with chemotherapy may be useful to treat individual suffering from tumors in instances in which surgery is not indicated. Following immunization protocols in combination with chemotherapy tumor size and numbers may be reduced making surgery is a viable treatment option.

In some embodiments, individuals who have been treated with immunization following surgery, remission or identification of an individual in a high risk population due to genetic predisposition may be treated more effectively upon recurrence/occurrence of cancer. The immunization may result in subsequent cancer being more chemosensitive or radiosensitive, or otherwise lead to improved outcomes relative to outcomes of those not immunized.

Methods of Treating Cancer with Antibodies

In some embodiments, individuals who have been diagnosed as having cancer are administered isolated human antibodies as described herein. Typically, multiple doses are administered, for example an initial dose and 1, 2, 3, 4, 5, 6, 7 8, 9, or 10 follow-up doses within year one. In some embodiments, following initial dose, antibody is administered over one, two three, four, five or six months.

In some embodiments, individuals who have been diagnosed as having cancer are administered isolated human antibodies as described herein in combination with chemotherapy and/or radiation therapy. In some embodiments, the chemotherapy and/or radiation therapy is administered concurrently with the administration of isolated human antibodies. In some embodiments, the chemotherapy and/or radiation therapy is administered after initial administration of isolated human antibodies. In some embodiments, the chemotherapy and/or radiation therapy is administered after 1 or less, 2, 3, 4, 5, 6, 7, 8 or more weeks after initial administration of isolated human antibodies. Administration of isolated human antibodies may be useful to render the chemotherapy and/or radiation therapy more effective by lowering doses of chemotherapy and/or radiation needed for effective treatment, thereby reducing harmful side effects caused by chemotherapy and/or radiation. Administration of isolated human antibodies may be useful to render the chemotherapy and/or radiation therapy more effective by rendering cancer cells chemosensitive and/or radiosensitive thereby making chemotherapy and/or radiation therapy more effective.

In some embodiments, individuals who have radioresistant tumors may be treated by administration of isolated human antibodies to render the cancer radiosensitive. This is particularly useful in eliminating cancer stem cells and other radioresistant cancer cells. In some embodiments, radioresistant tumors may be the cause of pain to the afflicted individual and administration of isolated human antibodies in combination with radiation therapy may provide an effective means top shrink or eliminate tumors and reduce or eliminate pain caused by such tumors. While such treatment may be palliative, the effect on quality of life can be profound. The administration of isolated human antibodies in combination with radiation therapy may be useful to treat individual suffering from tumors in instances in which surgery is not indicated. Following administration of isolated human antibodies in combination with radiation therapy tumor size and numbers may be reduced making surgery is a viable treatment option.

In some embodiments, individuals who have chemoresistant tumors may be treated by administration of isolated human antibodies to render the cancer chemosensitive. This is particularly useful in eliminating cancer stem cells and other chemoresistant cancer cells. In some embodiments, chemoresistant tumors may be the cause of pain to the afflicted individual and immunization in combination with chemotherapy may provide an effective means top shrink or eliminate tumors and reduce or eliminate pain caused by such tumors. While such treatment may be palliative, the effect on quality of life can be profound. The administration of isolated human antibodies protocols in combination with chemotherapy may be useful to treat individual suffering from tumors in instances in which surgery is not indicated. Following administration of isolated human antibodies in combination with chemotherapy tumor size and numbers may be reduced making surgery is a viable treatment option.

In some embodiments, individuals who have been treated by administration of isolated human antibodies following surgery, remission or identification of an individual in a high risk population due to genetic predisposition may be treated more effectively upon recurrence/occurrence of cancer. The administration of isolated human antibodies may result in subsequent cancer being more chemosensitive or radiosensitive, or otherwise lead to improved outcomes relative to outcomes of those not immunized.

Methods of Treating Cancer with Isolated NK Cells

In some embodiments, individuals who have been diagnosed as having cancer are administered isolated NK cells as described herein. Such individuals have been immunized and the administration of expanded populations of NK cells activated by the vaccine may be effective to eliminate tumors.

In some embodiments, individuals who have been diagnosed as having cancer are administered isolated NK cells as described herein in combination with chemotherapy and/or radiation therapy. In some embodiments, the chemotherapy and/or radiation therapy is administered concurrently with the administration of NK cells. In some embodiments, the chemotherapy and/or radiation therapy is administered after initial administration of isolated NK cells. In some embodiments, the chemotherapy and/or radiation therapy is administered after 1 or less, 2, 3, 4, 5, 6, 7, 8 or more weeks after initial administration of isolated NK cells. Administration of isolated NK cells may be useful to render the chemotherapy and/or radiation therapy more effective by lowering doses of chemotherapy and/or radiation needed for effective treatment, thereby reducing harmful side effects caused by chemotherapy and/or radiation. Administration of isolated NK cells may be useful to render the chemotherapy and/or radiation therapy more effective by rendering cancer cells chemosensitive and/or radiosensitive thereby making chemotherapy and/or radiation therapy more effective.

Isolated NK cells may be administered in a coordinated manner with immunization boosts to maximize humoral immune responses which render tumor cells otherwise resistant to NK cells as susceptible to NK cells.

Isolated NK cells may be administered in a coordinated manner with administration of antibodies described herein as such antibodies may render tumor cells otherwise resistant to NK cells as susceptible to NK cells.

Methods of Treating Cancer with Isolated Dendritic Cells

In some embodiments, individuals who have been diagnosed as having cancer are administered isolated dendritic cells as described herein. In some embodiments, individuals who have been diagnosed as having cancer are administered isolated dendritic cells as described herein in combination with chemotherapy and/or radiation therapy. In some embodiments, the chemotherapy and/or radiation therapy is administered concurrently with the administration of dendritic cells. In some embodiments, the chemotherapy and/or radiation therapy is administered after initial administration of isolated dendritic cells. In some embodiments, the chemotherapy and/or radiation therapy is administered after 1 or less, 2, 3, 4, 5, 6, 7, 8 or more weeks after initial administration of isolated dendritic cells. Administration of isolated dendritic cells may be useful to render the chemotherapy and/or radiation therapy more effective by lowering doses of chemotherapy and/or radiation needed for effective treatment, thereby reducing harmful side effects caused by chemotherapy and/or radiation. Administration of isolated dendritic cells may be useful to render the chemotherapy and/or radiation therapy more effective by rendering cancer cells chemosensitive and/or radiosensitive thereby making chemotherapy and/or radiation therapy more effective.

Methods of Preventing Cancer

In some embodiments, individuals who have been identified as being at elevated risk of cancer are immunized with a composition comprising components selected from the group consisting of: P10s-PADRE, P10s-PADRE plus MONTANIDE™ ISA 51 VG adjuvant, P10s-PADRE plus QS21 adjuvant, and P10s-PADRE plus an adjuvant other than MONTANIDE™ ISA 51 VG adjuvant or QS21 adjuvant.

In some embodiments, instead of using a composition comprising components selected from the group consisting of: P10s-PADRE, P10s-PADRE plus MONTANIDE™ ISA 51 VG adjuvant, P10s-PADRE plus QS21 adjuvant, and P10s-PADRE plus an adjuvant other than MONTANIDE™ ISA 51 VG adjuvant or QS21 adjuvant, individuals who have been diagnosed as having cancer are immunized with a composition comprising components selected from the group consisting of: P10s, P10s plus MONTANIDE™ ISA 51 VG adjuvant, P10s plus QS21 adjuvant, P10s plus an adjuvant other than MONTANIDE™ ISA 51 VG adjuvant or QS21 adjuvant, P10s variants, P10s variants plus MONTANIDE™ ISA 51 VG adjuvant, P10s variants plus QS21 adjuvant, P10s variants plus an adjuvant other than MONTANIDE™ ISA 51 VG adjuvant or QS21 adjuvant, P10s linked to PADRE, P10s linked to PADRE plus MONTANIDE™ ISA 51 VG adjuvant, P10s linked to PADRE plus QS21 adjuvant, P10s liked to PADRE plus an adjuvant other than MONTANIDE™ ISA 51 VG adjuvant or QS21 adjuvant, "P10s linked to other CD4$^+$ helper T cell epitopes peptides", "P10s linked to other CD4$^+$ helper T cell epitopes peptides" plus MONTANIDE™ ISA 51 VG adjuvant, "P10s linked to other CD4$^+$ helper T cell epitopes peptides" plus QS21 adjuvant, "P10s linked to other CD4$^+$ helper T cell epitopes peptides" plus an adjuvant other than MONTANIDE™ ISA 51 VG adjuvant or QS21 adjuvant, P10s variants, P10s variants linked to PADRE plus MONTANIDE™ ISA 51 VG adjuvant, P10s variants linked to PADRE plus QS21 adjuvant, P10s variants linked to PADRE plus an adjuvant other than MONTANIDE™ ISA 51 VG adjuvant or QS21 adjuvant, "P10s variants linked to other CD4$^+$ helper T cell epitopes peptides other than PADRE", "P10s variants linked to other CD4$^+$ helper T cell epitopes peptides other than PADRE" plus MONTANIDE™ ISA 51 VG adjuvant, "P10s variants linked to other CD4$^+$ helper T cell epitopes peptides other than PADRE" plus QS21 adjuvant, "P10s variants linked to other CD4$^+$ helper T cell epitopes peptides other than PADRE" plus an adjuvant other than MONTANIDE™ ISA 51 VG adjuvant or QS21 adjuvant.

In some embodiments, individuals who have been identified as being at elevated risk of cancer are immunized are immunized following treatment by surgery and/or chemotherapy and/or radiation therapy after which the patient has been deemed to be free of detectable cancer. Typically, multiple doses are administered, for example an initial dose and 1, 2, 3, 4, 5, 6, 7 8, 9, or 10 boosts within year one. In some embodiments, following initial dose, boosts are given weeks 2, 3, and 7, weeks 2, 3, 7, and 19, or weeks 2 and 3 and then monthly for one, two three, four, five or six months. The immunization compositions and methods described herein are initially used as an initial dose plus 1, 2, 3, 4, 5, 6, 7 8, 9, or 10 follow-up doses within year one. In some embodiments, yearly boosts are administered.

In some embodiments, patients may be deemed to have detectable cancer cells in one or more lymph nodes. Statistically, a minority of such patients may actually recur although identification of which patients will recur is unknown or difficult to predict. Immunization may be used as an effective means to reduce or elimination recurrence among the minority expected to recur.

In some embodiments, individuals who have been identified as being at elevated risk of cancer may be administered isolated human antibodies as described herein. Typically, multiple doses are administered, for example an initial dose and 1, 2, 3, 4, 5, 6, 7 8, 9, or 10 follow-up doses within year one. In some embodiments, following initial dose, antibody is administered over one, two three, four, five or six months. In some embodiments, yearly administrations are provided thereafter.

Among individuals who have been identified as being at elevated risk of cancer who have been immunized, isolated NK cells may be prepared as described herein and administered to further prevent occurrence or recurrence among immunized individuals.

In some embodiments, individuals who have been identified as being at elevated risk of cancer may be treated with isolated dendritic cells prepared as described herein.

Combination Therapies

Combination therapies using compositions that induce immune response or antibodies as described herein as discussed for use in methods of treating individuals diagnosed with cancer and for preventing cancer in individuals identified as being at a high risk for cancer. In some embodiments, combination therapies comprise administering a vaccine comprising compounds discussed above that include P10s or a variant thereof linked to a CD4+ T cell epitope, preferably formulated with an adjuvant. In some embodiments, the composition comprises P10s-PADRE plus adjuvant such as for examples MONTANIDE™ ISA 51 VG adjuvant or QS21 adjuvant. In some embodiments, the methods comprise administering a another composition set forth herein that can be used to induce immune responses against TACAs, or anti-TACA antibodies described herein, in combination with administration of other therapeutics and/or part of a treatment regimen that includes radiation therapy.

Vaccination in combination with chemotherapy may include regimens in which multiple chemotherapeutics are used to the treatment of the patient. Patients to be treated have been diagnosed with cancer and may have had surgery to remove tumors. In some embodiments, the patient has no detectable cancer; in some embodiments, the patient has detectable disease including metastatic disease. While not limited to such diseases, in some embodiments, cancers to be treated include breast, lung, melanoma, pancreas, colorectal, head and neck including brains cancers such as neuroblastoma and glioblastoma, mouth cancers, esophageal cancers and throat cancers, ovarian cancers, cervical cancer, prostate cancer, thyroid cancer, liver cancer, lymphomas, myelomas and other blood borne cancers. Vaccination in combination with chemotherapy and/or radiation therapy may be particularly useful as data show immune responses generated were cytotoxic in cells that are considered to be fast progressing cancers that are resistant to treatment and difficult to treat. For example, basel-like carcinomas are prevalent in certain populations such as African Americans and Hispanic Americans. These aggressive cancers are associated with poor outcomes. Vaccination in combination with chemotherapy and/or radiation therapy provides the opportunity to treat these difficult cancers.

Vaccination in combination with chemotherapy and/or radiation therapy may be used in cases in which the patient has had a tumor resected and has no detectable cancer. Such post-operative treatment would be to reduce likelihood of recurrence. Vaccination in combination with chemotherapy and/or radiation therapy may be used in cases in which the patient has detectable cancer. Patients with cancer may be diagnosed to be any of Stage 0, I, II, III or IV may be treated with vaccination in combination with chemotherapy and/or radiation therapy.

While not limited to such drugs and drug combinations, in some embodiments, combinations of one or more compounds selected from doxorubicin, cyclophosphamide, docetaxel, cisplatin, vinorelbine as well as Bortezomib, Adriamycin, Trastuzumab, Paclitaxel, Tamoxifen and Pertuzumab. In some, embodiments, P10s-PADRE is administered in combination treatments that include use of one or more such drugs. Examples of other chemotherapeutics which may be included in combination with the vaccines provided herein, particularly P10s-PADRE, include: antimetabolites such as Acivicin, Aminopterin, Aphidicolin, 5-Azacytidine, 1-Alanosine, Cladribine, Cyclocytidine, Cytarabine, 3-Deazauridine, 2-Azacytidine, Diglycoaldehyde, Fludarabine, 5-Fluorouracil, Ftorafur, Hydroxyurea, 6-Mercaptopurine, Methotrexate, PALA, Pentostatin, 6-Thioguanine, Thymidine; Alkylating Agents such as busulfan, carboplatin, chlorambucil, cyclophosphamide, ifosfamide, dacarbazine (DTIC), mechlorethamine (nitrogen mustard), melphalan.4-HC, J1, Mitomycin C, P2, and Sarcolysine; Topoisomerase I-inhibitors such as Camptothecin, SN-38 and Topotecan; Topoisomerase II-inhibitors such as Amsacrine, Bisantrene, Daunorubicin, Epirubicin, Etoposide, Idarubicin, Mitoxantrone and Teniposide; Proteasome inhibitors such as Lactacystin, MG-132, and MG-262; and Tubulin active agents such as Colchicine, Maytansine, Podophyllotoxin, Vinblastine, Vincristine, Vindesine and Estramustine. Other examples of chemotherapeutics which data indicate may be particularly effective in combination with the vaccines provided herein, particularly P10s-PADRE, include: Aclarubicin, Anguidine, Cycloheximide, Flavoneacetate, Hoechst 33342, MBGB, MIBG, Spirogermanium, and Herceptin. Examples of other chemotherapeutics include cytosinarabinoside, bleomycin. purothionin (barley flour oligopeptide), macromomycin. 1,4-benzoquinone derivatives, treninom, carmustine (BCNU) lomustine (CCNU), dactinomycin, prednisone, dexamethasone, tamoxifen, fulvestrant, anastrozole, letrozole, megestrol acetate, bicalutamide, flutamide, leuprolide, goserelin, Avastin, L-asparaginase and tretinoin. In some embodiments, one or more anti-cancer compound is compounds from a class of compounds selected from the group consisting of: Antimetabolites, Alkylating Agents; Topoisomerase I-inhibitors, Topoisomerase II-inhibitors, Proteosome inhibitors, Antibody therapies and tubulin active agents. In some embodiments, one or more anti-cancer compound is compounds from a class of compounds selected from the group consisting of: Nitrosoureas; Antitumor Antibiotics; Corticosteroid Hormones; Anti-estrogens; Aromatase Inhibitors; Progestins; Anti-androgens; LHRH agonists; and other anti-cancer therapies.

Chemotherapy may precede vaccination and/or be administered during immunization treatment and/or after immunization has discontinued. The co-administration of therapeutics can be sequential in either order or simultaneous. In some embodiments the composition comprising P10s-PADRE plus adjuvant such as for examples MONTANIDE™ ISA 51 VG adjuvant or QS21 adjuvant, or another composition set forth herein that can be used to induce immune responses against TACAs, or a composition comprising anti-TACA antibodies described herein, is co-administered with more than one additional therapeutic.

In some embodiments, administration of chemotherapeutics results in enhanced immune responses to the vaccine. In some embodiments, chemotherapeutics enhance the antigen presenting ability of B cells. In some embodiments, chemotherapeutics facilitate adaptive T cell immunity by eliminating "suppressor" T cells. In some embodiments, chemotherapeutics switch cytokine production of tumor-infiltratingmacrophages from IL-10 to IFN-γ and polarize Th1/Th2 responses. In some embodiments, chemotherapeutics increase the ratio between effector T cells and regulatory T cells ($T_{regs}$) and reduce immunosuppressive activity of the latter in patients. Such studies provide the rationale for the selective use of active immunotherapy regimens in combination with specific standard-of-care therapies to achieve the most beneficial clinical outcome among carcinoma patients.

In some embodiments, immune responses induced by the vaccine sensitize tumor cells for more efficient killing by chemotherapeutics. In some embodiments, immunization followed by chemotherapy facilitates inhibition of tumor growth. In some embodiments, immune responses induced by immunization lowers the LC50 value of chemotherapeutic making the chemotherapy more effective. Such immunization augments chemotherapy.

In some embodiments, immune responses induced by vaccine are cytotoxic to chemoresistant tumor cells. As described herein, sera from immunized individual rendered chemoresistant cells chemosensitive. Accordingly, in some embodiments, P10s-PADRE plus adjuvant such as for examples MONTANIDE™ ISA 51 VG adjuvant or QS21 adjuvant, or another composition set forth herein that can be used to induce immune responses against TACAs or a composition comprising anti-TACA antibodies described herein is administered prior to administration of an anti-cancer drug such that the immunization will induce an immune response that will be occurring for sufficient time to render cancer cells chemosensitive at the time the cancer drug is administered. In some embodiments, a previously immunized individual may be boosted 72 hours or less prior to administration of a chemotherapy.

Similarly, compositions comprising P10s-PADRE plus adjuvant such as for examples MONTANIDE™ ISA 51 VG adjuvant or QS21 adjuvant, or another composition set forth herein that can be used to induce immune responses against TACAs, or a composition comprising anti-TACA antibodies described herein, may be administered in combination with radiation therapy. The therapeutic regimens can include sequential administration of composition and initiation of radiation therapy in either order or simultaneously. Those skilled in the art can readily formulate an appropriate radiotherapeutic regimen. Carlos A Perez & Luther W Brady: Principles and Practice of Radiation Oncology, 2nd Ed. JB Lippincott Co, Phila., 1992, which is incorporated herein by reference describes radiation therapy protocols and parameters which can be used in the present invention.

For GBMs (glioblastoma, the most malignant glial brain tumor), Simpson W. J. et al.: Influence of location and extent of surgical resection on survival of patients with glioblastoma multiforms: Results of three consecutive Radiation Therapy Oncology Group (RTOG) clinical trials. Int J Radiat Oncol Biol Phys 26:239-244, 1993, which is incorporated herein by reference describes clinical protocols useful in the methods of the present invention. Similarly, for Borgelt et al., The palliation of brain metastases: Final results of the first two studies of the Radiation Therapy Oncology Group. Int J Radiat Oncol Biol Phys 6:1-9, 1980, which is incorporated herein by reference, describes clinical protocols useful in the methods of the present invention. In some preferred embodiments, radiation therapy using gamma radiation is provided.

In some embodiments, P10s-PADRE plus adjuvant such as for examples MONTANIDE™ ISA 51 VG adjuvant or QS21 adjuvant, or another composition set forth herein that can be used to induce immune responses against TACAs or a composition comprising anti-TACA antibodies described herein, is administered prior to radiation therapy such that the immunization will induce an immune response that will be occurring for sufficient time to be affecting cancer cells at the time the radiation is administered. In some embodiments, a previously immunized individual may be boosted 72 hours or less prior to radiation therapy.

In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and/or cyclophosphamide and/or docetaxel. In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently followed by docetaxel treatment. In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles. In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles wherein patients receive the first cycle of chemotherapy along with the first injection of vaccine on week 1, two subsequent two injections of the vaccine one week apart (week 2 and 3), a second cycle of chemotherapy on week 4, and subsequent cycles of chemotherapy every 21 days (week 7, 10, 13, 16, 19, 22). In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles wherein patients receive the first cycle of chemotherapy on week 1, the first injection of vaccine on week 2, the subsequent two injections of the vaccine one week apart (week 3 and 4), second cycle of chemotherapy on week 4 (along with second vaccine injection) and subsequent cycles of chemotherapy every 21 days (week 7, 10, 13, 16, 19, 22). In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles wherein patients receive three weekly injections of vaccine (week 1, 2, 3), then first cycle of chemotherapy (week 4), and subsequent cycles of chemotherapy every 21 days (week 7, 10, 13, 16, 19, 22, 25). In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles wherein patients receive the first injection of vaccine on week 1, the subsequent two injections of the vaccine one week apart (week 2 and 3), the first cycle of chemotherapy on week 2 (along with second vaccine injection) and subsequent cycles of chemotherapy every 21 days (week 5, 8, 11, 14, 17, 20, 23). In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of doxorubicin and cyclophosphamide administered concurrently every three weeks for four cycles followed by docetaxel treatment every three weeks for four cycles wherein patients receive the first injection of vaccine on week 1, the subsequent two injections of the vaccine one week apart (week 2 and 3), the first cycle of chemotherapy on week 3 (along with third vaccine injection) and subsequent cycles of chemotherapy every 21 days (week 6, 9, 12, 15, 18, 21, 24).

In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of docetaxel before immunization. In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of docetaxel concurrent with and/or after completion immunization. In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of Docetaxel, Pertuzumab and Trastuzumab concurrent with and/or after completion immunization.

In some embodiments, chemotherapy used in conjunction with immunization with compositions provided herein, such as P10s-PADRE plus adjuvant such as for examples MONTANIDE™ ISA 51 VG adjuvant or QS21 adjuvant, includes administration of Adriamycin, Cyclophosphamide, Paclitaxel Trastuzumab and Vinorelbine prior to and/or concurrent with and/or after completion immunization.

While not limited to solid tumors, cancers including those which are characterized be solid tumors as well as lymphomas, myelomas and other blood borne cancers, may be treated with P10s-PADRE plus adjuvant such as for examples MONTANIDE™ ISA 51 VG adjuvant or QS21 adjuvant, or another composition set forth herein that can be used to induce immune responses against TACAs, or a composition comprising anti-TACA antibodies described herein, in combination with Velcade (Bortezomib) or a similar acting compound which downregulates cell surface expression of HLA class I and enhances natural killer cell-mediated lysis. Treatment with P10s-PADRE plus adjuvant such as for examples MONTANIDE™ ISA 51 VG adjuvant or QS21 adjuvant, or another composition set forth herein that can be used to induce immune responses against TACAs, or a composition comprising anti-TACA antibodies described herein, make Velcade more effective and Velcade makes treatment with P10s-PADRE plus adjuvant such as for examples MONTANIDE™ ISA 51 VG adjuvant or QS21 adjuvant, or another composition set forth herein that can be used to induce immune responses against TACAs, or a composition comprising anti-TACA antibodies described herein, more effective. In some embodiments, P10s-PADRE plus adjuvant such as for examples MONTANIDE™ ISA 51 VG adjuvant or QS21 adjuvant, or another composition set forth herein that can be used to induce immune responses against TACAs or a composition comprising anti-TACA antibodies described herein, are administered prior to Velcade such that the immunization will induce an immune response that will be occurring for sufficient time to be affecting cancer cells at the time the Velcade is administered. In some embodiments, a previously immunized individual may be boosted 72 hours or less prior to Velcade therapy. The combination of Velcade and P10s-PADRE plus adjuvant such as for examples MONTANIDE™ ISA 51 VG adjuvant or QS21 adjuvant, or another composition set forth herein that can be used to induce immune responses against TACAs or a composition comprising anti-TACA antibodies described herein, may be used to treat individuals diagnosed with cancer including solid tumors or a form of cancer of blood cells. The combination of Velcade and P10s-PADRE plus adjuvant such as for examples MONTANIDE™ ISA 51 VG adjuvant or QS21 adjuvant, or another composition set forth herein that can be used to induce immune responses against TACAs or a composition comprising anti-TACA antibodies described herein, may be used to prevent cancer occurrence/recurrence in individuals identified as being at high risk for cancer.

Some combination therapies include the use of IL-12, delivered as a protein or as encoded by a nucleic acid vehicle such as a DNA vaccine, to enhance immune responses in immunized patients. IL-12 delivery may be timed prior to, simultaneously with, or after a dose of vaccine in an immunization method.

Preparation, Formulation and Administration of Compositions

The compositions may further comprise physiologically acceptable carrier or diluent. Peptides can be synthesized by those having ordinary skill in the art using well known techniques and readily available starting materials. Peptides may be produced using any method known in the art, including, but not limited to, chemical synthesis as well as biological synthesis in an in vitro or in vivo in a eukaryotic or prokaryotic expression system. For example, peptides of the invention may be produced by solid phase synthesis techniques as taught by Merryfield, (1963) J. Am. Chem. Soc., 15:2149-2154 and J. Stuart and J. D. Young, Solid Phase Peptide Synthelia, Pierce Chemical Company, Rockford, Ill. (1984), each of which is incorporated herein by reference.

The peptides and recombinant antibodies of the present invention may be administered by oral, intraperitoneal, intramuscular and other conventional routes of pharmaceutical administration. Pharmaceutical compositions of the present invention may be administered either as individual therapeutic/prophylactic agents or in combination with other agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.0001 to 1 grams per kilogram of body weight, in some embodiments about 0.1 to 100 milligrams per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. Dosage forms (composition) suitable for internal administration generally contain from about 1 milligram to about 500 milligrams of active ingredient per unit. In these pharmaceutical compositions the active ingredient will ordinarily be present in an amount of about 0.5-95 by weight based on the total weight of the composition.

In some embodiments, P10s-PADRE is combined with MONTANIDE™ ISA 51 VG adjuvant in an injectable formulation comprising at least 300 µg P10s-PADRE, in some embodiments at least 500 µg P10s-PADRE, and at least 1000 µg or more P10s-PADRE.

In some embodiments, P10s-PADRE is combined with QS21 adjuvant in an injectable formulation comprising at least 300 µg P10s-PADRE, in some embodiments at least 500 µg P10s-PADRE, and at least 1000 µg or more P10s-PADRE.

In some embodiments, P10s-PADRE is combined with an adjuvant such as, for example, one described above in an injectable formulation comprising at least 300 µg P10s-PADRE, in some embodiments at least 500 µg P10s-PADRE, and at least 1000 µg or more P10s-PADRE.

In some embodiments, P10s peptide linked to a CD4$^+$ helper T cell epitope, i.e. P10s linked to a CD4$^+$ helper T cell epitope, comprising P10s linked to a CD4$^+$ helper T cell epitope such as, for example, those described above is combined with an adjuvant such as, for example, one described above in an injectable formulation comprising at least 300 µg P10s peptide linked to a CD4$^+$ helper T cell epitope, in some embodiments at least 500 µg P10s linked to a CD4$^+$ helper T cell epitope, and at least 1000 µg or more P10s linked to a CD4$^+$ helper T cell epitope.

In some embodiments, a P10s variant linked to a CD4$^+$ helper T cell epitope, i.e. a variant of P10s as described above, that is linked to a CD4$^+$ helper T cell epitope, such as, for example, those described above and is combined with an adjuvant such as, for example, one described above in an injectable formulation comprising at least 300 µg P10s variant linked to a CD4$^+$ helper T cell epitope, in some embodiments at least 500 µg P10s variant linked to a CD4$^+$ helper T cell epitope, and at least 1000 µg or more P10s variant linked to a CD4$^+$ helper T cell epitope.

For parenteral administration, the compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. The vehicle or lyophilized powder may contain additives that maintain isotonicity (e.g., sodium chloride, mannitol) and chemical stability (e.g., buffers and preservatives). The formulation is sterilized by commonly used techniques. Suitable pharmaceutical carriers are described in the most recent edition of Remington's Pharmaceutical Sciences, 18th Edition, A. R. Gennaro et al. Eds., Mack Publishing Co., Easton, Pa., 1990, a standard reference text in this field.

Generally, additives for isotonicity can include sodium chloride, dextrose, mannitol, sorbitol and lactose. In some cases, isotonic solutions such as phosphate buffered saline are used. Stabilizers include gelatin and albumin. In some embodiments, a vasoconstriction agent is added to the formulation. The pharmaceutical preparations according to the present invention are preferably provided sterile and pyrogen free.

One of skill in the art of pharmaceutical formulations, e.g., having an advanced degree in Pharmaceutics or Pharmaceutical Sciences, can prepare a variety of appropriate dosage forms and formulations for the compositions of the invention with no more than routine experimentation. A number of texts in the field, e.g., Remington's Pharmaceutical Sciences and The U.S. Pharmacopoeia/National Formulary, latest editions, provide considerable guidance in this respect.

A pharmaceutically acceptable formulation will provide the active ingredient(s) in proper physical form together with such excipients, diluents, stabilizers, preservatives and other ingredients as are appropriate to the nature and composition of the dosage form and the properties of the drug ingredient(s) in the formulation environment and drug delivery system.

Subsequent to initial administration, individuals may be boosted by re-administration. In some preferred embodiments, multiple administrations are performed. In some embodiments, one, two, three, four, five, six, seven, eight, nine, ten or more boosts are administered within the first year of treatment. In some embodiments, following the first year of treatment, boosts may be administered annually, more frequently, or less frequently than annually.

DNA Vaccines

DNA vaccines based upon the P10s and variants, as MAP constructs or as CMP plus CD4$^+$ helper T cell epitope peptides may be prepared. Recent advances in vaccine development have demonstrated the feasibility of inducing protective immunity against various pathogens through the administration of engineered DNA vectors. Administration of a DNA vaccines resulting in endogenous expression of carbohydrate peptide mimics will induce protective immunity against encapsulated organisms, other pathogens and against tumor cells. The advantages associated with DNA-based vaccines include ease of construction and standardization, stability and heat resistance, the ability to incorporate representation of several serogroups in one vector, ability to insert potent immunogenic motifs such as CpG, induction of a T helper cell type 1 (Th1) response and extremely low cost of production. Intranasal immunization will potentially enhance the benefits of this vaccine preparation by facilitating ease of administration, low cost and by stimulating an effective mucosal immune response. This may be particularly effective strategy in infants as the mucosal immunity matures to adult level within the first months of life, in contrast to systemic immunity.

DNA vaccines can potentially overcome the problems associated with both native polysaccharide as well as the conjugate polysaccharide vaccines.

DNA vaccines are described in U.S. Pat. Nos. 4,945,050, 5,036,006, 5,593,972, 5,739,118, 5,817,637, 5,830,876, 5,962,428, 5,981,505, 5,580,859, 5,703,055, and 5,676,594. The use of electroporation to deliver the genetic construct, as described in U.S. Pat. Nos. 5,273,525, 5,439,440, 5,702, 359, 5,810,762, 5,993,434, 6,014,584, 6,055,453, 6,068,650, 6,110,161, 6,120,493, 6,135,990, 6,181,964, 6,216,034, 6,233,482, 6,241,701, 6,347,247, 6,418,341, 6,451,002, 6,516,223, 6,567,694, 6,569,149, 6,610,044, 6,654,636, 6,678,556, 6,697,669, 6,763,264, 6,778,853, 6,865,416, 6,939,862, 6,958,060 and 7,245,963

All references and patents and published patent applications referred to herein are incorporated herein by reference.

EXAMPLES

Example 1

Glycan array analyses of the polyreactivity of IgG fraction from intravenous immunoglobulin (IVIg) affinity purified on P10s peptide were performed. The results are shown in FIG. 1. The peptide is a mimic of gangliosides GD2/GD3 but the preexisting human IgG that recognize it bind a wide range of other sugars. Among the most strongly enriched reactivities are those to oligosaccharide molecules representing degradation products of starch, glycogen and cellulose as well as several milk sugars. Both fractions are tested at 0.1 mg/ml. On each axis the reactivity of the respective IgG fraction is represented in logarithmic scale in arbitrary fluorescent units. FIG. 1 shows that most binding is with cellulose. The single cross hatched shaded square represent maltose. The single darkened square is glucose, the single unshaded square represents isomaltotriose glucose and the single square that is lightly shaded and filled with dots is lactose.

Figure 2:
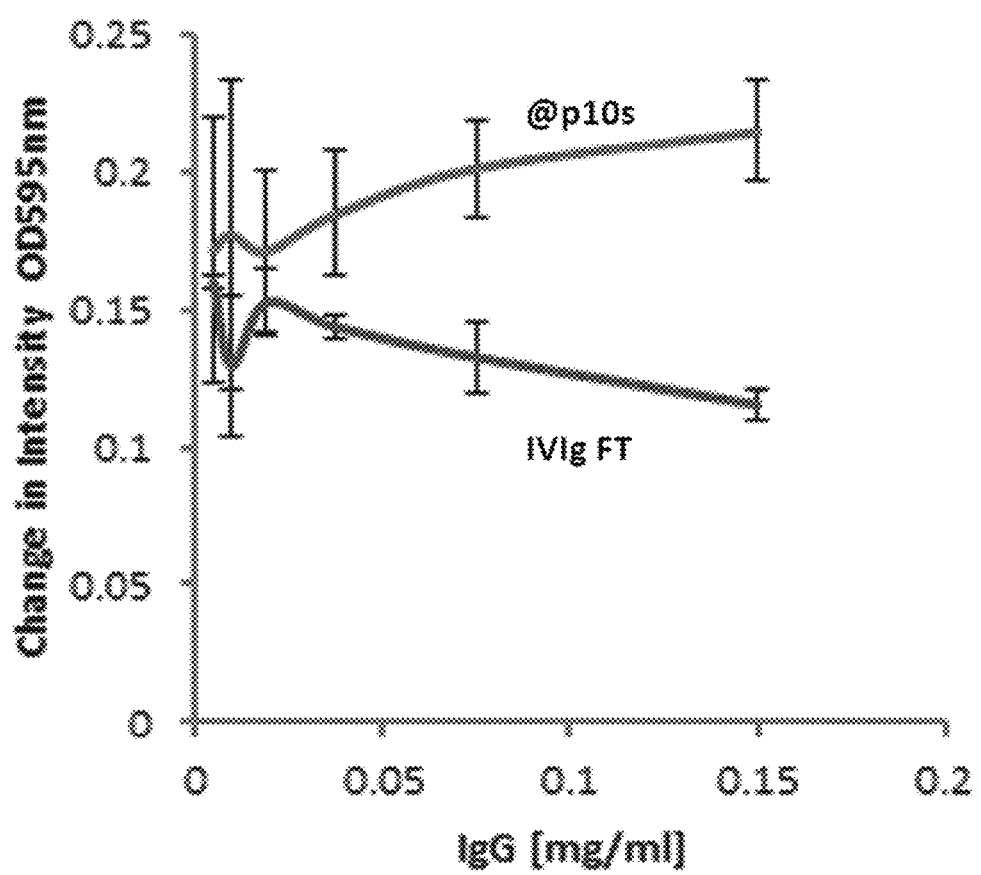
FIG. 2 shows amylolytic activity in IVIg is enriched in the @P10s fraction as described in Example 1.

As shown in FIG. 2, amylolytic activity in IVIg is enriched in the @P10s fraction. Dialyzed IVIg solution at 40 mg/ml was incubated with P10s coupled to Sepharose for 4 hours. The flow through and the acid/base eluted fractions were extensively dialyzed and tested for amylolytic activity by incubating with 0.05 mg/ml soluble starch solution for 2 hours at room temperature. At the end of the incubation 0.08% iodine tincture was added and the color intensity was measured at 595 nm. The upper curve on the graph is p10s; the lower curve is IVIg FT. The values represent mean and SD of the difference from the average intensity of wells without immunoglobulin.

Figure 3A:
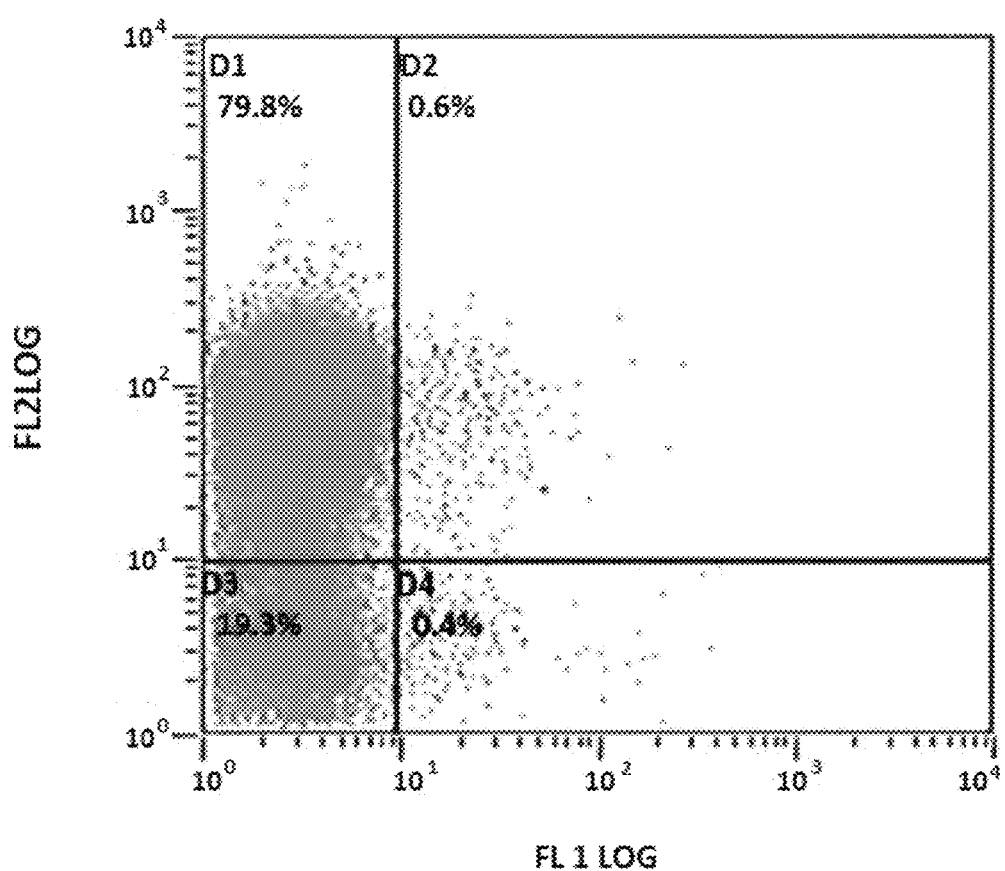
FIGS. 3A and 3B shows results of experiments described in Example 1 in which CD23+ (FL2) and CD23- BALB/c mouse splenocytes, gated for CD19 expression (FL4) were stained with P10s-quantum dot clusters (525 nm—FL1).
Figure 3B:
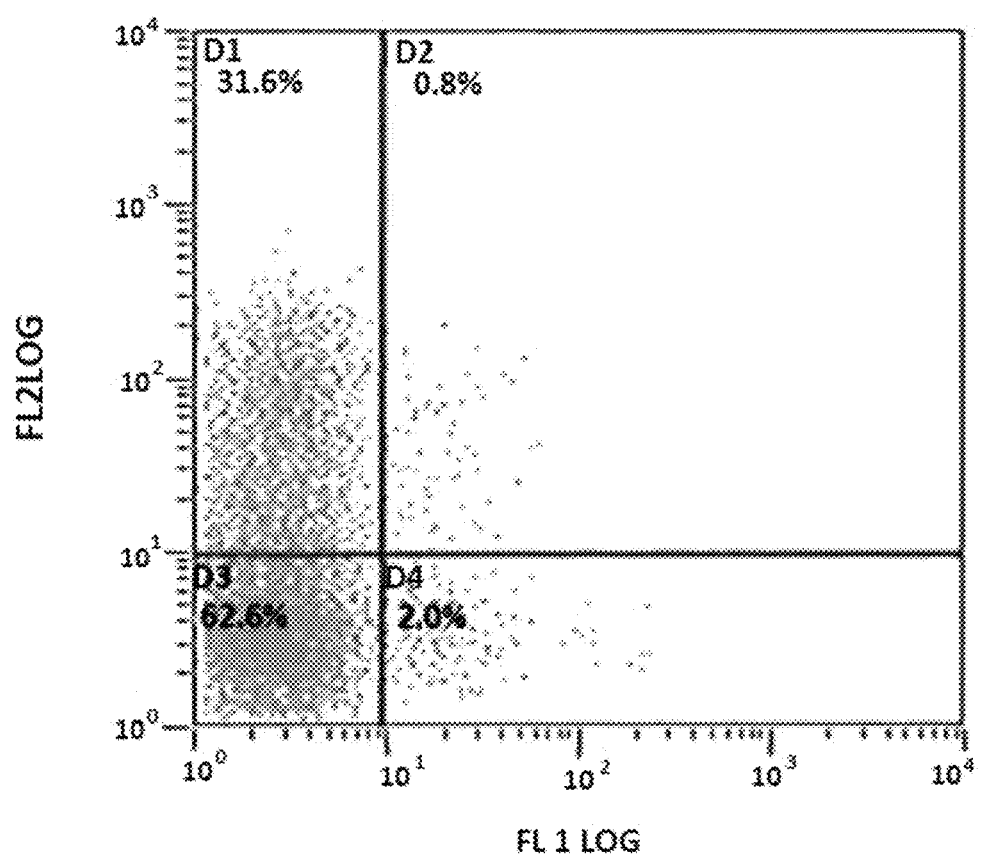

FIG. 3A shows staining with P10s-quantum dot clusters (525 nm—FL1) of CD23$^+$ (FL2) and CD23$^-$ small BALB/c mouse splenocytes, gated for CD19 expression (FL4). FIG. 3B shows staining with P10s-quantum dot clusters (525 nm—FL1) of CD23$^+$ (FL2) and CD23$^-$ large BALB/c mouse splenocytes, gated for CD19 expression (FL4). The staining is consistent with polyspecific reactivity since the P10s$^+$ B cell population sizes are in a range between phenotypic subpopulations and antigen specific cells. As expected for polyspecific and carbohydrate reactive cells p10s$^+$ B cells are predominantly CD23$^-$—probably marginal zone or splenic B1 cells. The data in FIG. 3A is as follows. The quadrant designated D1 shows 79.8%. The quadrant designated D2 shows 0.6%. The quadrant designated D3 shows 19.3%. The quadrant designated D4 shows 0.4%. The data in FIG. 3B is as follows. The quadrant designated D1 shows 34.6%. The quadrant designated D2 shows 0.8%. The quadrant designated D3 shows 62.6%. The quadrant designated D4 shows 2.0%.

Example 2

P10s-PADRE having the sequence H-Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH2 was synthesized. P10s-PADRE is a 25 amino acid peptide with 23 amino acids in the L configuration and 2 in the D configuration (Ala13 and Ala25 are each D amino acids shown as dAla). Ala at position 15 is a modified L configuration alanine, cyclohexylalanine (CHAla, CHAla15, Cha or Cha15). Using the single-letter abbreviations of the amino acids, the P10s-PADRE sequence is: [hydrogen]-W—R-Y-T-A-P-V-H-L-G-D-G-dA-K-Cha-V-A-A-W-T-L-K-A-A-dA-NH2. The Molecular Formula of the P10s PADRE is $C_{128}H_{197}N_{35}O_{30}$. The Acetate Peptide to counter ion ratio: 86.6% to 4.5%. P10s-PADRE is a cationic, basic (computed isoelectric point=9.7) peptide with good aqueous solubility in acidic pH. There are no amidated amino acids or cysteines in the sequence. Molecular Weight: 2706.9 Da. A new immunomodulatory procedure is described in which immunization with a carbohydrate mimetic peptide (CMP, also called a mimotope; P10s-PADRE, also referred to as P10s-PADRE$_{DAla13,CHAla,DAla25}$) is used to elicit carbohydrate reactive antibodies.

Example 3

Overcoming tumor-cell adaptation and survival is critical in preventing therapeutic failure and serves potentially as a basis of new immunotherapeutic strategies. Carbohydrate mimetic peptides (CMPs) that induce broad-spectrum humoral and cellular responses that inhibit tumor growth have been developed. One of these CMPs, referred to as P10s (SEQ ID NO:1) has been modified to include a universal CD4$^+$ helper T cell epitope PADRE (dAla-Lys-CHAla-Val-Ala-Ala-Trp-Thr-Leu-Lys-Ala-Ala-dAla) to produce P10s-PADRE (H-Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH2 in which Ala13 and Ala25 are each D amino acids shown as dAla, and Ala at position 15 is a modified L configuration Alanine, cyclohexylalanine (shown as CHAla).

A Phase I first-in-man dose-escalation trial testing of P10s-PADRE in stage IV breast cancer patients was initiated. Immunized subjects mounted an anti-P10s response, and the serum and plasma antibodies of post-immunized subjects mediated cytotoxicity against human breast cancer cell lines, including a cell line with de novo resistance to Trastuzumab. P10s was designed to induce responses to several TACAs including the neolactoseries antigen Lewis Y (LeY) and the ganglioside GD2. These antigens are intimately involved in cell signaling mechanisms associated with cell death.

A vaccine was manufactured and used to vaccinate stage IV metastatic breast cancer patients to assess its safety and tolerability. The vaccines include the P10s sequence (SEQ ID NO:1 which is based upon the crystal structures of anti-GD2 and anti-LeY antibodies. P10s was developed as a more faithful mimic of TACAs than its parent peptide (referred to as P10 or P10orignal—SEQ ID NO:2).

P10s was synthesized with the Pan T cell peptide PADRE in modified form using GLP validation. The P10s-PADRE vaccine was developed for treatment of breast cancer patients with high risk of disease relapse. Phase I trial research participants were restricted to females of all races with histologically or cytologically confirmed stage IV breast cancer (newly diagnosed, metastatic or relapsed after primary or adjunctive therapy and which have not required a treatment change for 2 months). Two cohorts of 3-6 stage IV breast cancer patients were to be enrolled.

Initially, a single cohort was administered P10s-PADRE (300 µg/mL) formulated with MONTANIDE™ ISA 51 VG Adjuvant™. Doses of P10s-PADRE admixed with MONTANIDE™ ISA 51 VG Adjuvant™ adjuvant was administered to subjects subcutaneously in rotating injection sites in the abdomen. At present four subjects have completed their immunization course of 5 immunizations over 23 weeks: weeks 1-3 hyperimmunization, week 7 and boosted at week 19.

Figure 4:
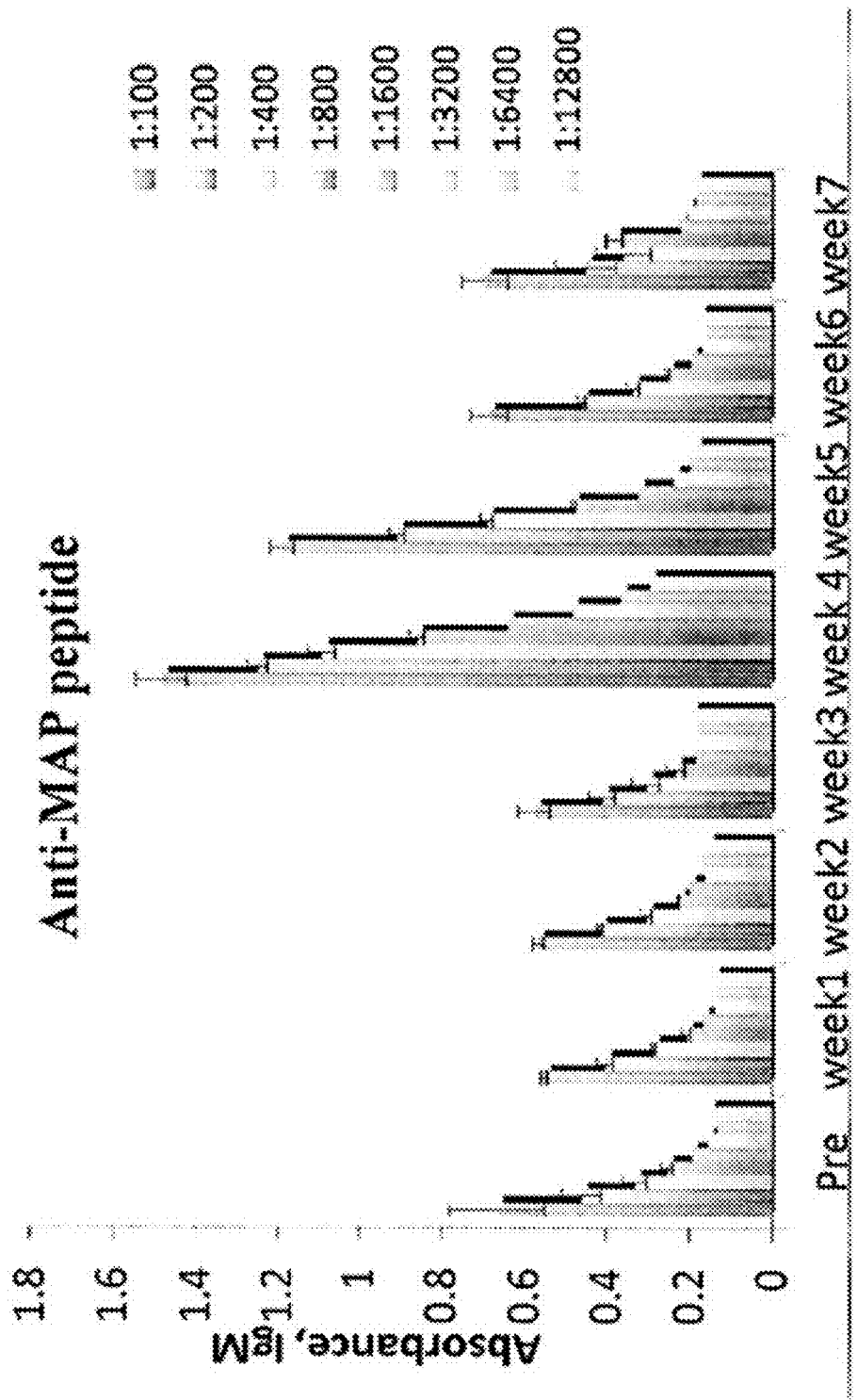
FIG. 4 shows results from experiments measuring IgM antibody responses in Stage IV breast cancer patients immunized with P10s-PADRE in the Phase I trial of P10s-PADRE.
Figure 5:
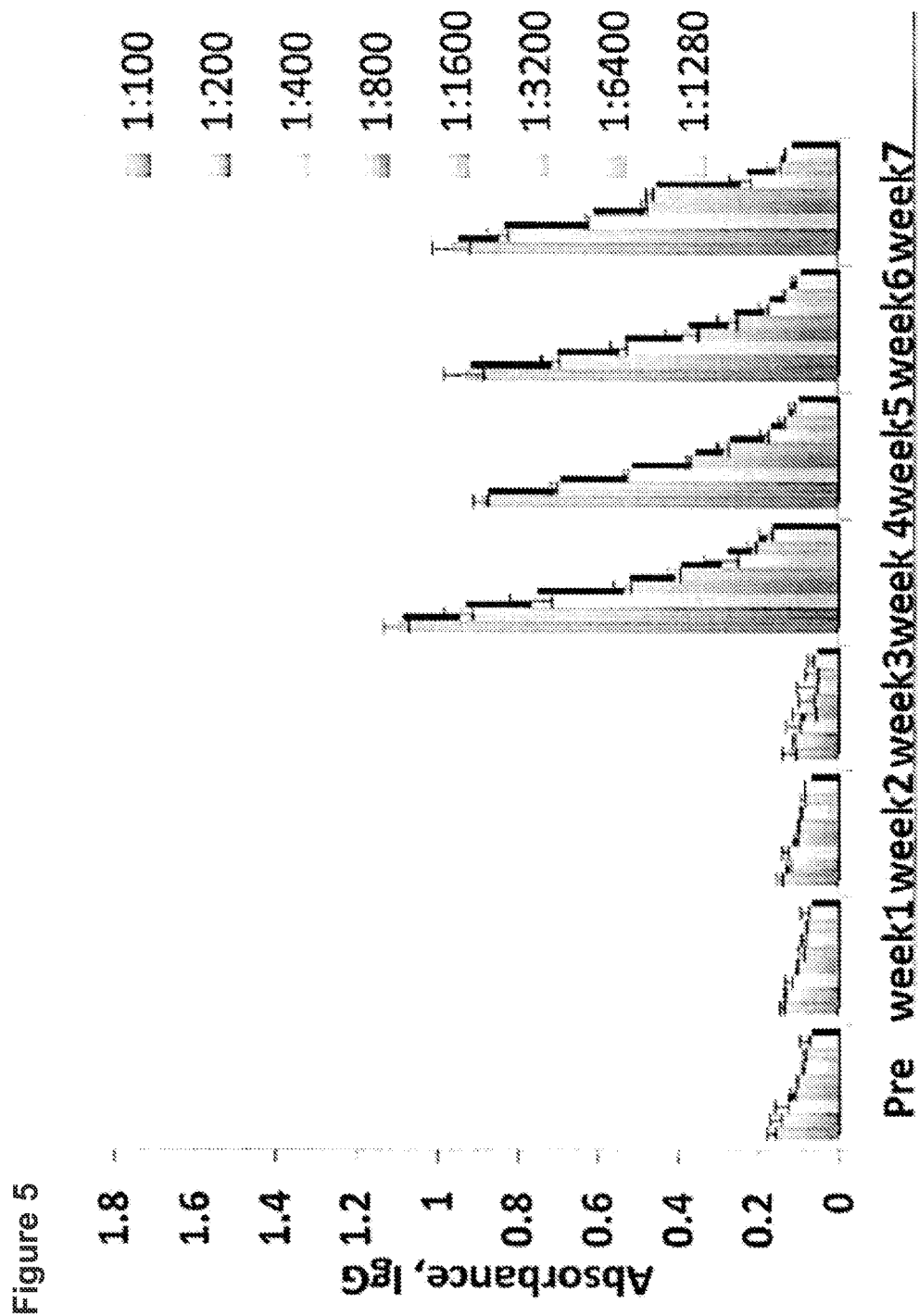
FIG. 5 shows results from experiments measuring IgG antibody responses in Stage IV breast cancer patients immunized with P10s-PADRE in the Phase I trial of P10s-PADRE.
Figure 6:
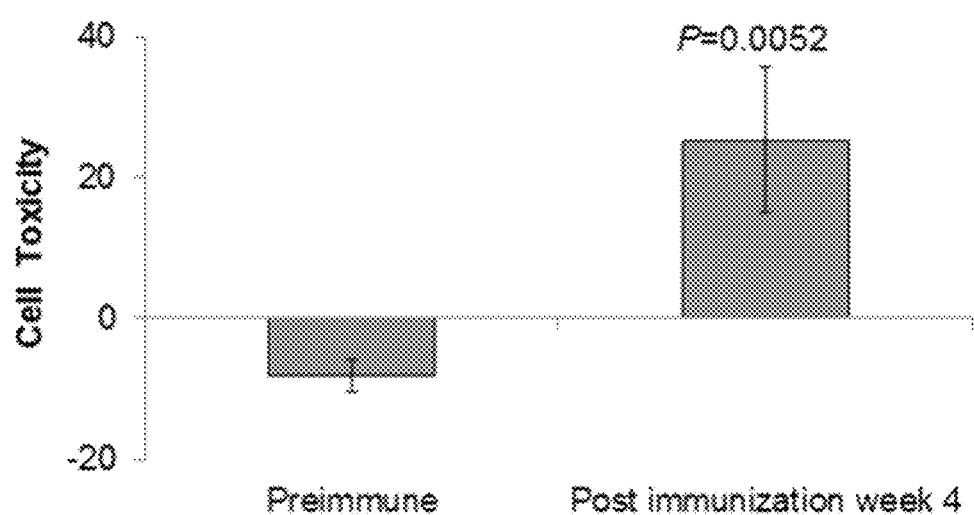
FIG. 6 contains data showing antibodies induced in Stage IV breast cancer patients immunized with P10s-PADRE in the Phase I trial of P10s-PADRE were cross reactive to HCC1954 cells with cytotoxic activity.

All subjects displayed an IgG and IgM response to the vaccine. FIG. 4 shows IgM antibody responses in immunized individuals. FIG. 5 shows IgG antibody responses in immunized individuals. FIG. 6 shows antibodies from immunized individuals induced were cross reactive to HCC1954 cells with cytotoxic activity.

No dose-limiting toxicities (DLTs) were observed in the first four subjects, and no DLT has thus far been observed in the fifth subject. This information indicates that vaccination at an initial dose level of 500 µg P10s-PADRE per injection should be safe and tolerable.

Figure 7A:
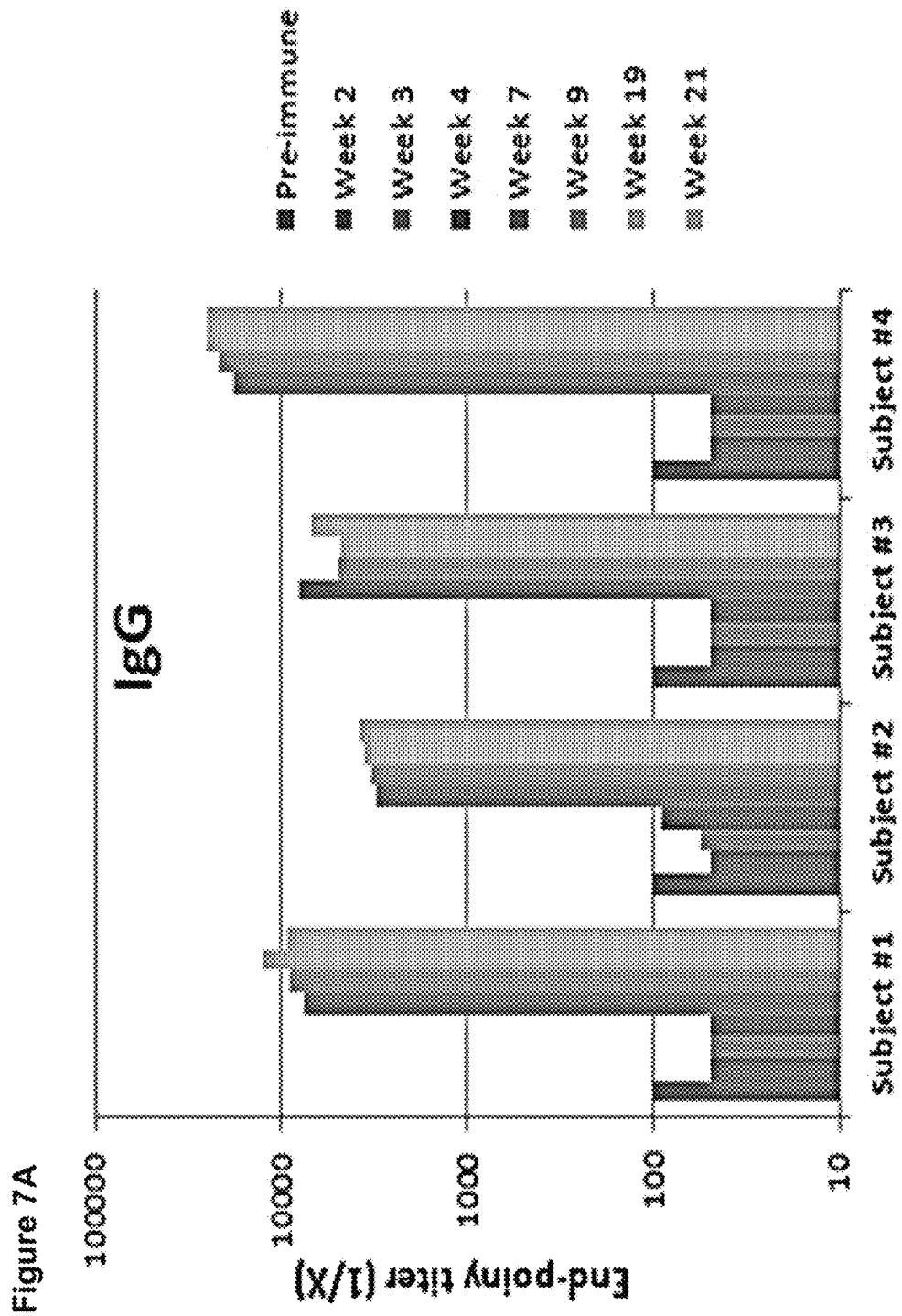
FIGS. 7A and 7B contain data showing that immunization with P10s-PADRE in the Phase I trial of P10s-PADRE generated antibodies reactive with the MAP form of P10s peptide that bind and induce cytotoxicity in human HCC1954 cancer cells. Each of FIGS. 7A and 7B is a bar graph with data from four patients measures at eight time points. As shown in the x-axis of the graph in each figure, data is provided for four patients: Subject 1, Subject 2, Subject 3 and Subject 4. For each patient, data was measured at eight time points: pre-immune, week 2, week 3, week 4, week 7, week 9, week 19 and week 21. For each patient, data is shown for the eight time points. The bar at the left end at patient on the x-axis corresponds to pre-immune. Immediately to the right of the pre-immune bar is the Week 2 bar. Immediately to the right of the Week 2 bar is the Week 3 bar. Immediately to the right of the Week 3 bar is the Week 4 bar. Immediately to the right of the Week 4 bar is the Week 7 bar. Immediately to the right of the Week 7 bar is the Week 9 bar. Immediately to the right of the Week 9 bar is the Week 19 bar. Immediately to the right of the Week 19 bar is the Week 21 bar. Each of FIGS. 7A and 7B shows 32 data points.
Figure 7B:
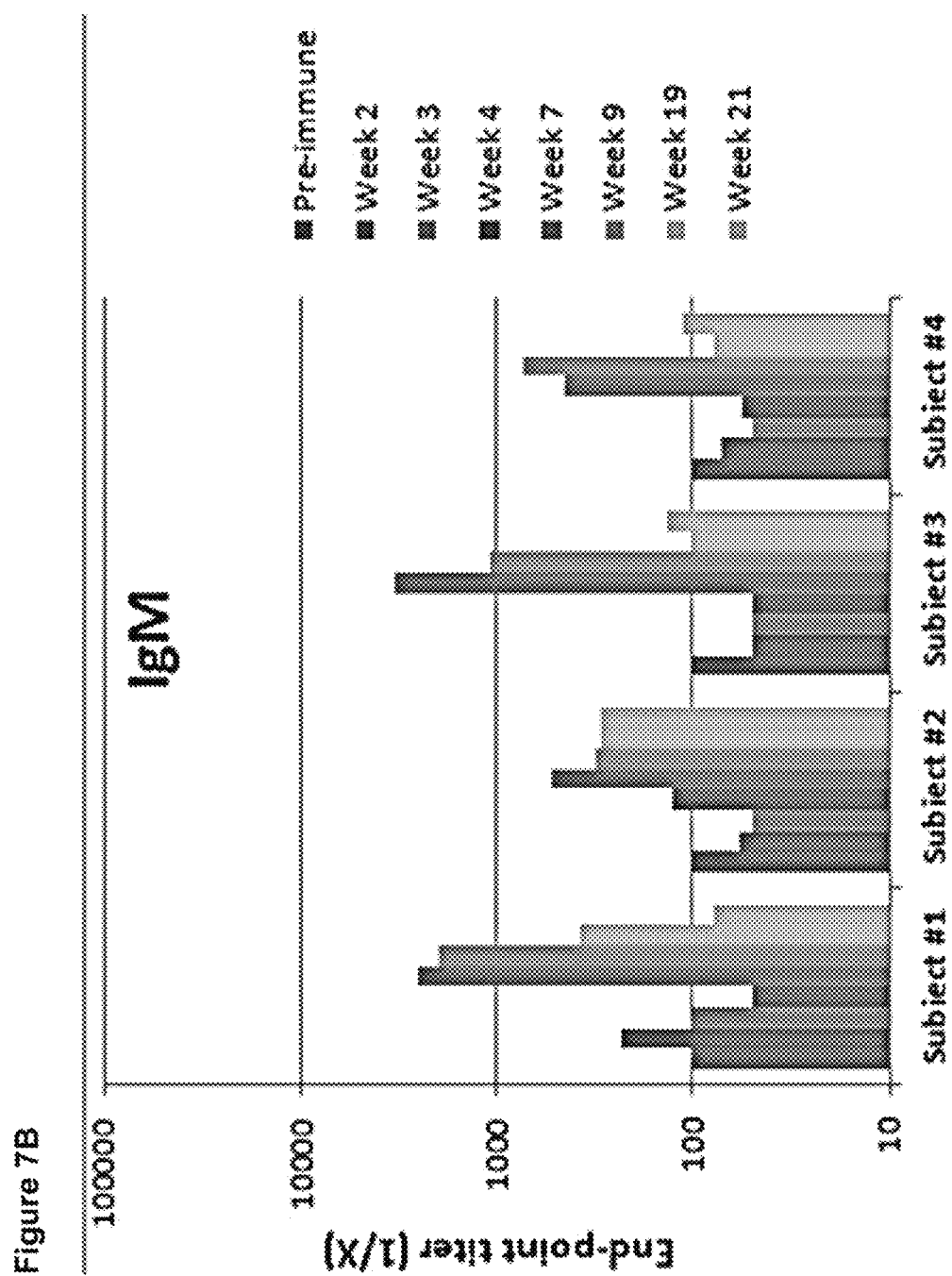

As shown in FIGS. 7A and 7B, immunization with P10s generates antibodies reactive with the peptide that bind and induce cytotoxicity in human HCC1954 cancer cells. ELISA plates were coated with MAP version of P10s and reactivity of two-fold serial dilutions of pre- and post-immune sera was detected by HRP-conjugated anti-human IgG (FIG. 7A) and IgM (FIG. 7B). The endpoint titers shown in FIG. 7A and FIG. 7B were estimated from absorbance-versus-dilution curves by linear regression. The intercept of the regression line for each subject's pre-immune serum was the value used as the absorbance cutoff for determining end-point titer for that subject, and the dilution where each sample's regression line crossed the subject's absorbance cutoff was defined to be the sample's end-point titer. Extrapolation beyond one dilution below the minimum or above the maximum actual dilutions was not allowed. This procedure normalized each subject's pre-immune titer to be 1:100.

Figure 8A:
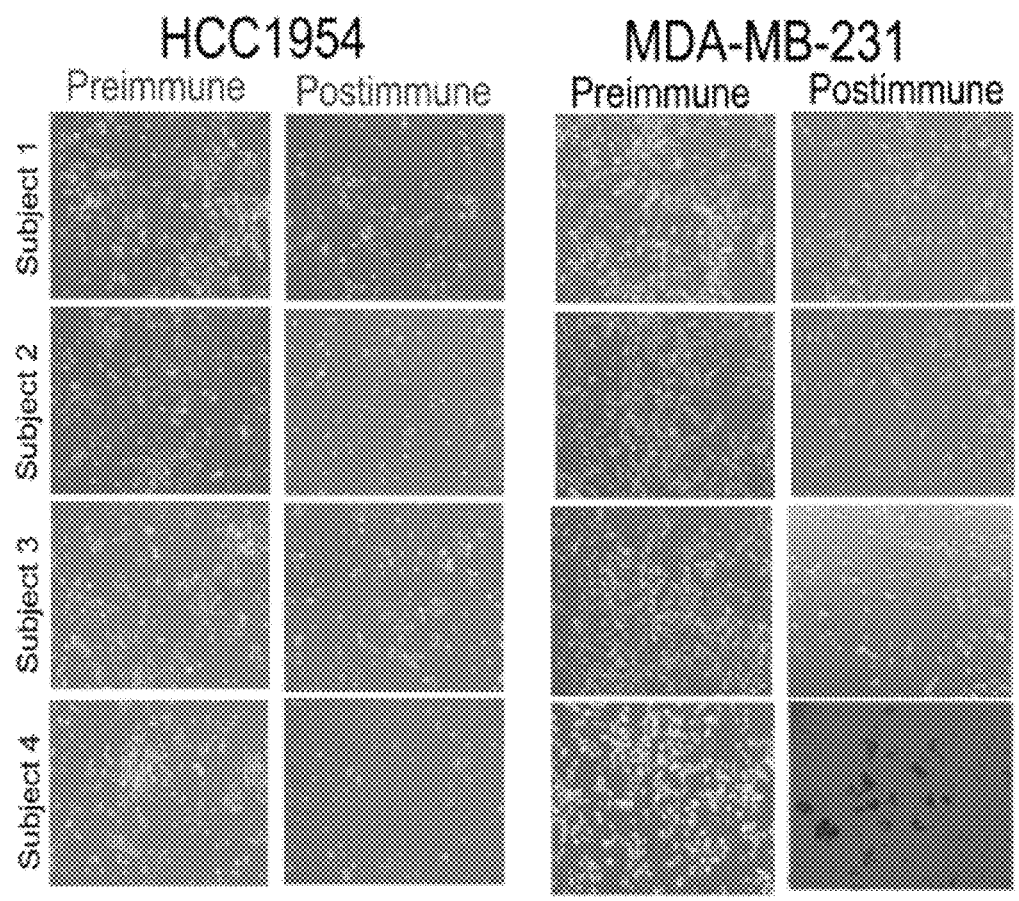
FIGS. 8A and 8B contains data showing the cytotoxic effect on HCC1954 cells and MDA-MB-231 cells that pre-immunization plasma and post-immunization plasma collected from 4 patients (subjects 1-4) in the Phase I trial of P10s-PADRE.
Figure 8B:
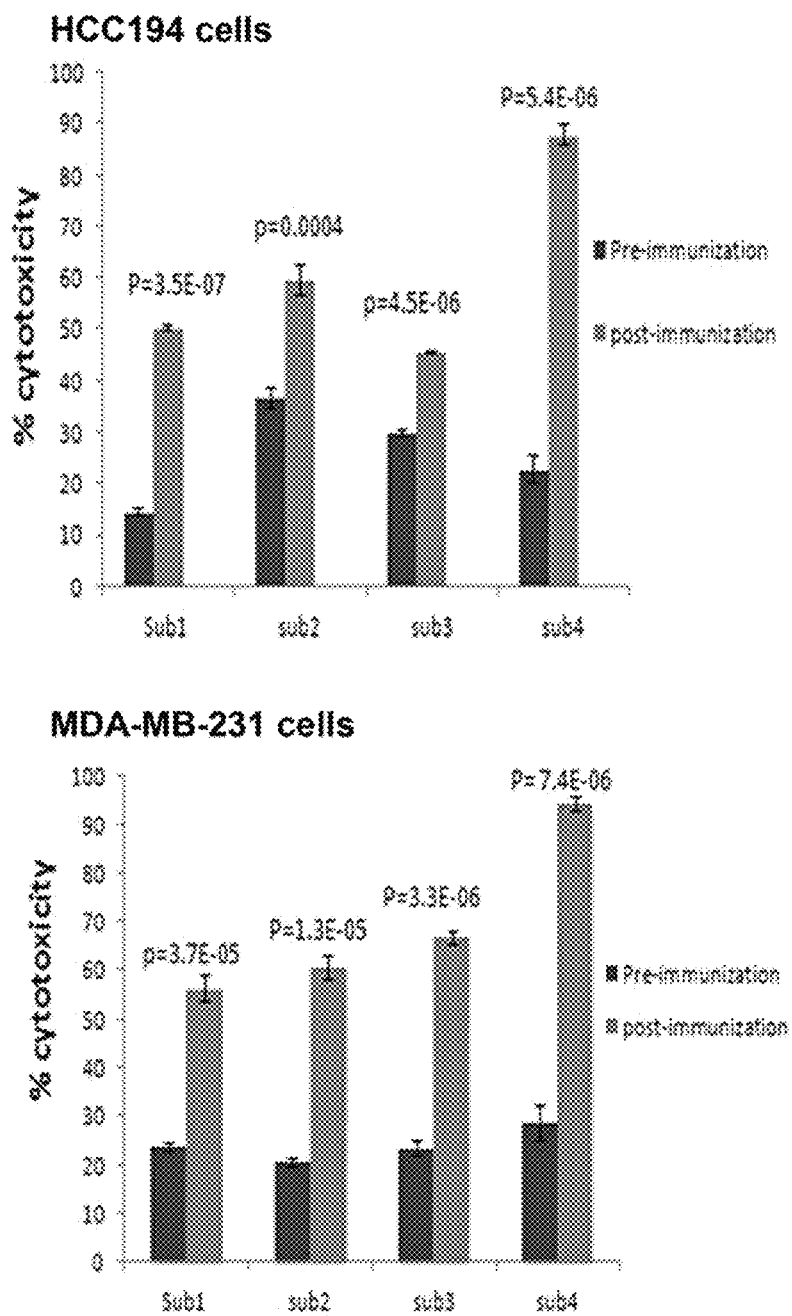

FIGS. 8A and 8B show the cytotoxic effect of pre- and post-immunization plasma collected from 4 patients on HCC1954 and MDA-MB-231 cells. FIG. 8A shows that the immunized subjects generated an immune response to P10s and that the induced serum and plasma antibodies bind and are cytotoxic to MDA-MB-231 and the de novo Trastuzamab-resistant HCC1954 cell lines. Cytotoxicity in each cell line was also quantified by counting cells remained in triplicate wells and presented in the bar graph in FIG. 8B.

Figure 9:
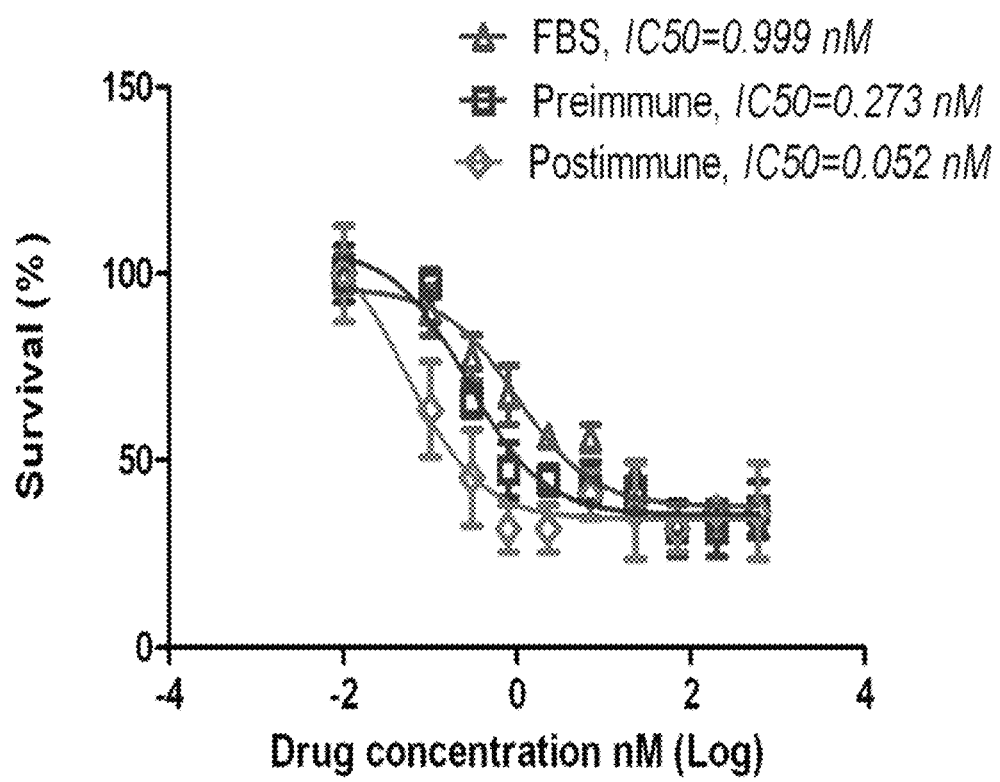
FIG. 9 contains data comparing the effect of pre-incubation of MDA-MB-231 cells with pre-immunization serum and post-immunization serum collected from one patient in the Phase I trial of P10s-PADRE on tumor cell sensitivity to docetaxel toxicity. The data show pre-incubation of MDA-MB-231 cells with the patients post-immunization serum sensitized tumor cells to docetaxel toxicity. MDA-MB-231 cells were cultured in RPMI medium containing 10% FBS overnight. Medium was then replaced with one that contained either pre-immune serum or post-immune serum. FBS was used as control. After 5 hours of incubation, docetaxel was added in serial dilutions into wells. 24 hours later wells were washed and live cells were fixed, stained and counted. Percentage of survival was calculated as the ratio of cell number at a given drug dose to the cell number at the "0" drug dose. Prism 5 software was used to fit dose response curves using survival data. $IC_{50}$ of each curve was calculated. The $IC_{50}$ of post-immune serum is significantly different from the $IC_{50}$ of FBS and the $IC_{50}$ of pre-immune serum, with P values of 6.21E-08 and 0.002, respectively.

As shown by data in FIG. 9, preliminary studies suggest that the induced antibodies can sensitize tumor cells to docetaxel treatment. FIG. 9 shows preincubation with subject's serum sensitized tumor cells to docetaxel toxicity. MDA-MB-231 cells were cultured in RPMI medium containing 10% FBS overnight. Medium was then replaced with one that contained pre or post-immune sera. FBS was used as control. After 5 hours of incubation docetaxel was added in serial dilutions into wells. 24 hours later wells were washed and live cells were fixed, stained and counted. Percentage of survival was calculated as the ratio of cell number at a given drug dose to the cell number at the "0" drug dose. Prism 5 software was used to fit dose response curves using survival data. IC$_{50}$ of each curve was calculated. Post-immune IC$_{50}$ is significantly different that FBS and Pre-immune IC$_{50}$s, with P values of 6.21E-08 and 0.002, respectively.

The 5th subject is almost completed with her immunization scheme at the 500 ug dose and the 6th subject has received two immunizations at 500 ug—completing the 500 ug cohort.

Example 4

The Phase I first-in-man dose-escalation trial testing P10s-PADRE in stage IV breast cancer patients was successfully completed. P10s-PADRE was formulated with MONTANIDE™ ISA 51 VG. Doses of P10s-PADRE that were tested were 300 μg/injection and 500 μg/injection.

Methods

Study Design and Statistical Considerations

A Phase I dose-escalation trial was conducted to assess the safety and tolerability of the vaccine, P10s-PADRE, in subjects with Stage IV breast cancer. This trial, which utilized the conventional 3+3 cohort design (Rosenberger, W. F. and Haines, L. M. Competing designs for phase I clinical trials: a review. Stat Med. 21, 2757-2770. (2002)), was approved by the Institutional Review Board (IRB) of the University of Arkansas for Medical Sciences (UAMS), and was registered with the NIH clinical-trials registry at the US FDA clinicaltrials [dot] gov website.

The trial was designed as a dose-escalation study using what have been called "standard" or "conventional" methods (Rosenberger, W. F. and Haines, L. M. (2002) Supra). Subjects were treated in groups of three, the first at the initial dose of 300 μg P10s-PADRE per injection. If there were no dose-limiting toxicities (DLTs) in this first group, the final dose would escalate to 500 μg P10s-PADRE per injection, and the next group treated at this final dose. If there were two or three DLTs in the first group, the dose would de-escalate to a safety dose of 100 μg per injection, and treat three patients at this safety dose. If there were exactly one DLT in the first group, three more patients would be vaccinated at the initial dose, and escalate to the final dose only if no additional DLTs were observed. Assessment of safety in this manner was the primary outcome. All other endpoints were deemed to be secondary, and their analysis to be exploratory and hypothesis-generating. All patients were included in the safety and efficacy analyses.

Endpoint titers of anti-P10s antibodies were analyzed for changes with respect to time, dose cohort, and their interaction using the nonparametric repeated-measures method of Brunner et al. (Nonparametric Analysis of Longitudinal Data in Factorial Experiments. (John Wiley & Sons, Inc. New York, N.Y.; 2002)) and in particular, using the recommended ANOVA-type statistics from this method. The effect of vaccination on plasma cytotoxicity towards a cell line was evaluated by one-sample t-test on paired differences. All statistical tests were two-sided, and employed a P<0.05 significance level. SAS version 9.3 (the SAS Institute, Cary, N.C.) was used for the nonparametric repeated-measures analysis, whereas GraphPad Prism5 (GraphPad Software, Inc., La Jolla, Calif.) was used for the one-sample t-tests and for all graphs.

Participants

The P10s-PADRE vaccine was developed for, inter alia, treatment of breast cancer patients with high risk of disease relapse. In the Phase I trial, research participants were restricted to females with histological or cytological confirmed stage IV breast cancer. Women 18 years of age or older, of all races, with histologically or cytologically confirmed stage IV breast cancer were eligible, and subjects were enrolled after providing written, informed consent. Disease staging was done according to the American Joint Commission on Cancer (AJCC), sixth edition. The following eligibility criteria were used: The cancer may have been newly diagnosed metastatic or relapsed after primary or adjuvant therapy and must not have required a treatment change for 2 months. Treatments with anti-estrogen therapy or chemotherapy were allowed. The chemotherapy regimen could not contain steroids in the pre- or post-supportive-care medications. Additional eligibility criteria included: an Eastern Cooperative Oncology Group performance status of 0-1 and adequate organ function (white blood cell count ≥3,000/mm3, hemoglobin ≥8.0 g/dL, platelets ≥100,000/mm$^3$ within 2 weeks prior to registration, total bilirubin ≤3.0 mg/dL, aspartate aminotransferase ≤200 IU/L, alanine aminotransferase ≤200 IU/L, and serum creatinine ≤1.5-/dL). Subjects had to be immunocompetent as measured by responsiveness to two recall antigens by skin testing. The following exclusion criteria were applied: known brain metastasis; pregnancy or lactation; known history of HIV infection; clinically serious infection; severe cardiac insufficiency; other active malignancy; history of organ allograft; immunodeficiency or history of splenectomy; concurrent treatment with steroids or immunosuppressive agents; and unsuitability for the trial, based on clinical judgment.

Procedures

P10s-PADRE vaccine was produced as follows. Peptide P10s (WRYTAPVHLGDG—SEQ ID NO:1) was covalently attached to a version of Pan T cell peptide PADRE (dAKchAVAAWTLKAAdA: AmbioPharm, Inc., North Augusta, S.C., USA). The peptide was synthesized according to Good Manufacturing Practice guidelines. The peptide vaccine was emulsified with the adjuvant Montanide ISA-51VG, (SEPPIC, Inc., Fairfield, N.J., USA).

Vaccine was administered in liquid form by subcutaneous (SC) injections on 5 separate occasions during Weeks 1, 2, 3, 7, and 19. Administration of each dose to 3 patients was planned. Initially, a single cohort was administered P10s-PADRE (300 μg/mL) formulated with MONTANIDE™ ISA 51 VG. Doses of P10s-PADRE admixed with MONTANIDE™ ISA 51 VG were administered to subjects subcutaneously in rotating injection sites in the abdomen.

The primary endpoint was the safety of peptide vaccination. The secondary endpoints were anti-P10s antibody titers, antibody binding to breast-cancer cells, and sample cytotoxicity towards breast-cancer cells.

The presence of anti-P10s antibodies in the sera of patients before and after vaccination was assessed with ELISA. ELISA plates were coated with 1 μg/well of the multiple-antigen peptide (MAP) version of P10s in carbonate-bicarbonate buffer (Sigma-Aldrich, St. Louis, Mo.) overnight. Serial 2-fold dilutions of plasma and serum samples, from 1:100 (dilution step 0) to a final dilution of 1:12800 (dilution step 7), were added after blocking wells with PBS containing 0.5% FBS and 0.2% Tween 20 (Blocking buffer) for 1 h at 37° C. Serum dilutions in blocking buffer were incubated for two hours at 37° C. After washing, wells were incubated with HRP-conjugated mouse anti-human IgM and IgG (Sigma-Aldrich) for 1 hour at 37° C. Then Tetramethylbenzidine substrate (Sigma-Aldrich) was added and the reaction was stopped after 20 minutes. Plates were read using an ELISA reader at 450 nM.

The resulting absorbance-versus-dilution curves were used to estimate normalized endpoint titers as follows. (1) A linear regression of absorbance versus dilution step was performed on the serial dilutions of each sample from each subject, in which dilution steps were numbered as described above. (2) The intercept of the regression line for each subject's pre-immune sample was the value used as the absorbance cutoff for determining the endpoint titers of all samples collected from that subject. (3) The dilution step where each sample's regression line crossed the subject's absorbance cutoff was determined and called X(c), and the normalized endpoint titer was estimated from X(c) as Titer=1:($100*2^{X(c)}$). This procedure normalized each subject's pre-immune titer to be 1:100. To prevent extrapolation too far outside the range of dilution steps, values of X(c) less than −1 or greater than +8 were set equal to −1 and +8, respectively; this caused normalized endpoint titers to have minimums of 1:50 and maximums of 1:25600.

The functionality of subjects' antibodies on human breast-cancer cell lines before and after vaccination was assessed. Human breast-cancer cell lines were purchased from ATCC (Manassas, Va.). Cells were cultured in a base medium supplemented with 10% heat-inactivated fetal bovine serum (Life Technologies), 50 units/mL penicillin, and 50 µg/mL streptomycin. Base media for MDA-MB-231 and HCC1954 were DMEM and RPMI (both from Fisher Scientific, Pittsburgh, Pa.), respectively. To assess the cytotoxicity of subjects' samples towards the cell lines, $5 \times 10^4$ (24-well plate) of the respective cells were seeded in medium containing 10% FBS. After 24 hours, the medium was refreshed with media containing 10% pre-immune or post-immune plasma. Medium in control wells contained 10% FBS. 24 hours after addition of plasma, supernatants were removed, live cells fixed and stained with Crystal violet. Percentage of cytotoxicity was calculated as 100% minus the percentage of cells surviving relative to the number of cells in control wells. All samples were assayed in triplicate, and the average of the triplicates was taken to be the sample's measured cytotoxicity.

Results

Patient Characteristics

The study accommodated screening for 24 human subjects to allow an enrollment goal of 18 subjects if required by the conventional 3+3 design. In this design, a minimum of 6 subjects would be needed if no toxicities occurred. Table 1 lists the sixteen subjects consented into the study, tabulated by age and race. Six subjects (37.5%) failed screening because of a lack of delayed-type hypersensitive (DTH) response to the recall antigens *Trichophyton* and *Candida* antigen. Only one subject (39610) declined to continue with the study, and never completed pre-study/screening to determine eligibility. Two cohorts of three-six stage IV breast cancer patients were enrolled successfully and completed their immunization course of 5 immunizations over 23 weeks hyperimmunization on weeks 1, 2, and 3, another immunization on week 7, and a boost immunization at week 19. A summary of the subjects' status and clinical response to the P10s-PADRE vaccination is listed in Table 2.

Immunization with P10s-PADRE Induces an Anti-P10s Response

Figure 10:
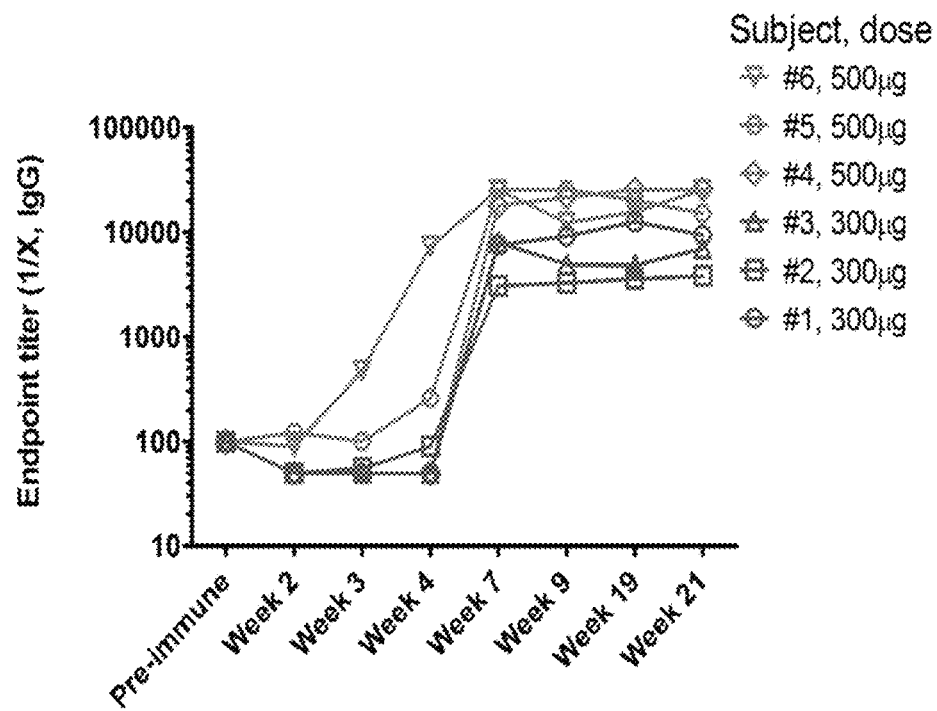
FIG. 10 contains data from experiments investigating reactivity of antibodies against P10s induced in human patients by the P10s-PADRE vaccine in the Phase I trial of P10s-PADRE. ELISA plates were coated with a MAP version of P10s and reactivity of two-fold serial dilutions of pre-immune sera and post-immune sera from trial subjects was detected by HRP-conjugated anti-human IgG. Normalized serum endpoint titers for vaccinated subjects are shown for every blood draw week. Immunization led to a significant increase in normalized endpoint titers, and subjects immunized with higher peptide dose showed higher titers. Normalized endpoint titers were estimated as described below.

The P10s-PADRE vaccine proved to be safe and tolerable and the immunization schedule feasible. P10s-PADRE vaccine-immunized subjects generated an immune response to a MAP form of P10s and all six subjects who received the P10s-PADRE vaccine formulation displayed a persistent IgG response to P10s MAP peptide form after immunization as measured by ELISA assay (FIG. 10). A similar binding pattern to the MAP peptide was observed using plasma samples. Anti-peptide serum reactivity surged dramatically from week 4 to week 7 of the study in most subjects except in subject #6, in whom it was already surging at week 4. The increases at week 7 compared to pre-immune ranged from 31 folds (in subject #2) to 256 folds (in subjects #5 and #6), and the titers in subsequent weeks showed little change from their week-7 values. The cohort immunized with the higher dose of vaccine displayed higher normalized endpoint titers (FIG. 10). In nonparametric repeated-measures analysis, the main effects of dose and week were statistically significant (both P values <0.0001), but the dose×week interaction was not (P=0.40) (Table 3). Further evaluation of the immune response in three subjects suggest that the anti-P10s titer starts to drop one year after the last immunization for some of the subjects.

Figure 11A:
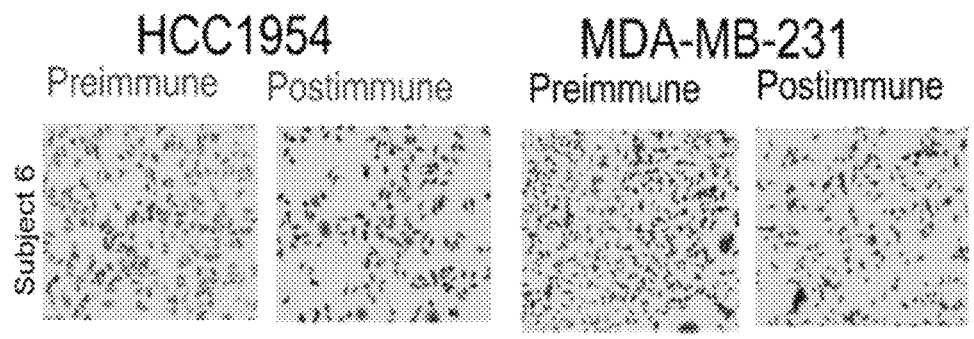
FIGS. 11A and 11B contains data showing cytotoxicity of antibodies induced in the Phase I trial of P10s-PADRE by the P10s-PADRE vaccine.
Figure 11B:
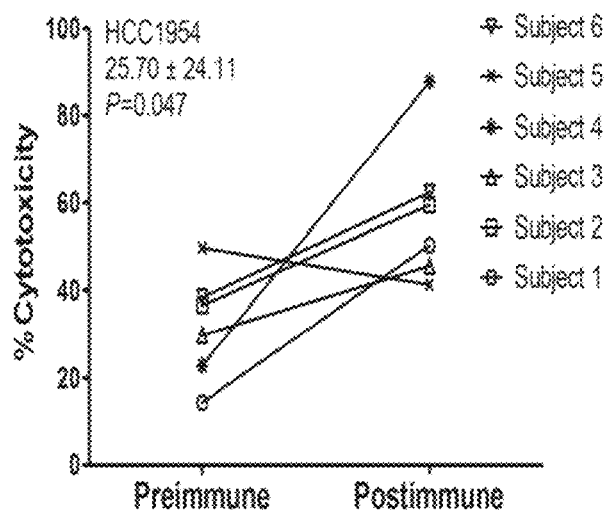
Figure 11B:
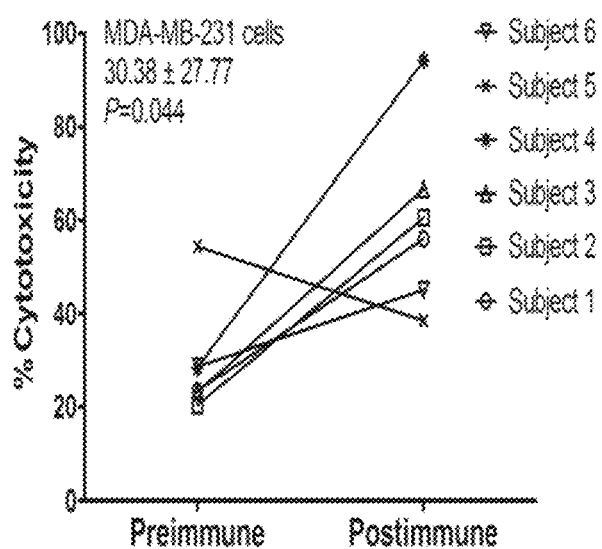
Figure 12:
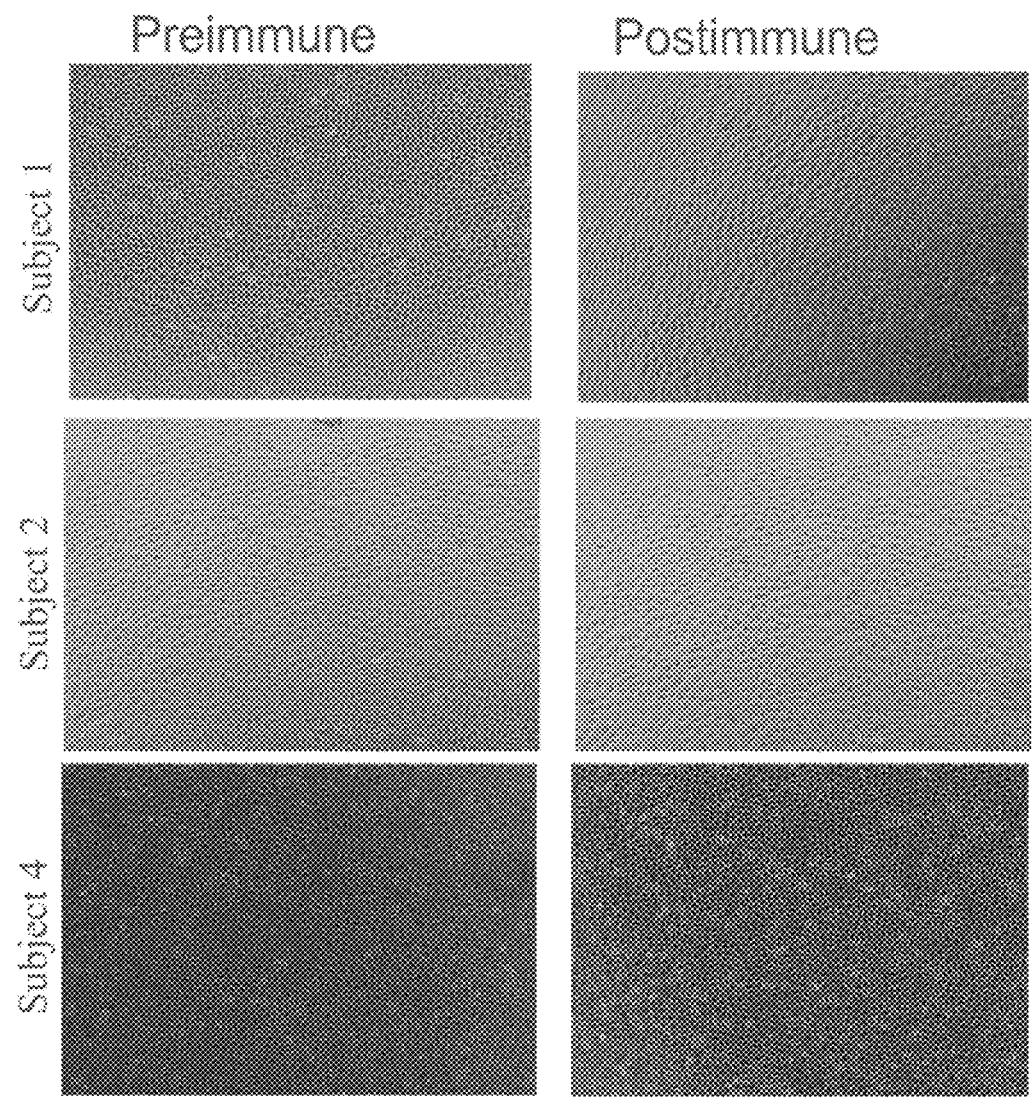
FIG. 12 contains data showing that no cytotoxic effect was observed when pre-immunization plasma and post-immunization plasma collected from subjects in in the Phase I trial of P10s-PADRE was contacted with MCF-10A cells. Pictures were taken after 24 hours of incubation with 10% plasma of the indicated subjects. Extension of incubation time up to 72 hours in separate experiments did not affect viability of cells.

P10s-PADRE Immunization has a Cytotoxic Effect on Human Breast Cancer Cell Lines Vaccine induced antibodies displayed a significant average increase in cytotoxicity. Immunization with P10s-PADRE led to cytotoxic activity against two human Breast cancer cell lines that are resistant to systemic therapy. MDA-MB-231 cells are representative of basal-like carcinoma, whereas HCC1954 cells express HER2, but nonetheless have a de novo resistance to Trastuzumab (FIGS. 8A and 11A). Cytotoxicity toward both cell lines was higher in the post-immune plasma from 5 of the 6 subjects compared to their pre-immune plasma. The post-immune increases in cytotoxicity among the 6 subjects had an average (standard deviation) of 26% (24%) towards HCC1954, and 30% (28%) towards MDA-MB-231, and both increases were statistically significant (P=0.047 and P=0.044, respectively) via one-sample t-test (FIG. 11B). No toxicity was observed on MCF-10A, which is a non-tumorigenic human breast epithelial cell line (FIG. 12). In other experiments, no toxicity was observed against MCF-7 cells, but toxicity was observe against cells of ZR-75-1, a slow-growing ER+ cell line like MCF-7 that is considered, however, to have intact caspase-3 functionality unlike MCF-7.

Discussion

No dose-limiting toxicity was observed in this study. Determination of the maximum tolerated dose of peptide was hampered because of the potential of forming granulomas due to the nature of the adjuvant.

The vaccine was administered to patients who met all eligibility criteria including the ability to mount a response to two recall antigens by skin testing. The rationale for this latter criterion was to select those patients who have an active immune system capable of reacting to antigenic challenges. Six patients of 16 screened met all criteria (37.5%) while the rest were considered screen failures mostly because of negative recall-antigen skin tests. All patients enrolled on the study showed evidence of reactivity to the P10s-PADRE vaccine regardless of the type of breast cancer, which suggests that the future development of this vaccine may be pursued in all types of breast cancer.

The primary endpoints of this study were assessment of the feasibility and safety of vaccination, but immune responses generated by immunization with P10s-PADRE were analyzed for features relevant to immunotherapy. The P10s-PADRE vaccine induced P10s-reactive antibodies in all subjects. Observations confirmed that the immunization with P10s-PADRE is 100% feasible as defined by the rate of subjects who received all five immunizations on schedule. Evaluation of the antibody response to P10s suggests that the 500 µg dose may produce higher titers of anti-P10s IgG than the 300 µg dose, although the small cohort sizes and lack of randomization preclude firmer conclusions regarding a dose effect. The titer analysis further suggests that only 3 immunizations are sufficient to generate an effective immune response with IgG titers sustained from week 7. Moreover, since no toxicities were seen in subjects at the 500 µg dose, but concerns exist about excessive adjuvant-related skin reaction with higher doses, it is deemed prudent to recommend 500 µg per injection in future studies.

P10s-generated antibodies from 5 of the 6 subjects proved cytotoxic on two human breast cancer cell lines that are considered representative of the extreme resistance to standard systemic therapy. No cytotoxicity was observed on the normal epithelial cell line MCF10A, which indicates specificity towards cancer cells of the generated antibodies. Increased β1,6-branching, and increased TACA expression that includes their clustering on cell surfaces differentiate tumor cells from normal cells. The expression profile of commonly observed N-linked and O-linked glycans of carcinoma cells, which is different from normal tissue, is associated with poor prognosis. The induced antibodies from humans vaccinated with P10s-PADRE distinguish this differential expression, as evidenced from the lack of immunopathology in mouse studies and the non-cytotoxic effect on MC-F10A cells (Monzavi-Karbassi, B. et al. (2007) Supra; Hennings, L. et al. (2011) Supra).

Induction of immune responses that result in tumor cell death is useful in immune therapy that targets cancer-cell dissemination. In addition, induction of immune responses that interfere with signaling mechanisms associated with TACA expression profiles may stop the growth of tumors, and prevent the development of metastases. Furthermore, it is postulated that anti-carbohydrate antibodies are a part of immune-surveillance mechanisms that are cytostatic or cytotoxic (Vollmers, H P and S Brandlein, Natural antibodies and cancer. N Biotechnol 25, 294-298. Epub 29 Apr. 2011. (2009)). Accordingly, induction of immune responses may have a beneficial effect on the course of malignant disease and long-term patient survival.

P10s-PADRE-induced antibodies in serum and plasma were reactive with, and cytotoxic to human breast-cancer cell lines that represent the extremes of therapeutic resistance. ZR-75-1 cells were also susceptible to toxicity but MCF-7 cells were not indicating a mechanism which may include the caspase-3 pathway. Anti-TACA antibodies in the sera were polyclonal and shown to exert an in vitro cytotoxic effect. Anti-TACA antibodies may augment the effect of the immune system against tumor cells. Furthermore, anti-TACA antibodies may sensitize tumor cells for more efficient activity of combined cytotoxic agents or radiation therapy, for example by interruption of signaling pathways such as the focal adhesion-kinase pathway.

TABLE 1

Summary of study recruitment

| Subject | Reason for screen failure | Age | Race |
|---|---|---|---|
| 39601 | N/A | 77 | Caucasian |
| 39602 | Elevated SGOT | 61 | Caucasian |
| 39603 | N/A | 46 | Caucasian |
| 39604 | N/A | 50 | Caucasian |
| 39605 | No reaction to DTH skin test | 67 | Caucasian |
| 39606 | No reaction to DTH skin test | 62 | Caucasian |
| 39607 | No reaction to DTH skin test | 54 | Caucasian |
| 39608 | N/A | 50 | Caucasian |
| 39609 | N/A | 67 | African American |
| 39610 | Patient declined due to number of trips required | 44 | Caucasian |
| 39611 | No reaction to DTH skin test | 67 | Caucasian |
| 39612 | No reaction to DTH skin test | 62 | Unknown |
| 39613 | Progressive disease with treatment change | 44 | Caucasian |
| 39614 | No reaction to DTH skin test | 73 | Caucasian |
| 39615 | Withdrawn by PI before enrollment | 65 | Caucasian |
| 39616 | N/A | 51 | Caucasian |

TABLE 2

Patient characteristics, chemotherapy drug, and immune and clinical response.

| Dose of peptide (μg) per vaccination | Subject | ER/PR/Her2 status | PS* | Chemotherapy (dose) | Disease Progression | Immune responses Immunized plasma binding to MAP (ELISA) | Immunized plasma toxicity on cancer cells |
|---|---|---|---|---|---|---|---|
| 300 | 39601 (#1) | +/+/− | 0 | Denosumab (120 mg) | Stable | Yes | Yes |
|  | 39603 (#2) | +/−/− | 0 | Carboplatin (423 mg) and Gemcitabine (1395 mg) | Progressed | Yes | Yes |
|  | 39604 (#3) | +/−/+ | 0 | Vinorelbine (43 mg) and Trastuzumab (141 mg) | Stable | Yes | Yes |
| 500 | 39608 (#4) | +/+/− | 1 | Zometa (4 mg) | Stable | Yes | Yes |
|  | 39609 (#5) | +/−/− | 0 | Faslodex (500 mg) | Stable | Yes | No† |
|  | 39616 (#6) | −/−/+ | 0 | Trastuzumab (346 mg) | Stable | Yes | Yes |

†Due to high background toxicity in preimmune plasma from this subject, no significant increase in plasma toxicity was observed. A close look at the subject's calendar indicated that a Faslodex dose was applied two days before her preimmune blood draw.
*Performance status(ECOG)

TABLE 3

Non-parametric repeated-measures analysis of endpoint titer with Dose as the between-subject effect and Week as the within-subject effect.

| Source | DF† | F‡ | P-value |
|---|---|---|---|
| Dose | 1 | 38.9 | <0.0001 |
| Week | 2.93 | 27.22 | <0.0001 |
| Dose × Week | 2.93 | 0.98 | 0.40 |

†Degrees of Freedom of
‡the ANOVA-Type Statistic of Brunner et al. which approximately follows the central F(DF, ∞)-distribution.

Example 5

Clinical Response of a Breast Cancer Patient after Mimotope-Based Immunotherapy

The following disclosure refers to the unusual disease course and response to treatment by patient with metastatic HER2+ Breast Cancer who participated in the Phase I trial and was vaccinated with the P10s-PADRE vaccine formulation.

Methods and Results

The patient was originally diagnosed with breast cancer at age 45 when a routine mammogram showed suspicious calcifications on the left breast confirmed by a core biopsy as invasive ductal carcinoma.

At Time 0, the patient underwent bilateral skin sparing mastectomy with sentinel lymph node biopsy (SLNB) followed by bilateral saline implant reconstruction. Final pathology showed no cancer in the right breast and a 4 cm invasive ductal carcinoma in the left breast; grade III, with lymphovascular invasion. Margins were negative. Estrogen receptor (ER) was weakly positive and progesterone receptor (PR) was negative. HER2 was amplified by FISH. Left SLNB was negative. PET scan was negative for systemic metastases but paratracheal, paraesophageal and hilar lymph nodes were prominent. It was believed that these were not related to metastatic disease, however, because there were calcified lymph nodes in the area.

At Time 2 months (two months after Time 0), the patient began adjuvant chemotherapy with dose dense Adriamycin/Cyclophosphamide (60/600 mg/m$^2$ every two weeks for four cycles followed by Paclitaxel (175 mg/m$^2$) every two weeks for four cycles. Weekly Trastuzumab treatment was started at the same time with Paclitaxel and continued for a total of one year. The patient was also treated with Tamoxifen after the completion of chemotherapy and while taking the Trastuzumab. Yearly PET scans were obtained to check on the enlarged lymph nodes and showed complete regression.

At Time 34 months, the patient had a local recurrence with 1 cm mass on the left chest wall near the implant. This was resected to negative margins. The mass was ER positive, PR negative and HER2 positive with CEP17/HER2 ratio of 15. The patient was treated with radiation therapy to the area. Staging scans showed no evidence of metastatic disease.

At Time 52 months, a PET scan showed new small lung nodules scattered in both fields and biopsy-positive left subpectoral lymph node. The patient was treated with Vinorelbine and Trastuzumab (VT) and subsequent PET scans showed partial response in the lungs and complete resolution of the subpectoral lymph node. At that time, the patient was offered participation in the P10s-PADRE vaccine trial as her disease was considered stable. The patient was evaluated and deemed eligible for participation in the vaccine study.

At Time 58 months, the patient received her first subcutaneous injection of the vaccine of 300 mcg followed by similar doses on days 8, 15, 43 and 126 as per protocol, while continuing her standard treatment of VT.

Immune Response to P10s-PADRE Vaccine

Figure 13:
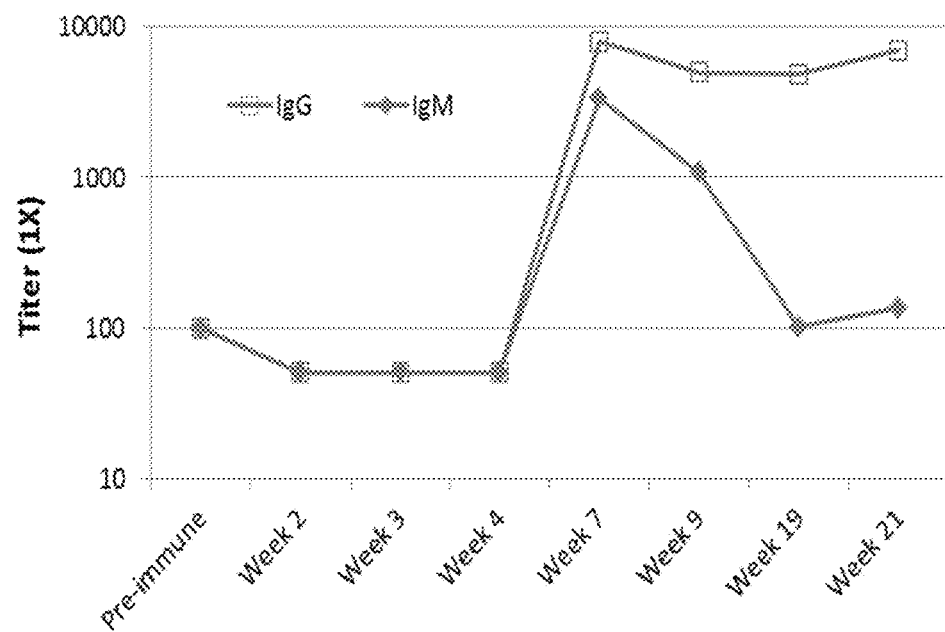
FIG. 13 contains data from the Phase I trial of P10s-PADRE showing reactivity of IgM and IgG antibodies induced in the vaccination of the patient with P10s-PADRE vaccine as discussed in Example 5. IgM and IgG fractions of serum antibodies from the immunized patient bind to MAP form of P10s in ELISA assays. ELISA plates were coated with 1 μg/well of the P10s MAP peptide in carbonate-bicarbonate buffer overnight. Serial dilutions were added after blocking wells in PBS containing 0.5% FBS and 0.2% Tween 20 for 1 h at 37° C. Serum dilutions were incubated for two hours at 37° C. After washing, wells were incubated with HRP-conjugated mouse anti-human IgM and IgG for 1 hour at 37° C., then substrate was added and the reaction was stopped after 20 minutes. Plates were read by an ELISA reader at 450 nM. Titers were estimated from absorbance-versus-dilution curves by linear regression. The intercept of the regression line for each subject's pre-immune serum was defined as the absorbance cutoff for determining end-point titer for that subject, and the dilution where each sample's regression line crossed the subject's absorbance cutoff was defined to be the sample's end-point titer. Extrapolation beyond one dilution below the minimum or above the maximum actual dilutions was not allowed. This procedure normalized each subject's pre-immune titer to be 1:100, and subjects with a 10-fold or greater increase in end-point titer over the 1:100 titer are considered responders.

The patient generated an immune response to P10s Multiple Antigen Peptide (MAP). An increase in both IgM and IgG binding to the MAP peptide after immunization was observed by ELISA assay (FIG. 13). Both anti-peptide IgM and IgG peaked at week seven of the study. IgM was short-lived and returned back to the baseline by week 19, however, the activity of the IgG portion remained high.

Figure 14A:
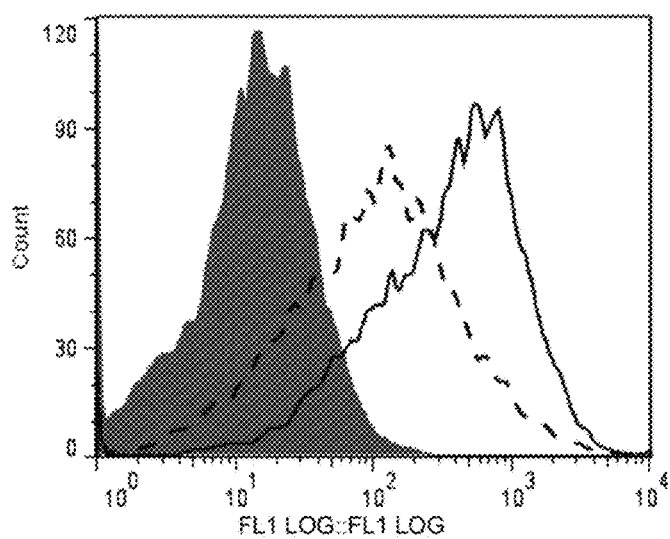
FIGS. 14A and 14B contain data from experiments that study cytotoxicity of antibodies induced by the P10s-PADRE vaccine in Phase I trial of P10s-PADRE in the patient as discussed in Example 5. The data show that P10s-PADRE induced IgG serum antibodies from the patient discussed in Example 5 bind to HCC1954 cells and stimulate cell death. HCC1954 cells were harvested with enzyme-free buffer, washed and incubated with pre-immune sera or post-immune sera collected from the patient at Week 7. Binding of IgG antibodies in the sera to HCC1954 cells was visualized with an FITC-conjugated mouse anti-human IgG.
Figure 14B:
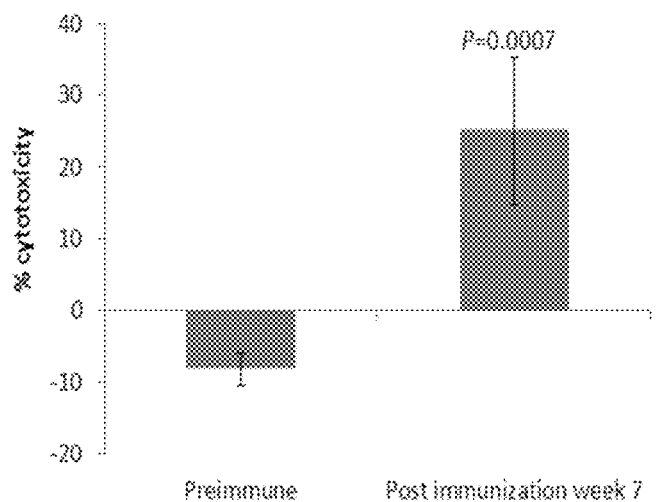

P10s-PADRE vaccine-induced serum bound to the HCC1954 cell line (FIG. 14A) and incubation of HCC1954 cells with post-immunization serum collected at week 7 led to significant stimulation of cell death (FIG. 14B). Incubation of HCC1954 cells with pre-immunization serum showed that pre-immunization serum had no corresponding cytotoxic effect.

Figure 15:
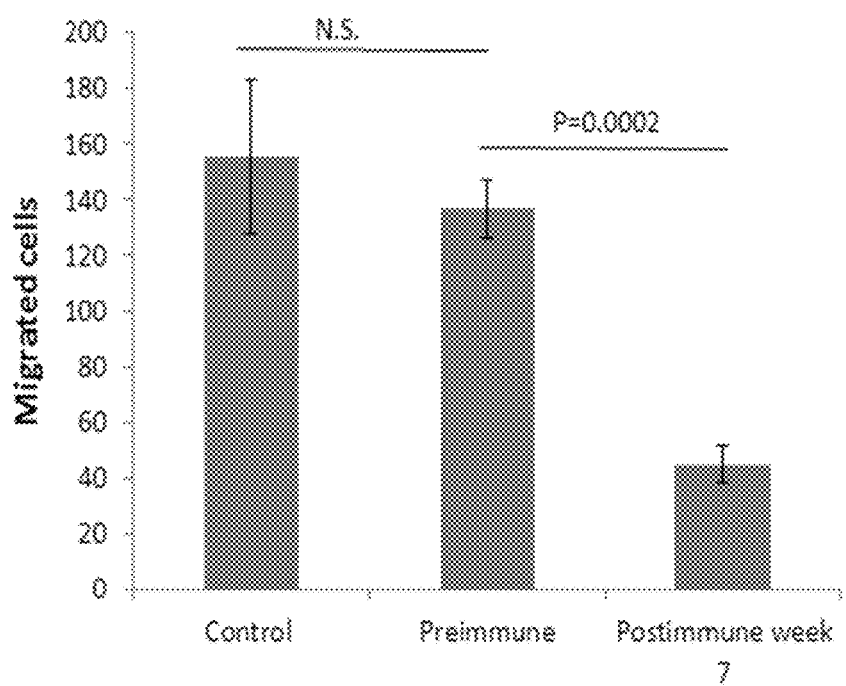
FIG. 15 contains data from experiments comparing inhibition of migration of HCC1954 cells by serum collected from the patient before P10s-PADRE immunization to serum collected from the patient collected 7 weeks after P10s-PADRE immunization in the P10s-PADRE vaccine in Phase I trial and discussed in Example 5. Cells were starved overnight and then harvested and mixed with either pre-immune serum or postimmune serum. The cell-serum mixtures were incubated in transwells for 20 hours. The cells were then stained and those on the surface were wiped out. Migrated cells were then visualized under a light microscope and counted. Average over three replications with SD are shown.
Figure 16:
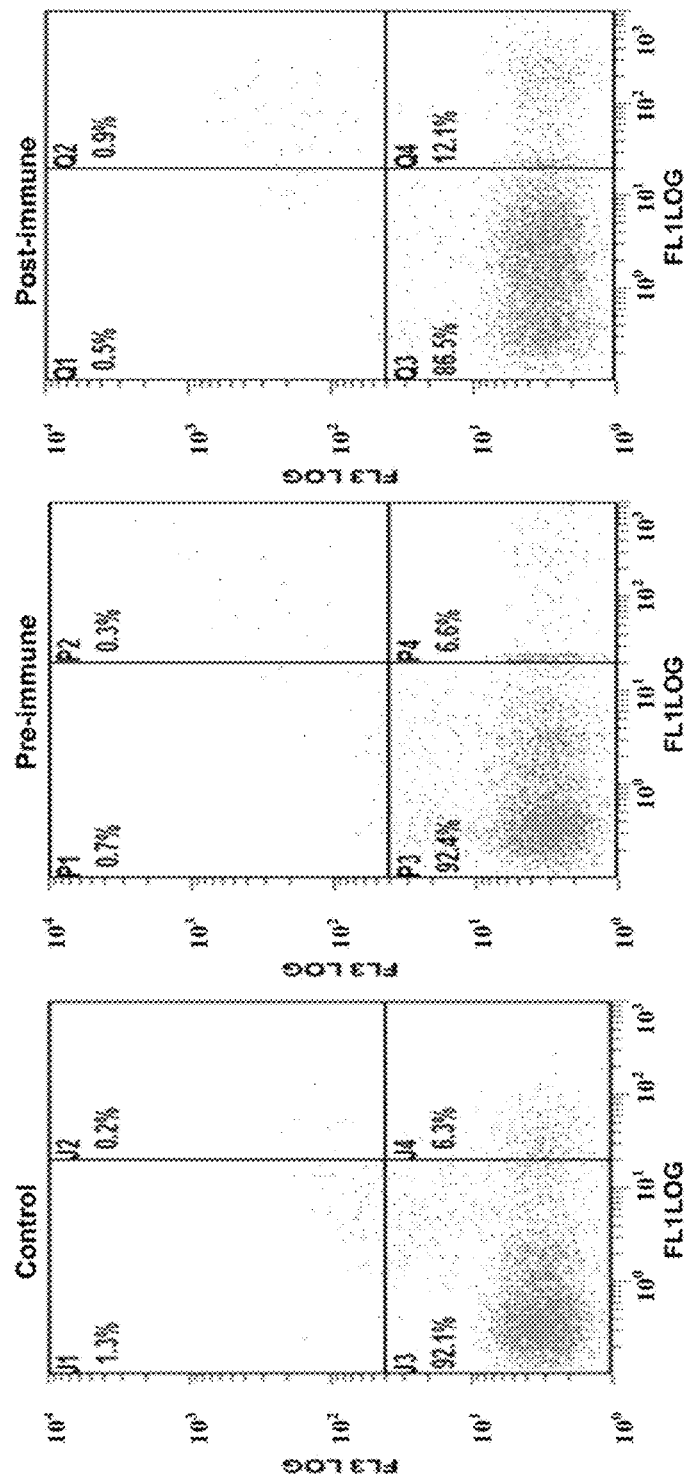
FIG. 16 contain data from experiments discussed in Example 5 that study pre-immune serum induced apoptosis in MDA-MB-231 cells and post-immune serum induced apoptosis in MDA-MB-231 cells. Cells were incubated with 10% FBS (control) or either pre-immune or post-immune sera overnight and then harvested and stained with annexin V-FITC (FL1) and propidium iodide (FL3). Quadrants J4, P4 and Q4 show apoptotic cells in control, pre-immune serum treated and post-immune serum treated cells, respectively.

P10s-PADRE vaccine-induced serum also inhibited the migration of HCC1954 cells (FIG. 15). Plasma was later tested in binding and observed a very similar pattern of reactivity. Post immune plasma was cytotoxic to both HCC1954 and MDA-MB-231 cell lines (See data for subject 3 in FIGS. 8A and 8B). In a separate experiment, live cells were harvested after overnight incubation with sera and examined induction of apoptosis by detecting annexin expression. Results indicate that the anti-P10s serum induced apoptosis in MDA-MB-231 cells (FIG. 16). Binding and cytotoxic effect of serum and plasma on aggressive triple-negative MDA-MB-231 and the de novo Trastuzamab-resistant HCC1954 cell lines is of clear clinical potential for this vaccine. In particular, the observed cytotoxicity against HCC1954 suggests a potential positive outcome for the patient tested. Further studies suggested that the induced antibodies could sensitize tumor cells to docetaxel treatment (FIG. 9).

Patient's Clinical Status

Regression of Lung Metaseses.

Other than local reactions with indurations at the site of injections, the vaccine did not have any side effects. After vaccination started, serial PET scans initially showed increased fluorodeoxyglucose (FDG) activity in the previously known lung metastases without increase in their size or number, then decrease of the FDG activity while her systemic treatment remained the same.

Brain Lesions.

At Time 66 Months, she complained of left arm weakness and ataxia. MRI of the brain showed three well-defined complex cystic masses in the brain parenchyma with no vasogenic edema around them. At Time 68 Months, she underwent left suboccipital craniotomy for resection of left cerebellar hemisphere lesion, and left frontotemporal craniotomy for resection of left inferior temporal cystic lesion, followed by fractionated stereotactic radiation therapy to the cystic lesions followed by whole brain radiation therapy.

Specimens from the resection of the brain lesions show mainly superficial cortical fragments, with scattered white matter fragments. Cytokeratin (AE1/AE3) and CAM 5.2 immunohistochemistry, performed on both specimen parts, are negative for epithelial cells. Multiple additional sections (levels ×3), obtained on both specimen parts, showed no other findings. Scattered CD3+ T-cells, mainly associated with vessel lumina and hemorrhagic areas where present in the parenchyma, but the significance was not clear, though it likely did not indicate a significant inflammatory/infectious process. No CD20+ cells were observed, except for an occasional one in the vessels. Kappa and lambda light chains have high background, but there seems to be a stronger staining in the vessels, likely associated with the plasma, probably as would be expected normally. Together with the virtual absence of CD20+ cells, no cellular staining was identified in the parenchyma. CD56 was tested for to identify any possibly natural-killer cell population, and was diffusely positive in neural tissue, making it very difficult to interpret; however, no significant cells that were positive for this antibody were identified. In addition, after reviewing the slides in the light of this new information, no inflammatory, infectious or reactive changes were identified. Specifically, no viral inclusions, microglial proliferation or nodules, macrophages, reactive astrocytes or necrotic cells were identified. Therefore, the findings did not explain the nature of these cystic lesions described radiologically.

Her neurologic deficit recovered for the most part but she still has some lack of coordination in her left arm and difficulty with word finding. Otherwise, she was able to go back to work fulltime and her last MRI showed continued decrease in size of her lesions. She was switched to Docetaxel, Pertuzumab and Trastuzumab at Time 70 Months due to progression of her disease in the lungs. Her PET scan at Time 76 Months showed complete response in the lungs and lymph nodes.

Discussion

Induced immune responses can result in tumor cell death, including tumor cell death among tumor cells that are resistant to tumor cell death by other therapies. Resistance to tumor cell death is a key cause of treatment failure and can become the source for recurrence and metastatic disease.

The P10s-PADRE vaccine was developed as a broad-spectrum immunogen to induce responses to TACAs. The vaccine was shown to induce antibodies to P10s in subjects immunized with the vaccine and induced antibodies that bind to disparate representative human breast cancer cell lines, inhibiting migration, and mediating cytotoxicity.

Among the participants in the P10s-PADRE vaccine study was one with an unusual disease course. Fourteen weeks after she received the vaccine her PET scan showed increased uptake in her lung lesions without increase in their size. This was followed by improvement of her lung lesions six months later at the time that she was diagnosed with multiple brain lesions. An inflammatory response targeting the lung lesions and coinciding with the rise of the anti-P10 titers may have caused the increase in the uptake on PET scan in that area.

Anti-P10 IgM and IgG antibody titers peaked on week 7 after vaccination and remained high for the IgG while the IgM titers dropped to their baseline on week 19. At the time she was diagnosed with the brain lesions her lung metastases had returned to their baseline. Resection of two of the brain lesions showed no evidence of cancer. The third lesion was small and more solid and was treated by gamma knife. The changes in her lung lesions at that time were interpreted as not consistent with progression since their size had not changed. The brain lesions did not show any evidence of malignancy nor did they show evidence of inflammation. All the other subjects on the study were evaluated with MRIs of the brain and none showed similar lesions.

The immune response induced by the P10s-PADRE vaccine, such as the IgG antibodies, may sensitize tumor cells for more efficient activity of the Docetaxel, Pertuzumab and Trastuzumab (DPT) therapy by increasing sensitivity to Docetaxel and/or Pertuzumab and/or Trastuzumab. DPT activity is known to be sensitive to phosphorylation status of focal adhesion kinase (FAK) pathways. P10s-reactive antibodies may contribute to FAK silencing known to promote the in vitro efficacy of docetaxel in both taxane-sensitive and taxane-resistant cell lines and may serve as a novel therapeutic approach. The same is observed for Pertuzumab and for Trastuzumab. Effective treatment may include the combination of P10s-PADRE vaccine or antibodies induced by P10s-PADRE together with Docetaxel and/or Pertuzumab and/or Trastuzumab and/or other drugs such as those sensitive to phosphorylation status of focal adhesion kinase (FAK) pathways.

The invention claimed is:

1. A method of treating a human who has been diagnosed as having breast cancer, wherein the breast cancer is selected from the group consisting of i) triple negative breast cancer and ii) breast cancer that is HER2 positive, the method comprising administering to said human a composition comprising a compound having the structure of Formula 1:

Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH$_2$    Formula 1 wherein Ala13 and Ala25 are each D amino acids shown as dALa, and Ala at position 15 is cyclohexylalanine, a modified L configuration Alanine shown as CHAla.

2. The method of claim 1 further comprising treating the human with one or more anti-cancer chemotherapeutics, anti-cancer radioactive agent and/or with anti-cancer radiation therapy.

3. The method of claim 1 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

4. The method of claim 1, wherein a) the composition further comprises an anti-cancer chemotherapeutic or anti-cancer radioactive agent, or b) the composition is a component in a kit comprising a first container that comprises the composition and a second container comprising an anti-cancer chemotherapeutic or anti-cancer radioactive agent.

5. The method of claim 1 wherein the composition further comprises an adjuvant.

6. The method of claim 5 wherein the adjuvant is selected from the group consisting of an oil and surfactant adjuvant and QS21 adjuvant.

7. The method of claim 5 wherein the adjuvant is an oil and surfactant adjuvant, wherein the oil is mineral oil and the surfactant is mannide monooleate.

8. The method of claim 1 wherein the composition comprises the compound having the structure of Formula 1 in an amount selected from the group consisting of: at least 300 µg, at least 500 µg, and at least 1000 µg.

9. The method of claim 1 wherein the human is further treated with surgery and/or chemotherapy.

10. The method of treating a human who has been diagnosed as having triple negative breast cancer, the method comprising administering to said human a composition comprising a compound having the structure of Formula 1:

Trp-Arg-Tyr-Thr-Ala-Pro-Val-His-Leu-Gly-Asp-Gly-dAla-Lys-CHAla-Val-Ala-Ala-Trp-Thr-Leu-Lys-Ala-Ala-dAla-NH$_2$    Formula 1 wherein Ala13 and Ala25 are each D amino acids shown as dALa, and Ala at position 15 is cyclohexylalanine, a modified L configuration Alanine shown as CHAla.

11. The method of claim 10 wherein the human is also treated with surgery and/or chemotherapy.

12. The method of claim 10 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

13. The method of claim 1 wherein the human is identified as having a tumor that is HER2 positive.

14. The method of claim 13 further comprising treating the human with chemotherapy.

15. The method of claim 14 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

16. The method of claim 7 wherein the human is further treated with surgery and/or chemotherapy.

17. The method of claim 7 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

18. A method of treating a human who has been diagnosed as having triple negative breast cancer, the method comprising administering to said human a composition comprising: a compound having the structure of Formula 1:

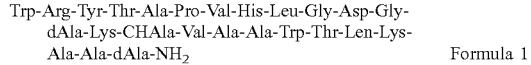

Trp-Arg-Tyr-Thr-Ala-Pro-Val-His-Leu-Gly-Asp-Gly-dAla-Lys-CHAla-Val-Ala-Ala-Trp-Thr-Len-Lys-Ala-Ala-dAla-NH$_2$     Formula 1 wherein Ala13 and Ala25 are each D amino acids shown as dALa, and Ala at position 15 is Cyclohexylalanine, a modified L configuration Alanine shown as CHAla, and an oil and surfactant adjuvant, wherein the oil is mineral oil and the surfactant is mannide monooleate.

19. The method of claim 18 wherein the human is also treated with surgery and/or chemotherapy.

20. The method of claim 18 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

21. The method of claim 7 wherein the human is identified as having a tumor that is HER2 positive.

22. The method of claim 21 further comprising treating the human with chemotherapy.

23. The method of claim 22 further comprising treating the human with one or more anti-cancer chemotherapeutics selected from the group consisting of: doxorubicin, cyclophosphamide, docetaxel, cisplatin, vinorelbine, bortezomib, adriamycin, trastuzumab, paclitaxel, tamoxifen and pertuzumab.

24. The method of claim 10 wherein the human who has been diagnosed as having triple negative breast cancer has been diagnosed as having metastatic triple negative breast cancer.

25. The method of claim 18 wherein the human who has been diagnosed as having triple negative breast cancer has been diagnosed as having metastatic triple negative breast cancer.

26. The method of claim 11 wherein the human is also treated with chemotherapy and surgery.

27. The method of claim 11 comprising treating the human with one or more anti-cancer chemotherapeutics selected from the group consisting of: docetaxel and paclitaxel.

28. The method of claim 27 wherein the human is also treated with surgery.

29. The method of claim 13 comprising treating the human with one or more anti-cancer chemotherapeutics selected from the group consisting of: docetaxel and paclitaxel.

30. The method of claim 13 wherein said breast cancer that is HER2 positive is metastatic.

31. The method of claim 19 wherein the human is also treated with chemotherapy and surgery.

32. The method of claim 19 comprising treating the human with one or more anti-cancer chemotherapeutics selected from the group consisting of: docetaxel and paclitaxel.

33. The method of claim 32 wherein the human is also treated with surgery.

34. The method of claim 21, further comprising treating the human with one or more anti-cancer chemotherapeutics selected from the group consisting of: docetaxel and paclitaxel.

35. The method of claim 21 wherein said breast cancer that is HER2 positive is metastatic.

36. The method of claim 10 further comprising treating the human with one or more anti-cancer chemotherapeutics, anti-cancer radioactive agent and/or with anti-cancer radiation therapy.

37. The method of claim 10 wherein composition further comprises adjuvant.

38. The method of claim 37 wherein adjuvant is selected from the group consisting of an oil and surfactant adjuvant and QS21 adjuvant.

39. The method of claim 10 wherein the composition comprises the compound having the structure of Formula 1 in an amount selected from the group consisting of: at least 300 µg, at least 500 µg, and at least 1000 µg.

40. The method of claim 18 further comprising treating the human with one or more anti-cancer chemotherapeutics, anti-cancer radioactive agent and/or with anti-cancer radiation therapy.

41. The method of claim 18 wherein the composition comprises the compound having the structure of Formula 1 in an amount selected from the group consisting of: at least 300 µg, at least 500 µg, and at least 1000 µg.

42. The method of claim 7 further comprising treating the human with one or more anti-cancer chemotherapeutics, anti-cancer radioactive agent and/or with anti-cancer radiation therapy.

43. The method of claim 7 wherein the composition comprises the compound having the structure of Formula 1 in an amount selected from the group consisting of: at least 300 µg, at least 500 µg, and at least 1000 µg.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Trp Arg Tyr Thr Ala Pro Val His Leu Gly Asp Gly
1               5                   10

<210> SEQ ID NO 2
<211> LENGTH: 15
<212> TYPE: PRT
<213> ORGANISM: Artificial Sequence
<220> FEATURE:
<223> OTHER INFORMATION: synthetic sequence

<400> SEQUENCE: 2

Gly Val Val Trp Arg Tyr Thr Ala Pro Val His Leu Gly Asp Gly
1               5                   10                  15

<210> SEQ ID NO 3
<211> LENGTH: 10
<212> TYPE: PRT
<213> ORGANISM: Artificial Sequence
<220> FEATURE:
```

```
<223> OTHER INFORMATION: synthetic sequence
<220> FEATURE:
<221> NAME/KEY: MOD_RES
<222> LOCATION: (2)..(2)
<223> OTHER INFORMATION: cyclohexylalanine

<400> SEQUENCE: 3

Lys Xaa Val Ala Ala Trp Thr Leu Lys Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: cyclohexylalanine

<400> SEQUENCE: 4

Ala Lys Xaa Val Ala Ala Trp Thr Leu Lys Ala Ala
1               5                   10

<210> SEQ ID NO 5
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: cyclohexylalanine

<400> SEQUENCE: 5

Ala Lys Xaa Val Ala Ala Trp Thr Leu Lys Ala Ala Ala
1               5                   10
```